US009822412B2

(12) United States Patent
Gromminger et al.

(10) Patent No.: US 9,822,412 B2
(45) Date of Patent: *Nov. 21, 2017

(54) DETECTION OF DNA THAT ORIGINATES FROM A SPECIFIC CELL-TYPE

(71) Applicant: LifeCodexx AG, Constance (DE)

(72) Inventors: Sebastian Gromminger, Constance (DE); Wera Hofmann, Constance (DE); Hamed Said, Constance (DE)

(73) Assignee: LifeCodexx AG, Constance (DE)

( * ) Notice: Subject to any disclaimer, the term of this patent is extended or adjusted under 35 U.S.C. 154(b) by 27 days.

This patent is subject to a terminal disclaimer.

(21) Appl. No.: 14/707,087

(22) Filed: May 8, 2015

(65) Prior Publication Data

US 2015/0322511 A1 Nov. 12, 2015

(30) Foreign Application Priority Data

May 9, 2014 (EP) .................................... 14167775

(51) Int. Cl.
*C12Q 1/68* (2006.01)
(52) U.S. Cl.
CPC ......... *C12Q 1/6881* (2013.01); *C12Q 1/6886* (2013.01); *C12Q 2600/154* (2013.01)
(58) Field of Classification Search
None
See application file for complete search history.

(56) References Cited

U.S. PATENT DOCUMENTS

| | | | |
|---|---|---|---|
| 5,804,375 A | 9/1998 | Gelfand et al. | |
| 5,994,056 A | 11/1999 | Higuchi | |
| 6,200,756 B1 | 3/2001 | Herman et al. | |
| 6,258,569 B1 | 7/2001 | Livak et al. | |
| 6,331,393 B1 | 12/2001 | Laird et al. | |
| 6,727,356 B1 | 4/2004 | Reed et al. | |
| 6,929,907 B2 | 8/2005 | Agris | |
| 2012/0252015 A1* | 10/2012 | Hindson | C12Q 1/6883 435/6.11 |

FOREIGN PATENT DOCUMENTS

| | | |
|---|---|---|
| EP | 0 512 334 B1 | 9/1999 |
| EP | 0 706 649 B1 | 1/2001 |
| EP | 0 792 374 B1 | 1/2001 |
| EP | 0 954 608 B1 | 5/2006 |
| EP | 1 185 695 B1 | 7/2006 |
| EP | 0 543 942 B2 | 11/2006 |
| EP | 1 235 938 B1 | 2/2012 |
| WO | 2005/118852 A2 | 12/2005 |
| WO | 2007/132166 A3 | 11/2007 |
| WO | 2007/132167 A3 | 11/2007 |
| WO | 2010/033639 A9 | 3/2010 |
| WO | 2011/018600 A1 | 2/2011 |
| WO | 2011/034631 A1 | 3/2011 |
| WO | 2012/092592 A1 | 7/2012 |

OTHER PUBLICATIONS

He et al., "Development of a multiplex MethyLight assay for the detection of multigene methylation in human colorectal cancer", Cancer Genetics and Cytogenetics, Oct. 1, 2010, vol. 202:1, pp. 1-10.
Olkhov-Mitsel et al., "Novel Multiplex MethyLight Protocol for Detection of DNA Methylation in Patient Tissues and Bodily Fluids", Scientific Reports, Mar. 21, 2014, vol. 4: 4432, pp. 1-8.
Snellenberg et al., "Development of a multiplex methylation-specific PCR as candidate triage test for women with an HPV-positive cervical scrape", BMC Cancer, Nov. 23, 2012, vol. 12:551, pp. 1-10.
Nygren et al., "Quantification of Fetal DNA by Use of Methylation-Based DNA Discrimination", Clinical Chemistry, Aug. 20, 2010, vol. 56:10, pp. 1627-1635.
Campan et al., "MethyLight", DNA Methylation: methods and Protocols, Second Edition , 2009, vol. 57, pp. 325-337.
Swift-Scanalan et al., "Two-color quantitative multiplex methylation-specific PCR", ' BioTechniques, Feb. 1, 2006, vol. 40:2, pp. 210-219.
Weisenberger et al., "Analysis of repetitive element DNA methylation by MethyLight", Nucleic Acids Research, Dec. 2, 2005, vol. 33:21, pp. 6823-6836.
Weisenberger et al., "DNA methylation analysis by digital bisulfite genomic sequencing and digital MethyLight", Nucleic Acids Research, Aug. 1, 2008, vol. 36:14, pp. 4689-4698.
Sperling et al., "Twin pregnancy: the role of ultrasound in management", Acta Obstet Gynecol Scand, 2001, vol. 80, pp. 287-299.
Sorenson et al., "Soluble Normal and Mutated DNA Sequences from Single-Copy Genes in Human Blood", Cancer Epidemiology, Biomarkers & Prevention, Jan./Feb. 1994, vol. 3, pp. 67-71.
Vasioukhin et al., "Point mutations of the N-ras gene in the blood plasma DNA of patients with myelodysplastic syndrome or acute myelogenous leukaemia", British Journal of Haematology, 1994, vol. 86, pp. 774-779.
Lo et al., "Presence of fetal DNA in maternal plasma and serum", The Lancet, Aug. 16, 1997, vol. 350, pp. 485-487.
Muller et al., "Methylated DNA as a possible screening marker for neoplastic disease in several body fluids", Expert Rev. Mol. Diagn., 2003, vol. 3(4), pp. 443-458.
Lo et al., "Quantitative Analysis of the Bidirectional Fetomaternal Transfer of Nucleated Cells and Plasma DNA", Clinical Chemistry, 2000, vol. 46:9, pp. 1301-1309.

(Continued)

*Primary Examiner* — James Martinell
(74) *Attorney, Agent, or Firm* — MH2 Technology Law Group, LLP

(57) ABSTRACT

The present invention relates to methods to detect an amount of DNA that originates from cells of a given type, where the sample comprising such DNA in admixture with DNA that does not originate from such cells. Such methods are based on differential methylation, at certain regions, of the DNA that originates from the given type of cells compared to the admixed DNA. Such methods have particular application in the detection, from a biological fluid from a pregnant female, of cell free DNA that originates from a foetus or the placenta of a foetus, or the detection, from a biological fluid from an individual, of cell free DNA that originates from cells of a tumor. Accordingly, such methods have diagnostic, prognostic and/or predictive utility for detecting an increased risk of an individual suffering from or developing a medical condition such as preeclampsia or cancer, and/or to aid subsequent diagnostic, prognostic and/or predictive methods such as the detection of chromosomal trisomy in a foetus, including for twin-pregnancies. The present invention also relates to compositions, kits, computer program products and other aspects that are used in, useful for or related to the practice of such methods.

23 Claims, 3 Drawing Sheets

(56) References Cited

OTHER PUBLICATIONS

Smid et al., "Correlation of fetal DNA levels in maternal plasma with Doppler status in pathological pregnancies", Prenat Diag, 2006, pp. 785-790.
Lo et al., "Rapid Clearance of Fetal DNA from Maternal Plasma", Am. J. Hum. Genet, 1999, vol. 64, pp. 218-224.
Kawai et al., "Methylation profiles of genomic DNA of mouse developmental brain detected by restriction landmark genomic scanning (RLGS) method", Nucleic Acids Research, 1993, vol. 21:24, pp. 5604-5608.
Masuzaki et al., "Detection of cell free placental DNA in maternal plasma: direct evidence from three cases of confined placental mosaicism", J. Med. Genet, 2004, vol. 41, pp. 289-292.
Flori et al., "Circulating cell-free fetal DNA in maternal serum appears to originate from cyto- and syncytio-trophoblastic cells. Case Report", Human Reproduction, Jan. 29, 2004, vol. 19:3, pp. 723-724.
Chim et al., "Detection of the placental epigenetic signature of the maspin gene in maternal plasma", Proc. Natl. Acad. Sci. USA, Oct. 11, 2005, vol. 102:41, pp. 14753-14758.
Chiu et al., "Hypermethylation of RASSF1A in Human and Rhesus Placentas", The American Journal of Pathology, Mar. 2007, vol. 170:3, pp. 941-950.
Old et al., "Candidate epigenetic biomarkders for non-invasive prenatal diagnosis of Down syndrome", Reproductive BioMedicine Online, Jun. 21, 2007, vol. 15:2, pp. 227-235.
Chim et al., "Systematic Search for Placental DNA-Methylation Markers on Chromosome 21: Toward a Maternal Plasma-Based Epigenetic Test for Fetal Trisomy 21", Clinical Chemistry, 2008, vol. 54:3, pp. 500-511.
Lo et al., "Prenatal Diagnosis of Fetal RhD Status by Molecular Analysis of Maternal Plasma", The New England Journal of Medicine, Dec. 10, 1998, vol. 339, pp. 1734-1738.
Go et al., "Non-invasive aneuploidy detection using free fetal DNA and RNA in maternal plasma: recent progress and future possibilities", Human Reproduction update, 2011, vol. 17:3, pp. 372-382.
Lo et al. "Quantitative Analysis of Fetal DNA in Maternal Plasma and Serum: Implications for Noninvasive Prenatal Diagnosis", Am. J. Hum. Genet., 1998, vol. 62, pp. 768-775.
Lo et al., "Quantitative Abnormalities of Fetal DNA in Maternal Serum in Preeclampsia", Clinical Chemistry, 1999, vol. 45:2, pp. 184-188.
Yu et al., "Quantification of Maternal Serum Cell-Free Fetal DNA in Early-Onset Preeclampsia", Int. J. Mol. Sci, Apr. 8, 2013, vol. 4, pp. 7571-7582.
Hahn et al., "Cell-Free Nucleic Acids as Potential Markers for Preeclampsia", Placenta, 2011, vol. 32, pp. S17-S20.
Li et al., "Hypermethylation of multiple tumor-related genes associated with DMNT3b upregulation served as a biomarker for early diagnosis of esophageal squamous cell carcinoma", Epigenetics, Mar. 2011, vol. 6:3, pp. 307-316.
Ha et al., "Elevated Levels of Cell-Free Circulating DNA in Patients with Acute Dengue Virus Infection", PLoS One, Oct. 7, 2011, vol. 6:10, e25969, pp. 1-7.
Outinen et al., "Plasma Cell-Free DNA Levels Are Elevated in Acute Puumula Hantavirus Infection", PLoS One, Feb. 7, 2012, vol. 7:2, e31455, pp. 1-7.
Forsblom et al., "High Cell-Free DNA Predicts Fatal Outcome among *Staphylococcus aureus* Bacteraemia Patients with Intensive Care Unit Treatment", PLoS One, Feb. 10, 2014, vol. 9:2, e87741, pp. 1-9.
Chan et al., "Size Distributions of Maternal and Fetal DNA in Maternal Plasma", Clinical Chemistry, 2004, vol. 50:1, pp. 88-92.
Kimura et al., "Fragment Size Analysis of Free Fetal DNA in Maternal Plasma Using Y-STR Loci and SRY Gene Amplification", Nagoya J. Med. Sci., 2011, vol. 73, pp. 129-135.
Lo et al., "Maternal Plasma DNA Sequencing Reveals the Genome-Wide Genetic and Mutational Profile of the Fetus", Science Translational Medicine, Dec. 8, 2010, vol. 2:61, 61ra91 pp. 1-14.
Elshimali et al., "The Clinical Utilization of Circulating Cell Free DNA (CCFDNA) in Blood of Cancer Patients", International Journal of Molecular Sciences, 2013, vol. 14, pp. 18925-18958.
Sacha Zeerleder, "The struggle to detect circulating DNA", Critical Care, 2006, vol. 10:142, pp. 1-3.
Kirsch et al., "An Improved Method for the Isolation of Free-Circulating Plasma DNA and Cell-Free DNA from Other Body Fluids", Ann. N.Y. Acad. Sci., 2008, vol. 1137, pp. 135-139.
Struble et al., "Fetal Fraction Estimate in Twin Pregnancies Using Directed Cell-Free DNA Analysis", Fetal Diagnosis and Therapy, Dec. 7, 2013, pp. 1-5.
Gauthier et al., "Blood Clearance Kinetics and Liver Uptake of Mononucleosomes in Mice", The Journal of Immunology, 1996, vol. 156, pp. 1151-1156.
Lo et al., "Quantitative Analysis of Aberrant p16 Methylation Using Real-Time Quantitative Methylation-specific Polymerase Chain Reaction", Cancer Research, Aug. 15, 1999, vol. 59, pp. 3899-3903.
Birch et al., "Accurate and Robust Quantification of Circulating Fetal and Total DNA in Maternal Plasma from 5-41 Weeks of Gestation", Clinical Chemistry, 2005, vol. 51:2, pp. 312-320.
Papageorgiou et al., "Fetal-specific DNA methylation ratio permits non-invasive prenatal diagnosis of trisomy 21", Nat. Med., Apr. 7, 2011, vol. 17:4, pp. 1-13.
Tong et al., "Technical concerns about immunoprecipitation of methylated fetal DNA for noninvasive trisomy 21 diagnosis", Nature Medicine, Sep. 2012, vol. 18:9, pp. 1327-1328.
Hindson et al., "High-Throughput Droplet Digital PCR System for Absolute Quantitation of DNA Copy Number", Anal. Chem., 2011, vol. 83, pp. 8604-8610.
White et al., "Evaluation of a Novel Assay for Detection of the Fetal Marker RASSF1A: Facilitating Improved Diagnostic Reliability of Noninvasive Prenatal Diagnosis", PLoS One, Sep. 14, 2012, vol. 7:9, e45073 pp. 1-5.
Qu et al., "Noninvasive Prenatal Determination of Twin Zygosity by Maternal Plasma DNA Analysis", Clinical Chemistry, 2013, vol. 59:2, pp. 427-435.
Lim et al., "Disease specific characteristics of fetal epigenetic markers for non-invasive prenatal testing of trisomy 21", BMC Medical Genomics, 2014, vol. 7:1, pp. 1-11.
Poon et al., "Differential DNA Methylation between Fetus and Mother as a Strategy for Detecting Fetal DNA in Maternal Plasma", Clinical Chemistry, 2002, vol. 48:1, pp. 35-41.
Yegnasubramanian et al., "Combination of methylated-DNA precipitation and methylation-sensitive restriction enzymes (COMPARE-MS) for the rapid, sensitive and quantitative detection of DNA methylation", Nucleic Acids Research, 2006, vol. 34:3, e19 pp. 1-14.
Papantoniou et al., "RASSF1A in maternal plasma as a molecular marker of preeclampsia", Prenatal Diagnosis, 2013, vol. 33, pp. 682-687.
Zeybek et al., "Clinical evaluations of cell-free fetal DNA quantities in pre-eclamptic pregnancies", J. Obstet Gynaecol Res., Mar. 2013, vol. 39:3, pp. 632-640.
Jakobsen et al., "Identifying mild and severe preeclampsia in asymptomatic pregnant women by levels of cell-free fetal DNA", Transfusion, Sep. 2013, vol. 53, pp. 1956-1964.
Chen et al., "Chimerism in Monochorionic Dizygotic Twins: Case Study and Review", Am. J. Med. Genet. Part A, May 22, 2013, vol. 161A, pp. 1817-1824.
Chan et al., "Hypermethylated RASSF1A in Maternal Plasma: A Universal Fetal DNA Marker that Improves the Reliability of Noninvasive Prenatal Diagnosis", Clinical Chemistry, 2006, vol. 52:12, pp. 2211-2218.
Stumm et al., "Diagnostice accuracy of random massively parallel sequencing for non-invasive prenatal detection of common autosomal aneuploidies: a collaborative study in Europe", Prenatal Diagnosis, 2014, vol. 34, pp. 185-191.
Leung et al., "Noninvasive twin zygosity assessment and aneuploidy detection by maternal plasma DNA sequencing", Prenatal Diagnosis, 2013, vol. 33, pp. 675-681.

(56) References Cited

OTHER PUBLICATIONS

Tong et al., "Noninvasive Prenatal Detection of Fetal Trisomy 18 by Epigenetic Allelic Ratio Analysis in Maternal Plasma: Theoretical and Empirical Considerations", Clinical Chemistry, 2006, vol. 52, No. 12, pp. 2194-2202.
Papageorgiou et al., "Sites of Differential DNA Methylation between Placenta and Peripheral Blood", The American Journal of Pathology, May 2009, vol. 174, No. 5, pp. 1609-1618.

* cited by examiner

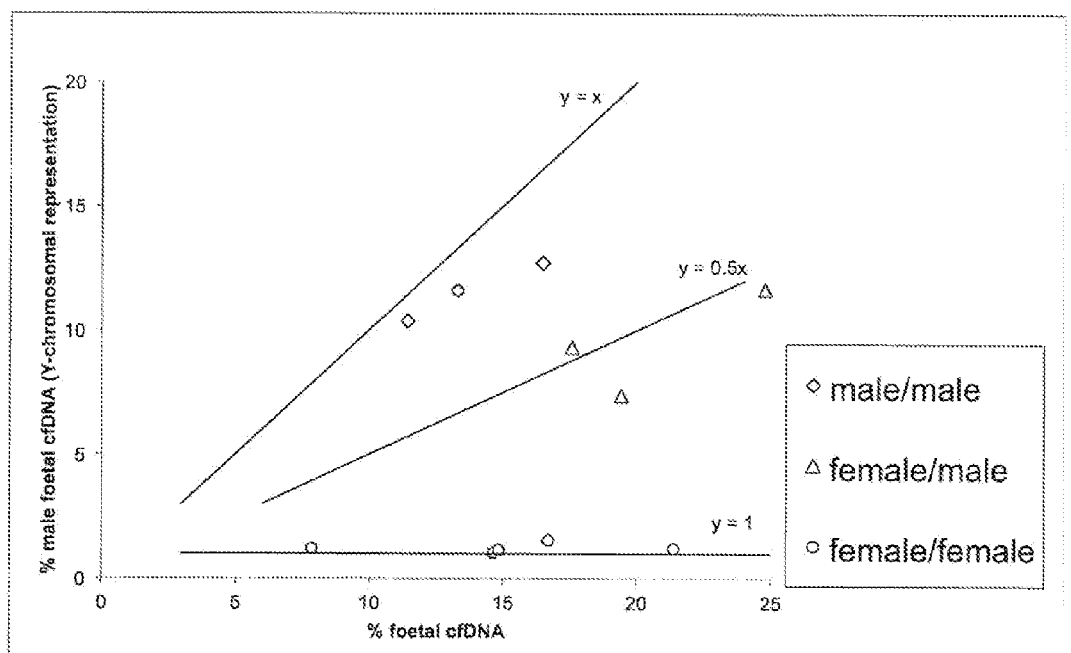
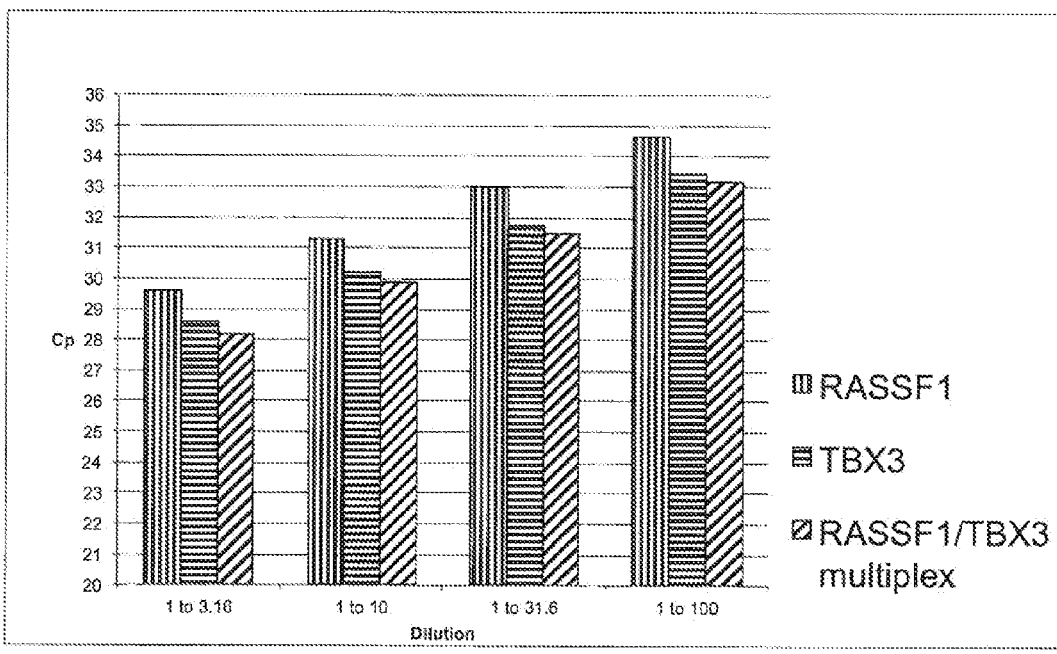

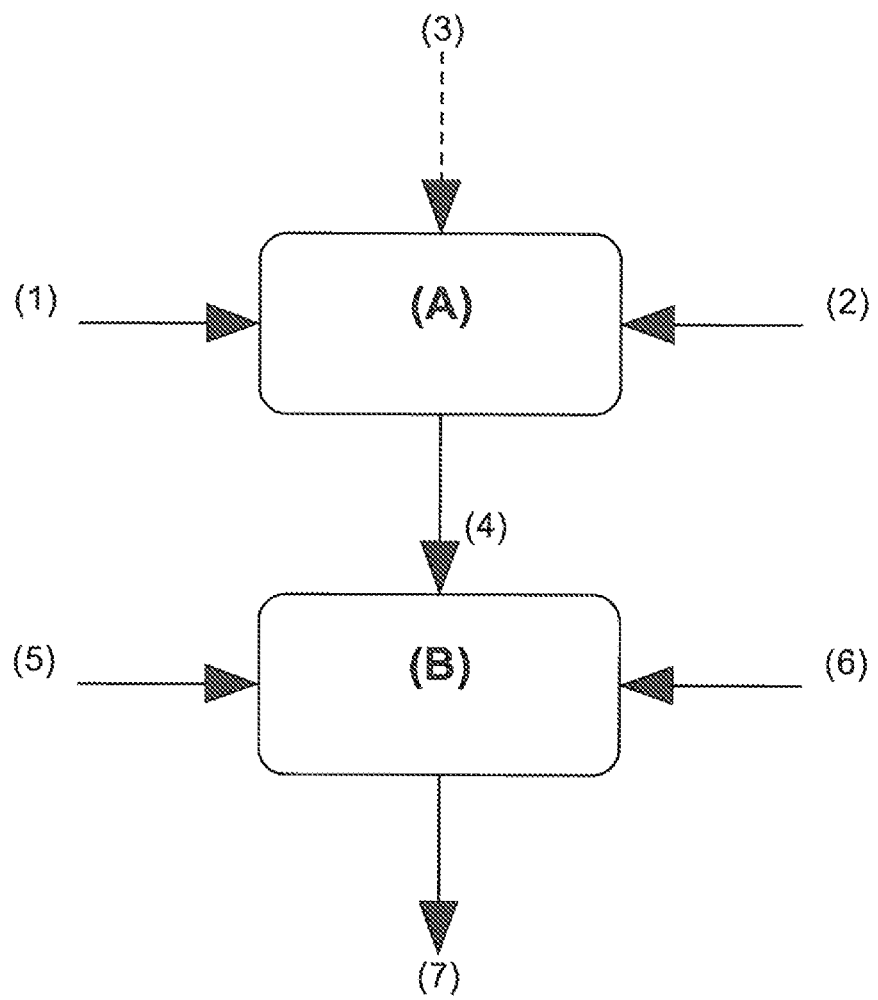

SEQUENCE LISTING

```
<160> NUMBER OF SEQ ID NOS: 14

<210> SEQ ID NO 1
<211> LENGTH: 20
<212> TYPE: DNA
<213> ORGANISM: Artificial Sequence
<220> FEATURE:
<223> OTHER INFORMATION: primer

<400> SEQUENCE: 1
attgagctgc gggagctggc                                              20

<210> SEQ ID NO 2
<211> LENGTH: 18
<212> TYPE: DNA
<213> ORGANISM: Artificial Sequence
<220> FEATURE:
<223> OTHER INFORMATION: primer

<400> SEQUENCE: 2
tgccgtgtgg ggttgcac                                                18

<210> SEQ ID NO 3
<211> LENGTH: 15
<212> TYPE: DNA
<213> ORGANISM: Artificial Sequence
<220> FEATURE:
<223> OTHER INFORMATION: probe

<400> SEQUENCE: 3
acccggctgg agcgt                                                   15

<210> SEQ ID NO 4
<211> LENGTH: 20
<212> TYPE: DNA
```

```
<213> ORGANISM: Artificial Sequence
<220> FEATURE:
<223> OTHER INFORMATION: primer

<400> SEQUENCE: 4
ggtcatccac caccaagaac                                               20

<210> SEQ ID NO 5
<211> LENGTH: 20
<212> TYPE: DNA
<213> ORGANISM: Artificial Sequence
<220> FEATURE:
<223> OTHER INFORMATION: primer

<400> SEQUENCE: 5
tgcccaagga tgctgtcaag                                               20

<210> SEQ ID NO 6
<211> LENGTH: 20
<212> TYPE: DNA
<213> ORGANISM: Artificial Sequence
<220> FEATURE:
<223> OTHER INFORMATION: probe

<400> SEQUENCE: 6
gggcctcaat gacttcacgt                                               20

<210> SEQ ID NO 7
<211> LENGTH: 20
<212> TYPE: DNA
<213> ORGANISM: Artificial Sequence
<220> FEATURE:
<223> OTHER INFORMATION: primer

<400> SEQUENCE: 7
ggtgcgaact cctctttgtc                                               20

<210> SEQ ID NO 8
<211> LENGTH: 20
<212> TYPE: DNA
<213> ORGANISM: Artificial Sequence
<220> FEATURE:
<223> OTHER INFORMATION: primer

<400> SEQUENCE: 8
ttaatcaccc agcgcatggc                                               20

<210> SEQ ID NO 9
<211> LENGTH: 20
<212> TYPE: DNA
<213> ORGANISM: Artificial Sequence
<220> FEATURE:
<223> OTHER INFORMATION: probe

<400> SEQUENCE: 9
ccctcccggt gggtgataaa                                               20

<210> SEQ ID NO 10
<211> LENGTH: 20
<212> TYPE: DNA
<213> ORGANISM: Artificial Sequence
<220> FEATURE:
<223> OTHER INFORMATION: primer

<400> SEQUENCE: 10
tgttcactgg aggactcatc                                               20
```

<210> SEQ ID NO 11
<211> LENGTH: 19
<212> TYPE: DNA
<213> ORGANISM: Artificial Sequence
<220> FEATURE:
<223> OTHER INFORMATION: primer

<400> SEQUENCE: 11
cagtccatga gggtgtttg                                                   19

<210> SEQ ID NO 12
<211> LENGTH: 18
<212> TYPE: DNA
<213> ORGANISM: Artificial Sequence
<220> FEATURE:
<223> OTHER INFORMATION: probe

<400> SEQUENCE: 12
gaggtcccat tctcctttt                                                   18

<210> SEQ ID NO 13
<211> LENGTH: 18151
<212> TYPE: DNA
<213> ORGANISM: Homo sapiens
<220> FEATURE:
<223> OTHER INFORMATION: RASSF1

<400> SEQUENCE: 13
gacttggcgt ctgaggacag agtccagacc acaaggatct ggagctcagg agagactcgt       60
gggccacagc ccgagaaagc gctgggaatc caaatactat ggcgattggc agtcgcgtag      120
gcgaggcggg ctagagaccc gcccggattt aggcgcgagc cacctccagg ggcggggccc      180
aggccgcact gcgcaggcgc ggctaacccg tttccatggc tgcgagaact gacgctcccc      240
aaccgtcccg caactgtcct gtcccagact ttggcaccgt cggggtccgt cgtcccgaa       300 tgtgacagca tccccacccc ggctgctgcc caggatccgc cggaccccgg cctcgatatg      360
ggagacctgg aactgctgct gcccggggaa gctgaagtgc tggtgcgggg tctgcgcagc      420
ttcccgctac gcgagatggg ctccgaaggg tgaggcaccc gggtcaggcg gagtcccgga      480
gtcattgtcc ttgagtcggg gagctggggc ctgactcggg ggaggggctg cccagtgtgg      540
aggggctccc aaatggggga gcagagcgtt ccgagacagg agtattactg ctcctgagcc      600
ccctgtgtcc cctcaggatc aggttaggct tcagtaggat ccagccccca tccccactcc      660
taatgcacac acgtggacgc acatgcactt accctctgag gcaggtggaa ccagcagcat      720
gagaacctgg agaagctgaa catgcaagcc atcctcgatg ccacagtcag ccagggcgag      780
cccattcagg agctgctggt cacccatggg aaggtacccc gaggtcacag gcagggttcc      840
tgccttcccc catacctcac ctactctacc cctccggagt cccctgtgtg cccttcccct      900
ctggcctggt acacctgttc tccctgaagg acaaagagaa atgtgttaca tgtttcattt      960
tgtatcccta ttggacagga ctctggcaca ccaggctggg tgcagggcat gagttgatta     1020
gggagaaagc tgtaggtcct agaacagctt aggcttcaag gggaaggccc aaatgctaaa     1080
ggcatctgtg aattgactgt aaggctggtg gtggggaagg ggtggggagg ggttgggagg     1140
ggcgggaggg aggggagata acctaactgg aggtggaact tcggcatgga aggaagcagc     1200
cttcccaaca tgaaaggggg aagttagaaa ccagggagag gcctggctgg aacatggacc     1260
agggagtgtc accagcagat gacctgagat atcaattgac caaaaaaaaa aaaaaaaaag     1320

```
ccgggcatgg tagctcatgc ctgttatccc agcattttgg gaggccaaga cgggtggatc   1380
atctgaggtc aggagttcaa ggccagcctg gccaacatgg tgaaacccca cctctactaa   1440
aaatacaaaa atttgcagag catggtggtg cacacctgta atcccagcta ctcgggaggc   1500
tgaggcagga gaatcgcttg aacctgggag gcagaggtta cagagagcca agatcatgcc   1560
actgcactcc agcctgggtg acaagagtga aactccgtct caaaaaaaaa aaaaaaaaa    1620 agaaaggtcc tttgcaaaag aaagatggaa ctcatactag gggataggat aggaacaggg   1680
cactgtgaag ggtcctgagt aggagtgagg ccaaggcaca caagagcttt ggaggaccac   1740
agacagggac tagagggagg gcatgaggag aagggctggc ttgaaaggga tgcctgaatg   1800
ggcgggcaga ggataagggt gcaggtgcag gcagggcaag gcagtctggg aactgggcag   1860
gagccagtca cataagcatg agggacatcc acagaggtgt tgggagcagc tggtaatgaa   1920
ggtccaaggt gcaagagaga agtcaggaag gatactcatg ggtctggaat agtttagggg   1980
cccagcagtg tttggggata tcaggggttga gctgagccgg ggatggggagg gttgccaggc  2040 aaaggtaggc ccatctcatc cctgtccttt accctaccct tcaaaggtcc caacactggt   2100
ggaggagctg atcgcagtgg agatgtggaa gcagaaggtg ttccctgtgt tctgcagggt   2160
ggaggacttc aagccccaga acaccttccc catctacatg gtggtgagct gggcccctgg   2220
ttcataccct ttctcactcc ttcagagggc tctggaccgg ggaggagagc tggtagcccc   2280
tatcccttcc tcaggccctg tccttctctt tatctgacag gtgcaccacg aggcctccat   2340
catcaacctc ttggagacag tgttcttcca caaggtgagg gactatctct gcccatgggc   2400
cacagttccg ggtcagggcc tggcaggaag ggagattgtg tctgtgtggg gaaggcatca   2460
gacacagaaa gtttccctcc tcctttttccc aggaggtgtg tgagtcagca aagacactg   2520 tcttggactt ggtagactat tgccaccgca aactgaccct gctggtggcc cagagtggct   2580
gtggtggccc ccctgagggg gagggatccc aggacagcaa ccccatgcag gtgggttgag   2640
gttacctagg gttgtgaaag cctaggtctg ggttccccaa ggcctgcgca ggtgaggtg    2700 gcccagcgtg aacactgtgt gacctcccag gagctgcaga agcaggcaga gctgatggaa   2760
tttgagattg cactgaaggc cctctcagta ctacgctaca tcacagactg tgtggacagg   2820
tgagcagtcc gactgggcct gggcctactg tggagggctg gaagaccggg cctgtagcct   2880
gcctctactc acctccttca caacgtccct gcccctagcc tctctctcag caccttgagc   2940
cgtatgctta gcacacacaa cctgccctgc ctcctggtgg aactgctgga gcatagtccc   3000
tggagccggc gggaaggagg tagggtcctc ccccaccagc ctaagcccca ggctactgct   3060
tcagggtatc ttttttgatag agggggggcag cttgcacaca cgaagacaaa ccctgtcccc   3120
aagcccactg aggataccag gatgcctcag ccaaggttgg cctagacctg agctctgcag   3180
caggccaggc ccatgtgtcc actactgagg ctcaccctgc tctgggtca gcagccctat   3240 agcctgggca gtcctgcag cccaggttct cccattccca ggcagtggtc agtctcccag   3300
cccccacagc tggctcactt gaagagaatt caacgtctgc acccagtgtg ctggttcctc   3360
tccccaggca agctgcagca gttcgagggc agccgttggc atactgtggc cccctcagag   3420
cagcaaaagc tgagcaagtt ggacgggcaa gtgtggatcg ccctgtacaa cctgctgcta   3480
agccctgagg ctcaggcgcg ctactgcctc acaagttttg ccaagggacg gctactcaag   3540
gtcagactcc ctccgcacca gcccccacag cccagtacc gccctcccca tcctaccccg   3600
actgcgtccc tgctgtttat ctttgcccac ccacctcaac cccagtgctc ttttcagtcc   3660
ttgggcctca ggtgacacac cagctagtgg gacatgggcc cccacaggca ttctcagccc   3720
```

```
aacccagccc cttccttttc cttggccccc tggccagcac ctgcatcaca ctggcctcca   3780
ctggacaccc ttgcagcttc gggccttcct cacagacaca ctgctggacc agctgccaa    3840
cctggcccac ttgcagagtt tcctggccca tctgacccta actgaaaccc agcctcctaa   3900
gaaggacctg gtgttggaac aggtaggcac tggaaagtta gctgctcagg accactgtcc   3960
cactttacca gcaccttcct gccactctcc acttctctct cctagatccc agaaatctgg   4020
gagcggctgg agcgagaaaa cagaggcaag tggcaggcaa ttgccaagca ccagctccag   4080
catgtgttca gcccctcaga gcaggacctg cggctgcagg cgcgaaggta aggcctgtgg   4140
aaatggcagg gagggtggag gggatgcagg aggcatggat gtgggtgggg tgcccccacc   4200
ttccagggcc agtcagacct tcctgacttt cccccaggtg ggctgagacc tacaggctgg   4260
atgtgctaga ggcagtggct ccagagcggc ccgctgtgc ttactgcagt gcagaggctt    4320
ctaagcgctg ctcacgatgc agaatgagt ggtattgctg caggtgaggg tatcctagaa    4380
ccttggacct ctaagcccta ctcccacatc ccccacatgc attgccatcc tcaatacccca  4440
cctgcctgca gggagtgcca agtcaagcac tgggaaaagc atggaaagac ttgtgtcctg   4500
gcagcccagg gtgacagagc caaatgaggg ctgcagttgc tgagggccga ccacccatgc   4560
caagggaatc cacccagaat gcaccctga acctcaagat cacggtccag cctctgccgg    4620
agccccagtc tccgcagtgg agagcagagc gggcggtaaa gctgctgacc gatctccctc   4680
ctcctcaccc caagtgaagg ctcgagactt cctgccccac ccagtgggta ggccaagtgt   4740
gttgcttcag caaccggac caggagggcc agggccggat gtggggaccc tcttcctcta    4800
gcacagtaaa gctggcctcc agaaacacgg gtatctccgc gtggtgcttt gcggtcgccg   4860
tcgttgtggc cgtccggggt ggggtgtgag gagggacga aggagggaag gaagggcaag    4920
gcggggggg ctctgcgaga gcgcgcccag ccccgccttc gggccccaca gtccctgcac    4980
ccaggttttcc attgcgcggc tctcctcagc tccttcccgc cgcccagtct ggatcctggg  5040
ggaggcgctg aagtcggggc ccgccctgtg gcccgcccg gccgcgctt gctagcgccc     5100
aaagccagcg aagcacgggc ccaaccgggc catgtcgggg gagcctgagc tcattgagct   5160
gcgggagctg gcaccgctg ggcgcgctgg gaagggccgc accgggctgg agcgtgccaa    5220
cgcgctgcgc atcgcgcggg gcaccgcgtg caaccccaca cggcagctgg tccctggccg   5280
tggccaccgc ttcagcccg cggggcccgc cacgcacacg tggtgcgacc tctgtggcga    5340
cttcatctgg ggcgtcgtgc gcaaaggcct gcagtgcgcg cgtgagtagt ggccccgcgc   5400
gcctacgaga gcgaaggggg cagccaaggg gcagcgcagt cgccgcgggt caagtcgcgg   5460
cagaggggggt cggcggggac agctcccgag gactaggtcc gttactttcg ccccatcgct  5520
gaaagagtgcg cgaaaatggt ttatcccttg tcgcactcca ctcgtatctg gccacagat   5580
gagcagaggt ggctgcttat atgtaaaaat acgctgattt taagtttctt atctttaaaa   5640
tgccttggcc cttcttgaga aagggtttgt gcctactgtc ctcggagtcc atcttcccag   5700
gcttgcctct tctcaaacac tcatgacccc ctccagaacc tttagggtga agggaaatta   5760
ccacctatgg gagggagcct ggaaaaattt agaaccttg gtgggccccc tgcaagcagg    5820
agttttgttg agtctttatt tagcaaacac ccttttctga cccagtgaat cagatgctaa   5880
aatatgcacg cagccacaca cccagcagtc cttctgcacc cctgggaatc gccagcaagc   5940
aaaggttgct ctcccctggg tagacaccag ctggaatcac caggggtgct tttacagtcc   6000
tccccgctag cctggatccc accgcagacc tgttgaatca actgctggga gtggacccta   6060
```

-continued

```
ggcatcagta aattttaaaa actccccaaa ttattgtaac atggagtctg ggttgagcat      6120
cactgctctg gcctatttag gaacttgtgg atggatagtg tcccaggtct gtgtgtgcat      6180
ggagaccctc tcatccggta caagaggaca tcacaaattc agctgggggg agcacaaagt      6240
tgtgacagaa tgcaaagaat gaacaagggg ccgagcgcgg tggctcatgc ctgtaatccc      6300
agcacttcgg aaggcggagg cgggtggatc acctgaggtc aggagttcaa gaccagcctg      6360
gccaacatgt gaaacctca tgtctactaa aaaataaaaa aaaatgagcc aggcgtagtg       6420
gcgggtgcct gtaatcccag ctactcggga ggctgaggtg ggagaattgc ttgaacacag      6480
gaggcggagg ttgcagtgag ccgagatcgt gccactgccc tccagccttg gcacagagt      6540 gagactctgt ctcaaaaaaa aaaaaaaaa aaaaagaac aaggctggga cattgcagcg       6600
ttctcaaaga gaaataaagt agccatggag ataagaagca ggatgatttg ggcatgttta     6660
tcagaggtag agacaaggga gaaatcaaag ataagtttgg gcttttgtct ccagtaactg     6720
ggagcctagt ggccattttt gctgcaaaga ggaagctggg caagtgtagc agtgaggctg     6780
aagaaaaggg aattaaattt tggccatgtt cacttgaaac gtcttttaga catcctagtg     6840
aaggtactgg cacggaggat ctagtctgag ggtttaggtc agtgtttcag ccgtggatct     6900
ggggcagatg aatgtagaca gaccaggcca gtgatcagga ctgagcccag acttcatcgt     6960
gagatatgga agttgagtca gaatctgcaa aggagctgag caggagctgc agggggtagg     7020
aggaaaactg ggagagtgta gcccctggga gtcaaaggga gcaagcttca aatgatgctg     7080
agggggtgag aatggagaat ggaacactgg attccatttg gtagtacaca gatcgctgag     7140
gaccctgtcc cggcagtttt cctggaggaa gaggcaagcc tggctggagt gggtagaggg     7200
gagagtgaag gcgaaggatt agagtgtata gagaccagtg tcttggtctg aggggagtag     7260
agacaggtga caaccacagg gcagacgtag gttaaaggtg tttagttttt ccttcaagta    7320
aatgggcaga tgtattccat atacgttccc agtgaagggc cgggtgcggt ggctcaagcc    7380
tgtagtccca gcactttgga aggccgaggc gggtggatca cctgagatca ggagtttgag    7440
accagcctgg ctaacatggt gaaacccgt ctctactaaa aatacaaaaa ttagctgggc     7500
atggtggcgg gcgcctgtaa tcctaggtac tcaggaggct gaggcagaag aatcgcttga    7560
acccaggagg cggaggttgc ggtgagccga atcgcgcca ttgcactcca gcctgggtga    7620
caaaagcaag acgcagtttt tgttgttgt tttttaatt gccaatgagg aaaggggaag      7680
ttctgtgcta ggcgatagag atccaactgt tgagcaggcc tctctgcctg tggccttccg    7740
gccggtttcc agacgcccag gtggccaaca ttagagtccg cgtagcagtg tgaggtaacc    7800
cactgagata ggtcgggcct gcggagcctg gcgagcagcg gccctctccc tggggcttcc    7860
cttcaatctc cgggacattt ccccgacctg gagctcctcc gcctcaccgc caggcctctc    7920
tgcagattgc aagttcacct gccactaccg ctgccgcgcg ctcgtctgcc tggactgttg    7980
cgggccccgg gacctgggct gggaacccgg ggtggagcgg gacacgaacg tggtgagcgc    8040
ggggccgagg gcgtatggga agggcgagga tgggcaggcc acagtgcagg cattctcgag    8100
ggctgcctgg gtgccgcgcg caaggagcgt tctaattgcc gatttcccgg cggcacagag    8160
aggctaattc tgcgcggggg ctgggagggg agcctggatt gccggctccg caagtactcc    8220
acccgctgca agcggacccg ggcccaggct gacccaggct ccgcgcacgc gcacttcccg    8280
caccttcccg ccctcgcctc cggccagagg ccactcttgt gcgcttgccc ggacgctggc    8340
acccgccccc gttccctgtg gtaggtgggg tctgtgagtg gagctccgga gcgatgaggt    8400
cattcctggg ggcgaagcgt gcgtgtcccc gccccggcgt tcctgcccca atgagacaag    8460
```

```
agctagatcc cggcgatcta cgtttcagtc ttaacggttg cggcgcggct ctggcccggg    8520
cgcacgcgca cactgacacg cgtacacgca cgcacgcgac cggggcggtg gttggcggct    8580
acggacgcgc aggactgggg gacgggcggg tacggctatg ggcgaggcgg aggcgccttc    8640
tttcgaaatg acctggagca gcacgacgag cagtggctac tgcagccaag aggactcgga    8700
ctcggagctc gagcagtact tcaccgcgcg aacctcgcta gctcgcaggc cgcgccggga    8760
ccaggtggga gccaggggt gccggcggc gggaggggaa gcggtcgctg gagctccgcc      8820
ctccccggtc cgttgccgcg tcctgggtcg gtgggcagcc ccaccctcct ggctacgtgg    8880
ctccccgcgg gtcctggccg gggacctgcc cgcggaaccg tgcgtaagac cccgattcca    8940
ccgcctagat gctgggtgcc ggggccccct tggtttctgt cacagacagg ttgaacacgg    9000
aaaaagcagc tgtatggctt gtggtagacc tgagccgggc attatccagc tatgactaaa    9060
gccgaccgag cagtttggac tagcacctcg atttccgcgt tcgaatgctc ctgctccctc    9120
cttggggaga ctaggggagg atgtggagag ggaagagtcc tcgccaggaa ttgagaagta    9180
tgtttaggaa aacttgagag gcagagagag atcctgctcc tccatctgca ctcctgtatg    9240
gagccagctg agccctcacc tcttccctgt tctggcctgt caccagctgc tggaatgtgg    9300
aagattctgt tcccttcctc tagggtggat ctggagaaag atttgggaat agataggaaa    9360
gaagtcttgt tttggaccat aagcattcag gagcacttta cccacaggaa gggggaaagc    9420
tagattataa aatgcctaaa gaggtggaaa aagagatcca ggttactaac ccaggactgt    9480
aaggtgtctc ggaacctcct aggtatcccc attatcggag aactgtgtgc cagatgccat    9540
tggtgtgacc accaggctca gagaaccagg cctaggcacc aggaaaaaga aacagggact    9600
gtgaagctca gtatgcctgg cagaaatggg gcggaaatcc ttatttaagt aaagaaagtg    9660
gagttgtgag tgatgcttca gataaaattt tacaaaattc cttacaaaat gggtggtgct    9720
cagcacgcca aaatcttagc ccagagcttg ggtgcaaggg ttgagttgag tgtagacccc    9780
tgggcttgtc ttcatgtcag tcagtcctga gccattttcc actgtggaaa ggtgggaaaa    9840
ccacaagaca ctaaccaatt gaaaaggagg gctagccacg gaggtgcaca cctgtaatcc    9900
cagctacttg ggagggtgag gcagaaggat cacttgaacc tgggaggcag aggttgcagt    9960
gagccaagat cgtgccactg cactccagcc tgagtgacag agtgagactc tgtctcaaaa   10020
atagaaaagg aagccaagta cggtggctca cacctctaat gccaatgctt tgggaggcca   10080
aggcaggtgg atcatttgca atcaggaatt cgaggtcagc ctggccaaca tggtgaaacc   10140
ctatctctac taaacataca aaattagcc gggcatggtg gtgtgtgact gtagtcccag    10200
ctacttggga gactgaatca cttcaaccgg gaggcaaagg ttgcagtgag ccaagatcgt   10260
gccactgcac tccaacctgg gtgacagggt gaggctctgt ctcaaaaaaa agaaagaagg   10320
ctgggcttgg tgactcatgc ctgtaatctc agcattttgg gaggccaagg caggcagatc   10380
acttgaggcc aagagttcga gacctgccag gccaacatag caaaacccg tctgtactga    10440 aaatacaaaa aaattatctg gccatggtgg tgtgtgcctg taatcccagc tactgggag    10500 gctgaggcag gagtatcact tgaacccaga agacagaggt tgcagtgagt cgagactggg   10560
ccactgcatt ccagcctgga tgagagcag agactctgtc tcaaaaaaa aaaaaaaaaa     10620 aagaaagaa taggaggctg agaagtccca agttatatgt taaaaaaaaa gaaaaaaca     10680 tcagttttag gccaggtgca gtggctcaca cctttaatcc cagcactttg gaagccgag     10740 gtgggtggat catgaggtca ggagttcaag accagcctgg ccaaaatggt gaacccgt      10800
```

```
ctcgactaaa aatacaaaaa attagccagt tgtggtggca ggcacctgta atcccagcta   10860
cttgggaggc tgaagcagag aattgcttga acccaggagg cagagattgc aatgagccaa   10920
gatcgcacca ctgcactcca gcctggaaaa cagagcgaga ctctgtctca aaaaaaaaac   10980
catcagtttt tatggacagt ggtagagtgg agggtgggtc cctatggtgc agaagggaaa   11040
ttccatggtc ctgctgtgca tccgactggg atggctgttg aaatcctctt ccagcaggca   11100
gctttggaaa cagaaaaaga aactcttcct cctttagaat cctggaaggg ctgtgcagtg   11160
cctctaatcc aagtctgttt tctgagtgaa gatagggagg ttcatcacca gaagggaagg   11220
ggctggaaat gaggtcactg catcccagcc cagggctcct gggtcatcca ggaagggaag   11280
aaggagcaag ctttctcatt gttaggtagg agctcagagc catcacaaga acaagttagc   11340
accatccctg tgccctccct gttctgcaaa caaaatgatc ttccttcttg ccctggcact   11400
agagtctgtc tggcatttct cctgccccta gtactcctcc catctgggta cttcttcccg   11460
ttggtgtact gaacaaacac atccactgct ttattcacag cctccagccc tcattttcca   11520
gggcccacac catttgtttt tactaacccg acaaggttgc ccactgtccc cagtaaggtt   11580
tgtactgggg ttttactcc agtgctcttc tccatccagg agacctttgg atacttgggg    11640
aagaaaatga gcttaaattc ccaccctcc ccctttacct ttttcctgta aggccctggc     11700
cttagttctt agcccacat ccttgctggc tgcagaatag cagcgggttc tgggtaagga    11760
gcattctgct aaaacgctcc accctgctcc ctcatctgtc ctctccattt gtccccatca   11820
gatggtttaa gtgcttaagg ggactccagg gcggagtcag ggagaaccct ggctctcctg   11880
ggctaggcac aagatcattc tacaggaaac cttgtgggaa ttcttctggg acaaagtatt   11940
ggtcagcgct gagcttagct gtgtctgtga cactcgcatt ctaactaggg cctatctgac   12000
gtcaacagga agtaaggctg atgcagtggg gccaagggag tctgggagaa gaaagtcggt   12060
tcagagccct ggctgccctg tcccacactc caccctccg gcaagaatcc agtccctaga    12120
tgaggtgggg agtgagtggt cgagttaaaa atctctgggt cgggtacgat ggttcacgcc   12180
tgtaatccca gcactttggg aggtgaaggc aggcggatca cttgaggtca ggagttcaag   12240
accaacctgg ccaatgtggt gaaatcccat ctctactaaa aatacaaaaa ttagccgggt   12300
gttgttgtgg cacgcgcctg tagtcccagc tactcgggag tctgaggcag gagaatcgct   12360
tgaacccagg aggcagaact tgcagtgagc caagatccag ccactgcact acagcctggg   12420
cgacagagtg aggcttcgtc tcaaaaaaaa aaaaaatctt tgggccaaat ctccagacag   12480
cacaggcagg tgcagaaacc caccaggaag ctgcctgtgt acctctggca gattggagcc   12540
tggcctaaag ctgccttta tgcagcttgg gtcaaggtta aacatcatgt cacagtgatt     12600
tttctcacta tgtgtgagac atggagaact ggctccaagt actactctgt ccactggtgg   12660
ctggactact gatgtgcacc actctccact cctctcaccc tgcagtgggt catggccccg   12720
tgccggggca gaggagaaaa atgggctgcc ttctccagga caaaccctca ctccaactca   12780
actagggtgc tgtgatcaga atgtgcaatt gaggtgtgat tttactgatt tttttttttt   12840
ttgagaccga gtttcgctct tgttgcccag gctggagtgc gatggcacga tctcagttca   12900
ctgcaacctc cacctcccga gtttgagcaa ttcctgtgcc tcagcctcct aagtagctgg   12960
gattacaggc atgtgccacc acgcctggct aattttgtat ttttagtaga cggggtttt    13020
ctccatgttg gtcaggctgg tctcaaactc ctgacctcag gtgatccacc cgcctcggcc   13080
tcccaaagtg ctagaattac aggcgtgagc caacgtgccc agcctgtttt tgttttttgt   13140
gttttgaagc agggtctcac tcagttcccc aggctggagt gcagtgacac gataatagct   13200
```

```
tactgtagct gcaatctccc gggctcaaac gatcctccca cctcagcctc ctgaacagtt   13260
gggactacag gcacaccacc acacctggct aattttttt tttctttttt tagtagagat    13320
gaggtcttgc tatgttgccc aagctggtct caaactcctg aggatcaagt gatcctccta   13380
ccttagcctc ccaaaatgct gggattgcag atgtgagcca ccacccag cctgattta     13440 ctttaaatga gagtccctct tcagagtccc tcagctgttc ctggcccctg gccatgtgcc   13500
ttcagttgcc cctgcttctg tggtatcctt aaggctacat tcagtgctga ggccctaggc   13560
aggcagcaga gagaagccaa atgattctgt cttcccctta tccacccaga gcatgcaaaa   13620
ccaggagcag tggtgggttc agggtgggca ccagctatgt atatgtacat cagggacagg   13680
gggccaaagg cagtcagttt ccaaagactg ccccagaggc cattttttcag agaagccctg  13740 ggttcctcaa gggccctgtg tccatgctgg cccatcttgc aggacgagcc tgtgagtgg    13800 gagacacctg acctttctca agctgagatt gagcagaaga tcaaggagta caatgcccag   13860
atcaacagca acctcttcat gagcttggtg agttgactgc tcaggaaggg ggcgtgggga   13920
ggagcaggta cccagctatg tgcctgatac tcagagggtc acaactgagg ttatcttggg   13980
tgggcgcaag cagtaatttg tgcatacccca gcctagcccc aagtagactg acatctcacc   14040
tggaacctat tatcaaggtt tggtttctct atttctttag aacaaggacg gttcttacac   14100
aggcttcatc aaggttcagc tgaagctggt gcgccctgtc tctgtgccct ccagcaagaa   14160
gccaccctcc ttgcaggatg cccggcgggg cccaggacgg ggcacaagtg tcaggcgccg   14220
cacttccttt tacctgccca aggatgctgt caagcacctg catgtgctgt cacgcacaag   14280
ggcacgtgaa gtcattgagg ccctgctgcg aaagttcttg gtggtggatg accccgcaa    14340 gtttgcactc tttgagcgcg ctgagcgtca cggccaaggt gggcttccca ccccacctg    14400 ccctatgtga gggtatatac gcatgcacct gagcatgcag gggctgagca gctggccctg   14460
tctctgatca ttacttcccc ttcacagtgt acttgcggaa gctgttggat gatgagcagc   14520
ccctgcggct gcggctcctg gcagggccca gtgacaaggc cctgagcttt gtcctgaagg   14580
aaaatgactc tggggaggtg aacgtgagta catagttctt agtttcttgg ttgtcactag   14640
acaggactga tgggctgtag ctacagtaag gcttggagga ggaattgtgc tggaagacaa   14700
gccctgcaaa acagttccag gagtgtatag gcattgtaac taaagcaaag gcttccagac   14760
cactcatgcc aaagcctagg gttgtcccaa gaagccagga agaattgcct tggtgctttg   14820
atctttcctg gtgtggaaaa tcttctggag atgcaggagt ccatctaatg acatgaggag   14880
gcccccttca gactttttac ctggaagctt tctggctcca aggtattagg cctgtgggagt  14940 gaaattagac tcagaatatg cctgacctgt ccacaggtaa ttggggaaca tctgacttgg   15000
ttgtctcagt aaggtgaccg ttttgtaggg cccatcttcc atacaaactg ctgtcaggga   15060
tcctaccaga gatcattcag ccaagagcct gacatcagaa agcccagtcc tagcttgtgt   15120
gaacatgagg tgctagtctt ctctggggag ggtctgctgg cttggccatc ccttctgcag   15180
cctgtacact ccccttttgc cccttgcagt gggacgcctt cagcatgcct gaactacata   15240
acttcctacg tatcctgcag cgggaggagg aggagcacct ccgccagatc ctgcagaagt   15300
actcctattg ccgccagaag atccaagagg ccctgcacgc ctgccccctt gggtgacctc   15360
ttgtaccccc aggtggaagg cagacagcag gcagcgccaa gtgcgtgccg tgtgagtgtg   15420
acagggccag tggggcctgt ggaatgagtg tgcatggagg ccctcctgtg ctgggggaat   15480
gagcccagag aacagcgaag tagcttgctc cctgtgtcca cctgtgggtg tagccaggta   15540
```

```
tggctctgca ccccctctgcc ctcattactg ggccttagtg ggccagggct gccctgagaa   15600
gctgctccag gcctgcagca ggagtggtgc agacagaagt ctcctcaatt tttgtctcag   15660
aagtgaaaat cttggagacc ctgcaaacag aacagggtca tgtttgcagg ggtgacggcc   15720
ctcatctatg aggaaaggtt ttggatcttg aatgtggtct caggatatcc ttatcagagc   15780
taagggtggg tgctcagaat aaggcaggca ttgaggaaga gtcttggttt ctctctacag   15840
tgccaactcc tcacacaccc tgaggtcagg gagtgctggc tcacagtaca gcatgtgcct   15900
taatgcttca tatgaggagg atgtccctgg gccagggtct gtgtgaatgt gggcactggc   15960
ccaggttcat accttatttg ctaatcaaag ccagggtctc tccctcaggt gttttttatg   16020
aagtgcgtga atgtatgtaa tgtgtggtgg cctcagctga atgcctcctg tggggaaagg   16080
ggttggggtg acagtcatca tcagggcctg gggcctgaga gaattggctc aataaagatt   16140
tcaagatcct cctgctgttg gaatctttta tacatataaa gttttttgtag agacatgagt   16200 ctctctgtgt tgcccaggat cctcccaact tggcctccca aagtgttggg attacaggtg   16260
tgagccaccc tgcccagcct ggactcttta ttattatagg cgcagagctg cagttgcccc   16320
tcatggtgcc agaagttgcc aagggtgatg acaggctcc caggtgtctt gcaaagtcac    16380 catgaccaa tttgtgaaga tgtagtatgc atacatactt ggtcatcact cagctccctg     16440
gggctcaggt tgtggtggag acaaaaatgg actgcagtta gaacttaggg aaactggctg   16500
ggcatagtgg ctcacacctg taatcccaac actttggttg ggctaggtgg gcagatcact   16560
tgaggccagg agttcgaggc cagcctggcc agcatggcga accccatct ctaccaaaaa     16620 tacaaaaaaa atttagctgg gcgtggtggt gggcgcttgt agtcccagct actcagaagg   16680
ctgaggcagg agaatcgctt gaacccggca ggcagaggtt gcagtgagtg gagatcacac   16740
cactgcactc cgatagagca agactccaac tcaaaaaaaa aaaaaacggc cgggcgcagt   16800
ggctcaggcc tgtaatccca gcactttggg aggccaaggc gggtggatca cctgaggtcc   16860
ggagttcaag actgcctgac caacatggtg aaaccccgtc tctactagaa atacaaaaaa   16920
attagccggc atggtggcag atgcctgtaa tcccaagtac tcgggaggct gaggcaggag   16980
aatcgcttga ccctggagg cagaggctgc agtgagccga gatcgtgcca ctgcacatta    17040
tcctgggcga caagagtgaa actccatctc aaaaaaaaaa aaaacaaaa ccatcccttc      17100 aacacacaca caccacgctc tgggagaagg tgtggcataa ctccttcacc aaatacagag   17160
ctgccaccgt ggaccagaca ctgctcgtga taccgagggt atagctgtta acaattcttg   17220 cttcattaa gcatggactc tgctgggttt gaaaacactg aattcgaagt tcttcagaac     17280
tgaatgtaac tatgtgaatc tggccagttc cttaattttc tttcaacttg gttagttcac    17340
ataagcgtgg caatcgcaaa aatacagctg tgaaaataga agccagatgg gcacccggcg   17400
gtctggcctt aggccctgaa gtgcaggttt gaggattggt gcttgcgaag tcctgctagg   17460
cctgaactca ggtgttgggg gacgtcagag ccgccaaata cacccaaaag accgggagga   17520
ctcacggcca ccactttcct cggtgggagc tgtcccagct ggtcagatcg cgcttgctgg   17580
gacctgggat ctcgcaacgc atgctgggat gcccagcatc taagggcgcc cattggtccc   17640
gcccccacga cttgagcaac agccaatcag aggtggcagc gtgcggaagc ggaagtgagg   17700
tttccgtgga gacagccgag cctgcggaag gcggcggcgg cggcacctgc gatcagcggc   17760
tggggcaggt tatggtagtg cggactgcgg tgtgagcaga gcggccacgg ggcccgccat   17820
gcgccggcgc ccctgacatg ggcgccacgc ggtccaaagc tcggggcctg tggcccttcg    17880
cctcggcggc cggaggcggc ggctcagagg cagcaggagc tgagcaagct ttggtgcggc   17940
```

```
ctcggggccg agctgtgccc cccttcgtat tcacgcgccg cgggtaaggg catgggttcc    18000 acccctggcgg ggggaacagg cgggcggcca ggcgtcccgc gccacggggg aacttccacc    18060
gctgtacccc actacagcca agccaggacg accccccatat tttgagcctc attggagctg    18120
ggggtggaga aagccgggca gtggtctcct g                                    18151
```

<210> SEQ ID NO 14
<211> LENGTH: 20911
<212> TYPE: DNA
<213> ORGANISM: Homo sapiens
<220> FEATURE:
<223> OTHER INFORMATION: TBX3

<400> SEQUENCE: 14

```
agggatctcc aggctgtcat ggttgctggg aaagatgagg gagggaaagg gggcagagta      60
cggaggcacc aggtcagaaa gacaggagag aattcagaca ggaccaaaac agccagaaaa     120
aataggataa agaaggtaga aaaaaaaaaa aaacaaaaca aaacatgaga agttaaagcc     180
tgggaaatag atacaagaca agaaagagaa atagaaacca agaacaagat tgatgaaagg     240
aggagaagag aaagtagaag gaaaaagaat aagaaagatt ccagacacgc attcaaataa     300
tcctaaatgg ggatgagcag aaagacaagg agaccaaaag aaaaggggg ggggggtgg      360 tggggaggag aaagaaagga atggaaaaag aaacaaaagg tgaatgtcct gccctgtctg     420
tctggtccaa ccaagaagct agtgtctgcc ctggagggag gaaaggtggg ggagtccagc     480
ctgtctccaa gggactgaca gcagcttct ggaccagaga ggaactaagc tctcaaagca     540
agctttgggg aggaggaagg gatgggggtg catggtgagt ggagactcct ggaggaagag     600
caagcctcca ctgggttcag cactgccagg gggagagtca gggttcaggg tagcatagca     660
gtgctaatgt atgtacccca gaggggtagg gggtgctagg gcaatttgca ggaggaccac     720
aaacagtaaa ctagagagct acttccctgg gatccgtgat aagaaaatca cttcctcagg     780
tgggagaatt gagcccgaaa gagaatggga gcccttgggg ggcaggcacc tggtcagttt     840
caaagctcgt caatatcaaa agaggctggg atcctgagat caaatgggct ggggcactgg     900
gcagaaacga ggagccattg ccaaactgcc aggatgacca gaacgcccct cccccaggaa     960
aagttcatat atgaacccac ccctgtatga aacttcttaa ttaggtctca tacccccggt    1020
gaatcttgga tgcccttctg tcaacagaat tcccaattta gtgacacctc ggactgaaaa    1080
gagctctgcg gcaaacgggg gtgaaagttt aagagggaat aagcatataa tactcccttg    1140
ccagacctca cacatgctga agggaatatt tacagcaaac tggccaaagc aaacgacccc    1200
gcctacccac catccttta ccctcctccc cgcccttttt gtaaactcca gataaacacc    1260
atttgatcac aaaagggtcg gtttgtcccc tttatagttt gaggcaggca gtgcggcagg    1320
gaaaagtggc gtgggctaag cttccgtctc gggcaaggcc agcttctttg ctggcaccgt    1380
ggcctgggct aaggacagtt gatttggttt tgtttccccc gacccccacc ccgaccccac    1440
ccccacaaag gaacattatt ttcagggtcc tcccccacc cagctttaac actcgcctac    1500
ttgcacccgc actactttaa atgctgcggg cattgcagat agagaggttt ttcagttaat    1560
ttactttttt aattctagag ctacaattaa gtgaaaactc ttttttgcgaa aaggtggagg    1620 aatatttcag agacgccaga aattatctgg gtcttttctg acccggaatc tgccctcttt    1680
ctcccttctc ctccccttaa gtcacccttt tctgggactc tgttgaaggg caggctcttt    1740
caacgtctct agtctgtctt ttgttgagtg tgagaccgaa ggaaagagga tcgaggggtc    1800
```

-continued

```
tgcagagaga aaaagaccgc agatagccgg cagctggcgc ctaatgccgg ggtccgggga      1860
gcgctggcct cgtgggttct cctggaggcc aggcccagca caagccttcg gaacacgctg      1920
gccaatgttt aacccgaatg cagtggccac caggccgctt ttgtttgttc gcaaattaat      1980
cacccagcgc atggccggcg ccagagtggg tttatcaccc accgggaggg gggcgcgccg      2040
ggcacgcaga gacaaagagg agttcgcacc ttcccgcttt tgatcccaga attacggcgg      2100
cctccctgcc taatacgagc ctcctgggggc cgagtctggg aggtcagtca taattggcgg     2160
aagtttgcag accattagca agatgtcgac attttcgatt cgaaccccgc aaactttcct      2220
ctcgttctct gcttcgcgcg ctggaggttg gtgtgggaga ggagatgggg gtcagaagta      2280
gcgatctggg gtgatcacag ggttaagtta gagctatggg caaaaaatag gcaattgagg      2340
gaggaggaca gtgtgagggg cagaactccc tctcagtcca cccgcggagc caaaaacaaa      2400
tctagacatt tttaagtaaa atccgcaagc tcccctccca tttccaaagc tgacagctgg      2460
ccagaatgca gaggaatgtc tctctgctgt gcgtgggacg cttgggggca ccgagtgggt      2520
gaggaggagg tcggtcacag tgtggttgta gaactacttt gcttccaccc caagtagtgg      2580
ggcagagatt ggcctgcgag ggcaggcagg caaaaccaga tcgctgggat ttggggccgc      2640
tcttgaaaga gcagcgaagg ggccccaggc cccggaggcg agcagtctgg gggaggggggt     2700 gcacttttttt tttctatttc ttctttttct tttcttttttc ttttttttgg ggcggggggtc   2760 cccagagact catgaaaccc tgcagtgact tccgtgttct gtgtaaggcg ggaaatggcc      2820
tggcctttcg cacccttcag gtggggagga ggggatgcgg gaggggggtgt tatgagccaa     2880 cactctgggg caccaccacc tcgtaatttt ccctctctct cctttctcta ttttaaccac      2940
tggcagagac agagaggacg ccagagaaag acagactgaa agggaaagaa aggggcgaga      3000
tggcgagcca gacggagttc gcagaaccac actattctct ctggtgactt cagggaattc      3060
tcaacgctgg cgccaagctc tcttaaccat gtgcgtcaaa aatgcgaggc tggagaagcc      3120
tgtcgcctca aaagatcctc ccctatctca gcgtggttgg cccacaagag cacttcattt      3180
tcacccttcc cttggtgcca cgttggggtt tcggggttgc tggggggttgc gcgggtgcac    3240 aaggcaaaat gcgagagagg cctgtgctgg cctacagaga cacacacatc caaagccctg      3300
agtctcttaa accccctaagc ccccagatca gcccttttctc cgttccctttt ccatcgaaga   3360 agctttcatc tcaggaaaga taaaagaaca ttgttttcaa gatttccctc catctaagca      3420
aggatggtcc aagacattgg ccccccagaat caagaactgt gggcttaggc gaatcctctg     3480
accccgaccg ggcgctgcgg taacagagtt ggtaattcgg cgattggtaa gatccggtcg      3540
tttccctccc gtccgcctaa gaggaggccc ccaccctacc cgtactaaaa acagtcaact      3600
cgcctctgag gtggggggcgt ttcacggttt gttttacaaa ttcaccctcc ctccccgact    3660
tctggccaga ttaagtcccc ggggtggaga aagaactgag gcaccgagag ataagtgcga      3720
tgcctagaga agataccagg ctggcgcgcc tcccccaacc caatcgccca ccccttaccc      3780
tgtgctgtgc acccagccgg gcctcgaggt gagggcagcg gcttggaggg gacaggctca      3840
gaacccagtc tctcgctgtg ctcgctttgt ccagatcctc cattctcttc tctacaccca      3900
cacccacatc caggtggaat atgggggccc gcatgcaaat gaaagacgag atccaaaagg      3960
gctggtaaat gcatttcata aaaatcccaa atccatcttc cccaggagct caggcagggc      4020
cagccgcgca ggctgtgtac gtgtttgtgt gtacgtgttt ttcggtgtgt gtttcagtcc      4080
cagtgtgttg gcgcgtgttc gagtacagat acaccggggg tgtttgggta cccgcacatg      4140
gctgcgggtg gggcgcagtg gagaggaagc ccacacatgc gtgtgctgag atatggccgc      4200
```

```
atccttgtgc tcccccagcc cagacgcagg ggagaccagc accgagacac ccgagctcgg    4260
gagcccttca gcggcggccg ggcggagctt ggctccacgt ggggctggag agcacgcaag    4320
cctggagtct cggcgctcgc ttctcggctg ccgccggctt ttgtagaacc gagtggccgg    4380
atggcagctc gcggggaggc tcggccaccc gcccggctcg cccggggcgg ggagaagaag    4440
gagagctgga gagagaaccg gccgcggcgg tcggagaggc gagcggagtg caagagaggc    4500
gagcgcccct gcccggcgcc cgggcgcgct tccgccttc cccgcccggc tcgcctgctc     4560
gctggctccc tccctctctc cctccccctt cctccttggc cctgcctcct ccctcgatcc    4620
ccggctggat gactgaggca tttcagacgt gggctgaacc agagcgagcg agcgagctca    4680
ggggctgcag cgatctctcg ataagccacc tagaggcgac tctgtgcgcg cgcgctcccc    4740
agtggctccc gcccgccctc tgatcatgtt gacatattca caggacaggc agtagtaccg    4800
atgcggcgct gcgacgttac agtttccgac accttctttt tataactcag ctctatcccc    4860
cagcactcga cctgtgaaaa ccacgccat gcagcaacac aattggtccg aaagcgtcaa     4920
agagccaatc aagaggcctc cggctccccg cagcccacag cgcagcccga ccttctagag    4980
ccgccgagca gacgcccggt gaattctaga ggcggcggag ggtggcgagg agctctcgct    5040
ttctctcgct ccctccctct ccgactccgt ctctctctct ctctctctct ctcccctccc    5100
tctctttccc tctgttccat tttttccccc tctaaatcct ccctgccctg cgcgcctgga    5160
cacagattta ggaagcgaat tcgctcacgt tttaggacaa ggaagagaga gaggcacggg    5220
agaagagccc agcaagattt ggattgaaac cgagacaccc tccggaggct cggagcagag    5280
gaaggaggag gagggcggcg aacggaagcc agtttgcaat tcaagttttg atagcgctgg    5340
tagaaggggg tttaaatcag atttttttttt ttttaaagga gagagacttt ttccgctctc    5400
tcgctcccctg ttaaagccgg gtctagcaca gctgcagacg ccaccagcga gaaagaggga    5460
gaggaagaca gataggggc gggggaagaa gaaaaagaaa ggtaaaaagt cttctaggag     5520
aaccttcac atttgcaaca aaagaccag gggctggaga gagattcctg ggacgcaggg     5580
ctggagtgtc tatttcgagc tcagcggcag ggctcgggcg cgagtcgaga ccctgctcgc    5640
tcctctcgct tctgaaaccg acgttcagga gcggcttttt aaaaacgcaa ggcacaagga    5700
cggtcacccg cgcgactatg tttgctgatt tttcgccttg ccctctttaa aagcggcctc    5760
ccattctcca aaagacactt cccctcctcc ctttgaagtg cattagttgt gatttctgcc    5820
tccttttctt ttttctttct tttttgtttt gcttttctccc cccttttgaa ttatgtgctg   5880
ctgttaaaca acaacaaaaa aacaacaaaa cacagcagct gcggacttgt ccccggctgg    5940
agcccagcgc cccgcctgga gtggatgagc ctctccatga gagatccggt cattcctggg    6000
acaagcatgg cctaccatcc gttcctacct caccgggcgc cggacttcgc catgagcgcg    6060
gtgctgggtc accagccgcc gttcttcccc gcgctgacgc tgcctcccaa cggcgcggcg    6120
gcgctctcgc tgccgggcgc cctggccaag ccgatcatgg atcaattggt ggggcggcc    6180
gagaccggca tcccgttctc ctccctgggg ccccaggcgc atctgaggcc tttgaagacc    6240
atggagcccg aagaagaggt ggaggacgac cccaaggtgc acctggaggc taaagaactt    6300
tgggatcagt tcacaagcg gggcaccgag atggtcatta ccaagtcggg aaggtaagca    6360
gtggggggcct cctcccctaa gctgttggag agttttttcc tcccttattt tctctgctcc    6420
cagaacagtc ggttggtcgg ttattacggc ttggacgaaa agttagttcc cctagaaatg    6480
tatgcacaga cttccaggcc ctgccccggt ggcaggaaat ttcagcttac ctgggcatct    6540
```

```
gcatgggtct tgcatttggt ctgcatcctg ggttccctcc cgaacagaca gaattttttca   6600 gtggagcaca gacatccctg cagggagcag gaaagaaaaa aaaaaaaggc actctactgc   6660
aagaaactca ctcttcaaac cctcctggaa catccttatt tctttgttga tgttgtgttg   6720
tctgttttat tttgttctca gagagaaaaa cttaaagccc ttttccttttg tgtgggtatt   6780 gggaggcctg acaccattcc ccggcccttt ctgccctcca gtctagcctc tgggtctaaa   6840
ggggcctgct gctgccctgg tcagagagaa atcgaagggc attttggttt gtttgcccac   6900
actacttcac gtgtctgtaa cccaagggcg agttcagcag gcaattttgc ataatttaag   6960
attatgtttg cagacttaag gagccagtga ggagacacac accttttttt taatgtgtga   7020
atattatcaa ccatattta cataatgttt aaaggtcctt gcctgaccaa aacctgcctg   7080
gaagagaaga tcctgtaata gtcatttaaa atcactgatt tttttttgt aatagcattg   7140 aagcctgtaa aggcataaag ttgatacaaa ataaaatcc ccttcatgat atcttaagcg   7200
ttctgtctcc ttccaagcta aatgaggcca agtttggca taaatcctc ctcaaactca   7260 caagacattt agtcagtttt ccagcaaagt gcttccttgc ttccttttaa gtcaagacta   7320
cagaatgcca acccttctgt gaaattaaca gcaatgtggt ggcacagtct tgcggttttg   7380
gactggccta agaagtgggg gaatgtgtta gcagctccac gggcagatcg gttatcaggc   7440
ccaggagtgc accgaagtct gcaaaattcg ttctgggaac tcactgaagt ccagtttcac   7500
ttcgcccaca gcgggattgc tattctgcag cagggagggg tgcaacttga cgttcatttc   7560
cttgataagt ttaacatttt ctcatcaatg ggtggtggaa aattctagtc ttaactgacc   7620
gcgctttaca aaaatcttac cccaacctgt ttagatctag atacccacag aaaaagacat   7680
gggcaagaat ttgctctcag gagggcaatc tgtaaagtca agcaaggaca aaaaaaatat   7740
tgaagaaatt gttagacaat gtagagaatt gcagtgccac aatgcatttg ttttgaacct   7800
tgggacgtct aaatatggcg aaactgagaa tatttaatac gttagttgtg gaagaaaacg   7860
attttgcaac cagttgcctc actctgaaac atgtaagctt atcagtcaca atataaagtc   7920
ttagacttgg tttcaatatt atgtgataca taggaaatca aacccaagat tacgggtggt   7980 ttatcttttct ttttctttttc tattctttcg ttttataggc gaatgttttcc tccatttaaa   8040 gtgagatgtt ctgggctgga taaaaaagcc aaatacattt tattgatgga cattatagct   8100
gctgatgact gtcgttataa atttcacaat tctcggtgga tggtggctgg taaggccgac   8160
cccgaaatgc caaagaggat gtacattcac ccggacagcc ccgctactgg ggaacagtgg   8220
atgtccaaag tcgtcacttt ccacaaactg aaactcacca acaacatttc agacaaacat   8280
ggatttgtaa gtttcattgc tctcttcagt aaaattttct cctccttcac tcagtcaaag   8340
gcagtgcttc ccatttcatg agtttcagcc cagacttctc ctttgcttct ccctaagcat   8400
agcaaacttg tcctcgtctg gaaaaaggat tcggggtgtt tctctccaaa taatggaagg   8460
cctggcgttc taaagaaat ggggcaagaa aacttaccgg cttgtgttct atagcaattc   8520
cagctctttg gtagattcct gacctgagag tgaagttaaa aaccatttttt taagagctaa   8580 aatcaatttc aaggctatgt attcctaaag gatttgtttt gttttaaaat atcatacttc   8640
tgttttgaaa ccagtgatat tattttctca ggagagttta cgtttcggag ccttgactct   8700
gttggttaaa tggtgtgaat acatttttaa aaactcgttc ttttactaaa aaagaattg    8760 ggcttaggtg gggagtccggc ttaccctaaa tgaggcttag atcttcagaa aaaatggtt   8820 tgtgtgttgg gagtgtatat atggattcag tgacagtgct tagaaactta gaaactttc    8880 attgcttgta gatatcaggc aaaggacctt ttgcgccttt tcctaccct cccaacatt     8940
```

```
tcaataaaat aaacagcgtg ataagcaagg agtaagcaga aagattaggc ccaggaagac   9000
gcgaatggcg cggaaatatc ttcagcgggc aggaattgca tttgaagccc ttgatttgat   9060
taaggcataa atattcctct ctagagttca gcctttcagg gctttaagtg gattgggctc   9120
gtcaattagt gggcgcttaa agtactgaat cattttgtaa attaaaatgc atgttttctc   9180
ctatctttta agactttggc cttcccaagt gatcacgcta cgtggcaggg gaattatagt   9240
tttggtactc aggtaggcta gggttcaagg tatgaatgat ccttagatgg tgagggtggg   9300
gggggcccct tggcaactga ggagcaattt ggattctcca aagataaca tctgtggagc   9360 gaaacgtacc caggggggta tccaaggagg tgggctcggt acaagcgtgg taccctgcgg   9420
tggggaagat ttcagcctgg caggggtcct aagatcccgt tgttctgct aaatccttgt   9480 tttatgtatg tctcctcttc cctgcccctg cagactatat tgaactccat gcacaaatac   9540
cagccccggt tccacattgt aagagccaat gacatcttga aactcccta tagtacattt   9600 cggacatact tgttccccga aactgaattc atcgctgtga ctgcatacca gaatgataag   9660
gtaaactcaa ggggctttcc tttttaatgg tgatattttg ccttcccctt aaaagctgct   9720
ttaagtcagg atgagaaagt tacaagagag tggagacgag agtcttgagt tgtcttttgt   9780
gatttgtgga gcatttgggg ggaaaggaca atgacacctc gaggagacag aaaaacacct   9840
tgactaggta ggaacaatgc tgagcaaaaa aacgccatac taattttgcc acagagaaac   9900
tcctagaact gctgtcattg atgccaccca ctcctccccc cctcttgggc tttgtcctgt   9960
ctgttttaag gttcatcttc ttcccccttgg ggaagaagga tcaagaagtc acattcaaaa  10020
ggaaccagct aaaaatttaa ggcaaaagcc atttgggatc ctgggaggag aatcctagta  10080
gagaccagct tttctcccct agccagaaat cctgagtagc tggtctggtt tttattacct  10140
tttatgctgc tgtgttatga tgtgtgtgtg tgtgtgcatg tgtgtgcatg catgcgtgtg  10200
gttgaaaaaa cctaccctga tcacagggtc atattaatcg agttgtctga ggcttttgag  10260 ttgggtggc caaagtcacc acttcatttg aattcccccc ctccccaggg cctgaatctg  10320
gaggttagaa ggatccccaa aagggaaagc acctgatatc tagagctatg gtggcctgaa  10380
ggtcatgggc acagaaaaag tgaccctac tgctgattca ccagttccca gattggctgt  10440
tagcagttat ggggtgggag gagggactga agaccctgc tctgcaatcc tggacttcaa  10500
agagagtcca ttttacctga caacacactt catttgaac tcactgtcat tgtcactgtc  10560
cttgggtcct ctgtggactt catgatgggg atgttccagc taaatttctt tagtgtgaat  10620
accaaaacat gatcttctct ccctgtgaaa cctgaagtct tcaatagagc aatttattcc  10680
aagaacatga atccaaccaa gggtccccct ttccacctct gagtaactct gtgtatataa  10740
cttcttcttc ccaccaaggg gaagggattt gaaagattac acactatagc attttttctca  10800 aagtgcaaaa tgcatgtgcc ctctagaccc agaatcctgt gaaatgaagt tgttaatgta  10860
ataataaaat gtagcatttt tgatcagaca aaaaggccat gggccttctc cacctaatgg  10920
ccatggcaga gcatataaat gaaaacagat gtttccagtg gtcattcagt actgtaactg  10980
tcaatattgt aatttcctca aaccacccc caggcaaaga aaaaaaaat taaactcact  11040 cccgcactca ctcccgcaca agggtagtga aaccccataa atcatttatt ggattcatgg  11100
aaaaggagtg tgtgtgtgtg tgtgtgtgtg tgtgtgtgtg tgtgaaggga gtatgctata  11160
atttatgatt aattgcactg tataaaaatc aaaatgaaag cataatttta agatctacag  11220
gttttccctc ttgatgactt tgacaacact tccatgtcta aacccaaact gttggctgcc  11280
```

```
caaagaaaag aatttctttg aataatttca tccccaaatc cctggtttgg cctcatatag    11340
gagatacaag ccctgccaca gtttccttat tatctccttt ccctggcata tctatatgac    11400
ttctgttggc agtcacatct ctagacttgt tgagttggga aaaacaccct caaaacattc    11460
tagaaaatga gaacaatgtc tctgtcttgc ttgtgtctct tccaatagat aacccagtta    11520
aaaatagaca acaacccttt tgcaaaaggt ttccgggaca ctggaaatgg ccgaagagaa    11580
aaaaggtgag ttgaaacaat tatttattag atagtttaga aaaatcccct tttttaggat    11640
ccaactctga agtgttagaa gtgagatgca ggcacttatc ctaagagcgg gtggaaatca    11700
ttcactttcc ccactgctac atgcttgccg ctatcagtat acccaggaca agtactttc    11760 ctacctcctt acctttaagg aaattaacta ggctacacca tacttatctc tggaagagaa    11820
gcatcaggga taatagatta tacagggatg cctattaatt cctaattaat ttaagttcat    11880
cctaggcagg tcccagaaag aaccatgcca ttgagaaaat acttgggaat ttttgcaatc    11940
ctgtcttcca aataccatca gacagagctg gggacttcgg aaagatgtat ggctctctcc    12000
ctccttcgtg gggacatgta tcattttgca ttacgtagac agctggagag tatatgaaag    12060
agggtctccc ctcccccacc cccttttcaaa gaatttctaa aatccagaaa atcaccccca    12120 aattttttaac ctatccccctt ggggcgggca ttaaaaaata attgctaaca gctaaatata    12180
tttttattcc aattaatttg ttagtaaaac gattacagta aagtgcagca tgaaataacc    12240
acttcctccc aatcttagcc accatccaaa atttgggtat gctggggaca gacagcgttg    12300
tgtttgcagg attggacacc cggttctccc tatataaggc tggcagtcca gctgtctctg    12360
actagatcca gcctcttctc ctgcttttaa ataaaatttc acagcccaag caaatgcctt    12420
ttcctaatga aaccccatct tgaataaatg caactgaagc ctccttcctt tctccctaac    12480
cctctgccac actcttcagc ccagttagag ggtcaaggac aaagcttggg tctatgtggc    12540
tgccctgggg caagcagatt tcagtgaatt agcgttgtcc ctgggcagca ggcagggtgt    12600
gaggtatgtg tgtgccgctt tggaaagggt aagggaaaca aagaggggaa atgtatgtta    12660
cattctgtaa cctgggtgtg ggcttctgcc acagaaaaca gctcaccctg cagtccatga    12720
gggtgtttga tgaaagacac aaaaaggaga atggggacctc tgatgagtcc tccagtgaac    12780
aagcagcttt caactgcttc gcccaggctt cttctccagc cgcctccact gtagggacat    12840
cgaacctcaa aggtaaaacca tgtcaccttt gtgatcactg gactccagtc cctcgtggcc    12900
tggaagagtt gaaggggat ggggcaccaa ccagggcact tgccctttaa aagctagaag    12960
ccttctaaac atccttaaac agaagccaga gttcaaaaag ggctatcagg tgtgtctccc    13020
cttccccgct aaggcagtag aaggagagca cagaggcctt tctcccagat ccttatttgg    13080
ctggtgggga gggaggtgg gtgtctgttt gcatactacc tcttggcaag cagctttgaa    13140
aacttgcttg aagcgcttct ctctttttctc tctgtctctg tttctttctc ctcccattct    13200
ctccaaccaa cagaggctcc aactgctgac ttttcactgt ctttgaactc taggttacaa    13260
tgtgttggac tgggtggggg ggaagcaagg gactctgcca cctggaaccg agaaggtggc    13320
ctagaaaaca tccagctata aagcaacaat tgacctggga gaggaggtgg agcactgggg    13380
atctgcggtg ggggtagagc tgggggaggt gggtgaggag tggacaagat ggctcaaatc    13440 cccctcagt tacctgtgtt taaagagcaa gcagtattta tttggaaaga cacacacaca    13500
cacacacaca cacacacaca cacacacaca ctctcaacgg gaagaaacct gttttttagt    13560
gaaataaaat gcaagtcctt tatgtcttca atccatttaa gctttaaaca taaaatagga    13620
tccctttttc ttttcttctg gtggaacacc cacagagggt gtggtaaaag cgaaaaaaga    13680
```

```
atctatgatc gtccccgggc tgtgagccat ctgtccgaca ctcatctctc tctgcaggga   13740
ctggggcaaa tacaaacggt tcaactgagt actggtgttg aaggacaggt gtccgttctg   13800
ccattatcaa ttcagatgtc agggttcttg ccaaacaaat ccttccagag taattcacaa   13860
atttgtggaa ggtgctgctc tctgtcattc actgattttt tgatagtaat tagaatatgt   13920
tccagctgtg agtttaatg ttactttta cttttaaaaa gttaatttgc aatcgaatgg     13980
ggagatgcat gtgaaatctg ccactgtagg aactcaaaaa aagaagtaaa attcattaaa   14040
ataagaagag ctactgatta ggggattgtc catctaaggg aaagtttaaa ctctgggtaa   14100
atactttaaa ttcataatcg cttattgaat tttccagcaa tgttgttggg cacgattatc   14160 cccatttttgc agatgacaac actgaggtgc agagaggcta aggggctttc cccgggatta  14220
cacagccact aagccacgag ctgggattcc aacttgggaa ctggagttcc gttggctcat   14280
actggagata acgccttct gccttggttt tttccttcgc ctgtggtaga tttatgtccc    14340
agcgagggtg agagcgacgc cgaggccgag agcaaagagg agcatggccc cgaggcctgc   14400
gacgcggcca agatctccac caccacgtcg gaggagccct gccgtgacaa gggcagcccc   14460
gcggtcaagg ctcacctttt cgctgctgag cggccccggg acagcgggcg gctggacaaa   14520
gcgtcgcccg actcacgcca tagccccgcc accatctcgt ccagcactcg cggcctgggc   14580
gcggaggagc gcaggagccc ggttcgcgag ggcacagcgc cggccaaggt ggaagaggcg   14640
cgcgcgctcc cgggcaagga ggccttcgcg ccgctcacgg tgcagacgga cgcggccgcc   14700
gcgcacctgg cccagggccc cctgcctggc ctcggcttcg ccccgggcct ggcgggccaa   14760
cagttcttca acgggcaccc gctcttcctg caccccagcc agtttgccat gggggcgcc    14820 ttctccagca tggcggccgc tggcatgggt ccctcctgg ccacggtttc tggggcctcc    14880
accggtgtct cgggcctgga ttccacggcc atggcctctg ccgctgcggc gcagggactg   14940
tccggggcgt ccgcggccac cctgcccttc cacctccagc agcacgtcct ggcctctcag   15000
gtatggatcc ttcttcctgc ctccaccagt cttttccacct ttcgtccagt ttccctgtcc   15060
tttgccagca gaccctcacc cgatcccttt ggcctagtag ctgtaataat ttttactgag   15120
ccattaccgg gttcaaggct tagctcatgg agttattatg acttcattct ccccattcac   15180
cccaaaaatc tttaaaattt ttccgaagtt aaaggctgtt tccagcagag tagataggta   15240
gtaacaaaga taacagctgg acacagcact tactttcagg cattcttcta agtgcttgct   15300
ctgtattgac tcatttgacc taaccttca ggggtactat tatcacctcc actttacaga    15360
tgaaggcgaa gacgcccaga gatgttgagt gacttgtcca aggtcacaca gcgggtacat   15420
ggtggagctg agactcaacc ccaggctatc tgactccagg gcctctttga gggtttctga   15480
ttttagcttc agagctgaca tgtctcttaa gtgtctcata gccaacccctt ccccaggaat   15540 gggactctag gcctggggag gggaagtgac tacttcctga gtaggagttc agtcttgatt   15600
cctccagcct ttcctcccag ttcgaagctc ttctccccac cccaacccc aagcaggcca    15660 gcctattcct cgaagggtta atggtttgtg cacacgtggg aaatgtcaga ggacagggat   15720
aagcagggac tggggcaggc ctggaggcct gtgtgtggct cagacagctg tgctgggggg   15780
aggtctcagg cggctggaaa caccctgaac tcgatgaaaa ggttctatga ggttttgcat   15840
gctgttgcct tttgttttgt ctgagcacat tcgtctggtc tcccttccct gcgccaagaa   15900
accagattgg cctccccact ccagggagga gggagctgag gaaaggcttg gcttctggca   15960
tttctcaatt cctcccatct cctctgctgg cttctccggg agaccctgtc ctaggtgggc   16020
```

```
aggtggttgg tacaccaagg actacctgaa cagacaaaac cttaagggca cctcaaggca    16080
tgatgcagag aactggccca ggccagggtg cctgcatctt aaatgctgct tctgccaatt    16140
cccagcttag tgcactcctg aactcctgcg gcctacctcg gcttctcacc tggaacacca    16200
gtgaatcatg ctggacgatt tctttgtctc tgtttataac aaatgccctt tttccctccc    16260
ccagccccag tttccttttg cttaagatct tcactgtctg ttttttttgt tttgttttgt    16320
tttgtttgga gaaacttcta ggattggggt gggaggatgg gggttgggga agaagaaaga    16380
tttaaaaaat tattcctact aatttatgtc ctccggcttc cccttggtta cctctgtggg    16440
gtaaactgaa tctgtatccc catttaacag gtgcaaggag atttcctggg ggctgcacac    16500
actgtgtgca gcatattgca ggctttcact catttaatat ctacaaagtc ctcaataagt    16560
atatgaatta cttatgattt ccctgttttt tcttcctata aggaagctga ggcacaagtt    16620
aatcaaagtc tcttggccta gggtgacaca gctaagattt gtacctagag atttctgagt    16680
gttgacttct ctcctgcccc cacctatctc cccccccaaa aaaaaaaaca caacaacaac    16740
aacaacagaa cataccaggg attcatggct tgcccaatgt tggaggggga gaagagagga    16800
gagggatgag ataagctcct cccacccggc tgactcgctg tgtgtctctt ttctcacccc    16860
agggcctggc catgtcccct ttcggaagcc tgttcccta cccctacacg tacatggccg    16920
cagcggcggc cgcctcctct gcggcagcct ccagctcggt gcaccgccac cccttcctca    16980
atctgaacac catgcgcccg cggctgcgct acagccccta ctccatcccg gtgccggtcc    17040
cggacggcag cagtctgctc accaccgccc tgccctccat ggcggcggcc gcggggcccc    17100
tggacggcaa agtcgccgcc ctggccgcca gcccggcctc ggtggcagtg gactcgggct    17160
ctgaactcaa cagccgctcc tccacgctct cctccagctc catgtccttg tcgcccaaac    17220
tctgcgcgga gaaagaggcg gccaccacgc aactgcagag catccagcgg ttggttagcg    17280
gcttggaagc caagccggac aggtcccgca gcgcgtcccc gtagacccgt cccagacacg    17340
tcttttcatt ccagtccagt tcaggctgcc gtgcactttg tcggatataa aataaaccac    17400
gggcccgcca tggcgttagc ccttcctttt gcagttgcgt ctgggaaggg gccccggact    17460
ccctcgagag aatgtgctag agacagcccc tgtcttcttg gcgtggttta tatgtccggg    17520
atctggatca gattctgggg gctcagaaac gtcggttgca ttgagctact gggggtagga    17580
gttccaacat ttatgtccag agcaacttcc agcaaggctg gtctgggtct ctgcccacca    17640
ggcggggagg tgttcaaaga catctccctc agtgcggatt tatatatata ttttttccttc    17700
actgtgtcaa gtggaaacaa aaacaaaatc tttcaaaaaa aaaatcggga caagtgaaca    17760
cattaacatg attctgtttg tgcagattaa aaactttata gggacttgca ttatcggttc    17820
tcaataaatt actgagcagc tttgtttggg gagggaagtc cctaccatcc ttgtttagtc    17880
tatattaaga aaatctgtgt cttttaata ttcttgtgat gttttcagag ccgctgtagg    17940
tctcttcttg catgtccaca gtaatgtatt tgtggttttt attttgaacg cttgctttta    18000
gagagaaaac aatatagccc cctaccctt tcccaatcct tgccctcaa atcagtgacc    18060
caagggaggg ggggatttaa agggaaggag tgggcaaaac acataaaatg aatttattat    18120
atctaagctc tgtagcagga ttcatgtcgt tctttgacag ttctttctct ttcctgtata    18180
tgcaataaca aggttttaaa aaataataa agaagtgaga ctattagaca aagtatttat    18240
gtaattattt gataactctt gtaaataggt ggaatatgaa tgcttggaaa attaaacttt    18300
aatttattga cattgtacat agctctgtgt aaatagaatt gcaactgtca ggttttgtgt    18360
tcttgttttc ctttagttgg gtttatttcc aggtcacaga attgctgtta acactagaaa    18420
```

```
acacacttcc tgcaccaaca ccaatacccct ttcaaaagag ttgtctgcaa cattttttgtt    18480 ttcttttta atgtccaaaa gtgggggaaa gtgctatttc ctattttcac caaaattggg       18540
gaaggagtgc cactttccag ctccacttca aattccttaa aatataactg agattgctgt      18600
ggggagggag gagggcagag gctgcggttt gactttttaa ttttttcttt gttatttgta      18660
tttgctagtc tctgatttcc tcaaaacgaa gtggaattta ctactgttgt cagtatcggt      18720
gttttgaatt ggtgcctgcc tatagagata tattcacagt tcaaaagtca ggtgctgaga      18780
gatggtttaa agacaaattc atgaaggtat attttgtgtt atagttgttg atgagttctt      18840
tggttttctg tattttttccc cctctcttta aaacatcact gaaatttcaa taaatttta      18900 ttgaaatgtc tttgggcctt gtgttaaatg ttttttctt gggaaccttt cctgaagatg       18960
gacagtcagg ggagggttta gtatcttctt gttctgagtt tacccccttc ccttcgcctt      19020
taaataatta agaccgcccc cagcgaacca aaatgagatg tcactcaagt tacaaagcta      19080
aaaacaaaag tcccttactt gagcgaaggg agccacttca atctgaaatt acttttcctt     19140
taaattaggg agcaaagcag ggagacggaa aggggcctga tgagaataca gaaagaaggg      19200
taatttcaga tactttttaag ttttaatgga aaaagactga tgtgctccct aagtcaggtt     19260
ttcccacccg aatccgacca aaagtaagct cggcaagtac gaatgttttt cgttttaagc     19320
tcgccctcag ttttgacatc aatctggcga atccaagtcg aaaataccctt cttgcaccag    19380 tgtgtttggc tcggggaaaa ggccagcaga atgcccagc agtccgagcg ggcttggcta       19440
ggcagcaacc ctccaggttg tagaagtgga caagacgcaa cgcctttcca ctcggcaacc     19500
ccccacacag cctgcagtcc ctggtgcctc aaattgaacc cggctggccc aaggcgcccc    19560
tacgaggccc catccatccc gagttgtgcg tgcaaagcgc ggccagctcc gcgaaaactt     19620
agctgtgtca cgcgagggag gagggaaatt atccccgaaa ggggaaaggt aattccaggg    19680
tgcacatttc acccctccaa cggcaaaagt caccccaggag gctgacatcc tcccctagtc   19740
tccccttcaa acccgtctcc aggctgttcg gggagttgcc ttttgaagtt caattatct    19800 ttgaaacatt caataaaaaa tgatgaggca ctgtcagtct tttggtctcc cgaccccccag  19860 cctcgcctcc gaggtgtgtg tctgttgggg ggcgggggcg gcacgggaag gttcgagggt   19920
tagtccttag cccttttctt gccctggggg ccatgacgtg aagacccagc tggagcctgc   19980
ctggcggctg cctccctccc cacccccccac ccgccacccc ctggagcccg ccagcccggc    20040
cccaagtccc tgtcaccttc aggcctcttg aatgaccgga gaggaggacg ccccctccct     20100
tccctcatcc tgtacttgga agggatcgag gtcgagacct tttggagagc ggggcaaagc   20160
cccttccatc tctggccagg cacgtgggga cccctacagc ctcctctgcg atgtctccgg    20220
gggtgggagg gaagacagac aaccagagta tgttggtgcg gagtcgcggg gggggggagg    20280
ggcggggtgc gctgcggggg tggcagggcc tgagctgaga cgggccctgg ggacctttga    20340
ggctggggct cccccgagga ctgggagatt ccaggcgcgc gctccttctg cgcagcggct    20400
acagcctgaa gggggcagct ctggatccag cgacaacgcg cggtgtccgc gcctctgaga     20460
aggtggtagt tggctggttg cgctctcccg aattggggaa aaaagaactc agcctccaaa    20520
agggaagaaa tgctttgctt ttctcttctt tctcagtcca aatttgctta cctcctccct     20580
tctctccccc cgcccccgat ttggggaccc tgctcagact tgtgtccagc ctctcttact    20640
ggcgttcctc ttttttttttt tttttttttt ttaatctcct gtgtatctca tttgtatatt   20700
gtgatgttaa tgagtaactc ctgtagcgct gatgggcggg gggtggaggg gatgaacggc    20760
```

```
tcgcagtctc tctggattttt gctgcctatt actcacctgg cgccggtcgc aatctcgccg    20820
caggctttat ggtggctgcg gccgccccag aggccactca gggcaggcgc cttcgccttt    20880
tttctgggct tcgagtgcca cctatctgtc t                                    20911
```

DETECTION OF DNA THAT ORIGINATES FROM A SPECIFIC CELL-TYPE

CROSS-REFERENCE TO RELATED APPLICATIONS

This application claims priority to European patent application 14 167 775.7 filed 9 May 2014, the entire disclosure of which is hereby incorporated herein by reference in its entirety.

SEQUENCE LISTING

The instant application contains a Sequence Listing which has been submitted electronically in ASCII format and is hereby incorporated by reference in its entirety. Said ASCII copy, created on Apr. 27, 2015, is named DFMP-113_SL.txt and is 52 kilobytes in size.

The present invention relates to methods to detect an amount of DNA that originates from cells of a given type, where the sample comprising such DNA in admixture with DNA that does not originate from such cells. Such methods are based on differential methylation, at certain regions, of the DNA that originates from the given type of cells compared to the admixed DNA. Such methods have particular application in the detection, from a biological fluid from a pregnant female, of cell free DNA that originates from a foetus or the placenta of a foetus, or the detection, from a biological fluid from an individual, of cell free DNA that originates from cells of a tumour. Accordingly, such methods have diagnostic, prognostic and/or predictive utility for detecting an increased risk of an individual suffering from or developing a medical condition such as preeclampsia or cancer, and/or to aid subsequent diagnostic, prognostic and/or predictive methods such as the detection of chromosomal trisomy in a foetus, including for twin-pregnancies. The present invention also relates to compositions, kits, computer program products and other aspects that are used in, useful for or related to the practice of such methods.

Cell-free DNA (cfDNA), especially that found in plasma or serum, has been the subject of considerable research over the past decade. Despite the original finding of circulating cell-free nucleic acids in the bloodstream being described by Mandel and Metais as early as 1948 (Mandel and Metais 1948, CR Acad Sci Paris 142:241), it took until the mid 1990s for proof that tumours shed DNA into the circulatory system (Sorenson et al 1994, Cancer Epidemiol Biomarkers Prev 3:67; Vassioukhin et al 1994, Br J Haematol 86:774), and until 1997 for the discovery of cfDNA originating from a foetus in the circulatory system of the mother (Lo et al 1997, Lancet 350:485).

Among other forms of characteristics shown by circulating cfDNA, numerous studies have described the presence of methylated circulating cfDNA in the plasma/serum and other body fluids of patients with various types of malignancy and the absence of methylated DNA in normal control patients (for review see Muller and Widschwendter 2003, Expert Rev Mol Diagn 3:443). Although other characteristics of circulating cfDNA exist and are important for diagnostic, prognostic or predictive studies (for example, sequence mutations and micro duplications/deletions), such methylation-based epigenetic characteristics have become an increasingly important source of serologic markers for diagnosis, risk assessment and even for therapy monitoring during follow-up of cancer patients.

Likewise, the use of differences in foetal cfDNA present in the maternal circulation has been the main goal for the development of non-invasive prenatal tests (NIPT). Foetal cfDNA is derived from embryonic cell degradation in maternal peripheral blood (Lo et al 2000, Clin Chem 46:1301) or from apoptotic placental cells (Smid et al 2006, Prenat Diagn 26:785). It has been demonstrated that foetal cfDNA from maternal plasma is cleared immediately (within a few hours) after pregnancy (Lo et al 1999, Am J Hum Genet 64:218). This finding is of great importance, since the presence of foetal cfDNA from previous pregnancies would otherwise interfere with the correct interpretation of subsequent pregnancies.

It is believed that 60% of tissue-specific differentially methylated regions are methylated in embryonic cells, while during the differentiation of embryonic tissues to adult tissues, they undergo de-methylation (Kawai et al 1993, Nucleic Acids Res 21:5604). Based on the evidence that foetal cfDNA in maternal plasma is of placental origin, epigenetic differences between maternal peripheral (whole) blood and placental DNA have been used to detect a hypomethylated gene sequence (maspin/SERPINB5) in maternal plasma derived from the foetus (Masuzaki et al 2004, J Med Genet 41:289; Fiori et al 2004, Hum Reprod 19:723; Chim et al 2005, Proc Natl Acad Sci USA 102:14753). Subsequently, a number of additional differential foetal methylation-based epigenetic molecular markers have been described, including the RASSF1A gene on chromosome 3, as well as a marker on chromosome 21 (Chiu et al 2007, Am J Pathol 170:941; Old et al 2007, Reprod Biomed Online 15:22; Chim et al 2008, Clin Chem 54:500) and others including T-box 3 (TBX3) (Nygren et al 2010, Clin Chem 65:10; WO 2010/033639; WO 2011/034631).

Various methodologies exist for NIPT based on the analysis of foetal cfDNA. For example, foetal sex determination using eg DYS14 (Lo et al 1997; Lancet 350:485), as well as foetal Rhesus D found in maternal circulation in pregnancies in which the mother was Rhesus D negative (Lo 1998, N Eng J Med 339:1734). Also, and of particular relevance, are those using next generation sequencing (NGS) technologies on cfDNA isolated from maternal plasma with the primary aim of detecting the most common chromosomal aneuploidies as commercially available tests (for example, those using random massively parallel sequencing: www.sequenom.com; www.lifecodexx.com; www.verinata.com). Other technologies include targeted approaches, the aim of which is to enrich specific genomic regions of interest before sequencing to reduce the number of sequence tags needed to perform a reliable statistical analysis (eg www.ariosadx.com or www.natera.com), polymorphism analysis or digital PCR (for review, see Go et al 2011, Human Reprod Update 17:372). However, regardless of the specific technology used, current applications of NIPT rely on the qualitative detection of foetal cfDNA to determine the genetic makeup of the foetus. Such an approach leads to an analytic dilemma, because test results from samples that do not contain any or sufficient foetal DNA or are contaminated with maternal cellular DNA can be misleading. The analogous issue arises in diagnostic, prognostic or predicative tests of tumour derived cfDNA from the circulatory system: the quality of the test result often is dependent on the presence of sufficient, or sufficiently pure, tumour-derived cfDNA in the total DNA from the sample.

The quantitative determination of an amount of DNA originating from such a cell type may, in itself, form a critical part of a diagnostic, prognostic or predicative test. For example, even though studies have demonstrated that the amount of foetal cfDNA released in maternal circulation increases with pregnancy progression (Lo et al 1998, Am J Hum Genet 62:768), preeclampsia, which results from abnormal trophoblast invasion, is also associated with further elevated foetal cfDNA levels in the maternal circulation. Lo et al (1999, Clin Chem 45:184) demonstrated a fivefold increase in circulating foetal DNA concentrations in the plasma of symptomatic preeclamptic women compared with control pregnant subjects, and further studies have investigated if elevated serum foetal cfDNA developed into early-onset preeclampsia (Yu et al 2013, Int J Mol Sci 14:7571), and the potential of cDNA as a marker for preeclampsia is being increasingly studied (for review, see Hahn et al 2011, Placenta 32 (Supl):S17). An increased level of circulating cfDNA and/or the level of methylation of such DNA at certain regions is also associated with other medical conditions. For example, hypermethylation of serum cfDNA was found to be common in patients suffering from oesophageal squamous cell carcinoma, and diagnostic accuracy was increased when methylation of multiple genes (RAR-beta, DAPK, CDH1, p16 and RASSF1A) were analysed in combination (Li et al 2011, Epigenetics 6:307). Elevated levels of circulating cfDNA have been reported in patients with acute dengue virus infection (Ha et al 2011, PLoS One 6 (10):e25969), in acute Puumala hantavirus infection Outinen et al 2012, PLoS One 7(2):e31455) and high cfDNA has been reported to predict fatal outcome among *Staphylococcus aureus* bacteraemia patients with intensive care unit treatment (Forsblom et al 2014, PLoS One 10; 9(2):e87741).

It is known that foetal cfDNA present in the maternal circulatory system and tumour derived circulating cfDNA is degraded. For example, studies characterising cfDNA in maternal plasma have found that the size of foetal DNA fragments were estimated to be <0.3 kb, whereas that of maternal DNA was >1 kb (Chan et al 2004, Clin Chem 50:88). Follow-up studies have demonstrated that the release of foetal DNA is due to the apoptosis of no more than three nucleosomal complexes, it has also been shown that the average foetal fragment size is 286+/−28 bp with a maximum foetal cfDNA fragment size ranging from 219 to 313 bp (Kimura et al 2011, Nagoya J Med Sci 73:129), and another study has reported that the most significant difference in the size distribution between foetal and total DNA is that foetal DNA exhibits a reduction in a 166-bp peak size and a relative prominence of the 143-bp peak; the latter likely corresponding to the trimming of a ~20-bp linker fragment from a nucleosome to its core particle of ~146 bp (Lo et al 2010, Sci Transl Med 2:61).

In cancer patients, circulating cfDNA in plasma is protein-bound (nucleosomal) DNA and has a short half-life (10 to 15 min) which is removed mainly by the liver (Elshimali et al 2013, Int J Mol Sci 14:18925). Accumulation of cfDNA in the circulation of cancer patients can result from an excessive release of DNA caused by massive cell death, inefficient removal of the dead cells, or a combination of both (Zeerleder 2006, Crit Care 10:142). It should be noted that although cancer patients requiring renal support have higher values of circulating cfDNA, the renal elimination is not the main mechanism of its clearance. The plasma levels of circulating cfDNA do not seem to be dramatically altered in chronic kidney disease, peritoneal dialysis or hemodialysis (Kirsch et al 2008, Ann NY Acad Sci 1137:135).

Although the nucleosome is a very stable protein-DNA complex, it is not static and has been shown to undergo a number of different structural re-arrangements including nucleosome sliding and DNA site exposure. Depending on the context, nucleosomes can inhibit or facilitate transcription factor binding. Also, packaging of DNA into nucleosomes varies depending on the cell cycle stage and by local DNA region (Russell 2010, 'iGenetics' 3rd ed. San Francisco: Pearson Benjamin Cummings, pp 24-27). The degree to which chromatin is condensed is associated with a certain transcriptional state. Unpackaged or loose chromatin is more transcriptionally active than tightly packaged chromatin because it is more accessible to transcriptional machinery. By remodeling chromatin structure and changing the density of DNA packaging, gene expression can thus be modulated. Accordingly, and without being bound by theory, the qualitative and/or quantitative level of chromatin packing of a given region of cfDNA may affect its stability, and hence the amount detected in the circulatory system at any given time, Correspondingly, differences between the level of chromatin packing between different DNA regions (for example, due to differences in each regions state of transcription) may influence the relative quantities of DNA from each of these regions when detected as cfDNA, particularly as two studies have investigated in more detail the kinetics of, and reported the rapid, clearance of cfDNA from the circulatory system (Gauthier et al 1996, J Immunol 156:1151; Lo et al 1999, Am J Hum Genet 64:218).

Various prior art methods have been described to detect, and quantify, cfDNA from a specific cell type. Quantitative analysis of aberrant p16 methylation was described using probe-based real-time quantitative PCR (Lo et al 1999, Cancer res 59:3899). Analogously, differences in the methylation of the placental mapsin gene found in material plasma has been described, and the methylation signature further analysed using MALDI-TOF mass-spectrometry (Chim et al 2005). Total cfDNA and that from male foetuses (only) were accurately and robustly quantified in material plasma from 5 to 41 weeks of gestation using a Y-chromosome specific marker (SRY) (Birch et al 2005, Clin Chem 51:2). Hypermethylation of RASSF1A has been proposed as a universal foetal DNA marker to improve the reliability of NIPT, and was studied in a duplex probe-based real-time PCR reaction compared to the non-differentially methylated region on the beta-actin gene (Chan et al 2006, Clin Chem 52:12). A complex method of quantification has been described (Nygren et al 2010; Clin Chem 56:10; WO 2010/033639; WO 2011/034631): starting from a 13-plex competition-PCR reaction (5 differentially methylated regions (DMRs) including TBX3, 3 regions on different genes for total DNA quantification, 3 for quantification of chromosome Y and 2 for restriction enzyme controls), such a complex reaction is subsequently processed for singe-base extension reactions and finally mass-spectrometry is subsequently conducted to both quantify and identify each of the single alleles my mass differences. Also using a complex process starting from methylated DNA immunoprecipitation, and based on SYBR green based quantitative PCR of a plurality of DMRs, has been claimed to be able to accurately quantitate foetal cfDNA and use such quantitation from eg chromosome 21 DMRs, to prenatally diagnose trisomies (Papageorgiou et al 2011, Nat Med 4:510; WO 2012/092592); although technical concerns about such an approach to diagnose trisomies have been raised (Tong et al 2012; Nat Med 18:1327). High-throughout droplet digital PCR (ddPCR) has been described for absolute quantification of DNA copy number from normal and tumorous breast tissues, and also total and foetal cDNA in maternal plasma using duplex probe-based quantitative PCR of RASSF1/RNaseP and RASSF1/beta-actin (Hindson et al 2011, Anal Chem 83:8604). Separate SYBR green quantitative PCR reactions of RASSF1A, SRY and DYS14 have been evaluated as an assay to detect RASSf1A to facilitate improved diagnostic reliability of NIPT (White et al 2012; PLOS ONE 7(9):e45073). However, generally considered as the "gold standard" for the quantitative measurement of foetal cfDNA against which other assays are often compared, remains the quantification of Y chromosome-specific genes (eg SFY) of male foetuses eg, as used by Yu and co-workers to determine whether the increased foetal cfDNA in maternal serum level of gravitas developed into early-onset preeclampsia (Yu et al 2013, Int J Mol Sci 14:7571).

Accordingly there is a need, from one or more of the above or perspectives, for improved methods to detect, preferably quantitatively, an amount of a species of DNA that originates from a particular cell type, such as a tumour-, foetal- or a placental cell, in particular to so detect cfDNA eg from the circulatory system of an individual.

Accordingly, it is an object of the present invention to provide alternative, improved, simpler, cheaper and/or integrated means or methods that address one or more of these or other problems. Such an object underlying the present invention is solved by the subject matter as disclosed or defined anywhere herein, for example by the subject matter of the attached claims.

Generally, and by way of brief description, the main aspects of the present invention can be described as follows:

In a first aspect, and as may be further described, defined, claimed or otherwise disclosed herein, the invention relates to a method for detecting in a sample from an individual an amount of a species of DNA originating from cells of a given type, which sample comprises said species of DNA in admixture with differently methylated DNA not originating from cells of said type; said method comprising the steps:
(a) treating the DNA present in said sample with a reagent that differentially modifies methylated and non-methylated DNA;
(b) detecting in said sample the presence of methylation in said species of DNA at one or more differentially methylated region(s) (DMR(s)) that is(are) differently methylated between said species of DNA and the DNA not originating from cells of said type, the modification of DNA of such DMR by said reagent is sensitive to methylation of DNA, wherein the presence of methylated DNA at said DMR indicates the presence of said amount of species of DNA in said sample and the absence of methylated DNA at said DMR indicates the absence of said species of DNA in said sample; and
(c) detecting an amount of total DNA present in said sample using at least one other region that is not differently methylated between said species of DNA and the DNA not originating from cells of said type, the modification of which regions(s) by said reagent is insensitive to methylation of DNA,
wherein, said other region is located between about 20 bp and about 20 kb upstream or downstream of said DMR.

In another aspect, the invention also relates to a method for detecting an increased risk of an individual suffering from or developing a medical condition, said method comprising the steps:
(i) conducting a method of the first aspect of the invention, wherein each of the detection steps comprises quantitative detection; and
(ii) comparing the amount of said species of DNA detected with a threshold amount and/or a reference distribution of amounts,
wherein an increase in, or outlying of, the amount of said species of DNA indicates an increased risk of the individual suffering from or developing said medical condition.

In other aspects, the invention also relates to a composition, a kit and a computer program product, in each case as may be described, defined, claimed or otherwise disclosed herein, for use within or in connection with a method of the invention.

The figures show:

FIG. 3 depicts the correlation of the amount of male specific DNA (Y chromosomal-representation) to the foetal cfDNA fraction measured by a method of the present invention (Example 1) for study twin cases with known foetal genders.

FIG. 4 depicts the improved sensitivity of a method of the invention compared to foetal cfDNA fraction detected using separate reactions of a single DMR. The number of PCR cycles (Cp) required for detection of foetal cfDNA (Example 2) in a sample using either RASSF1A or TBX3 alone as a single DMR, or as a multiplex (using the same labels) of RASSF1A and TBX3.

FIG. 5 depicts a schematic representation of the operations conducted by a computer program product of the invention.

Figure 1:
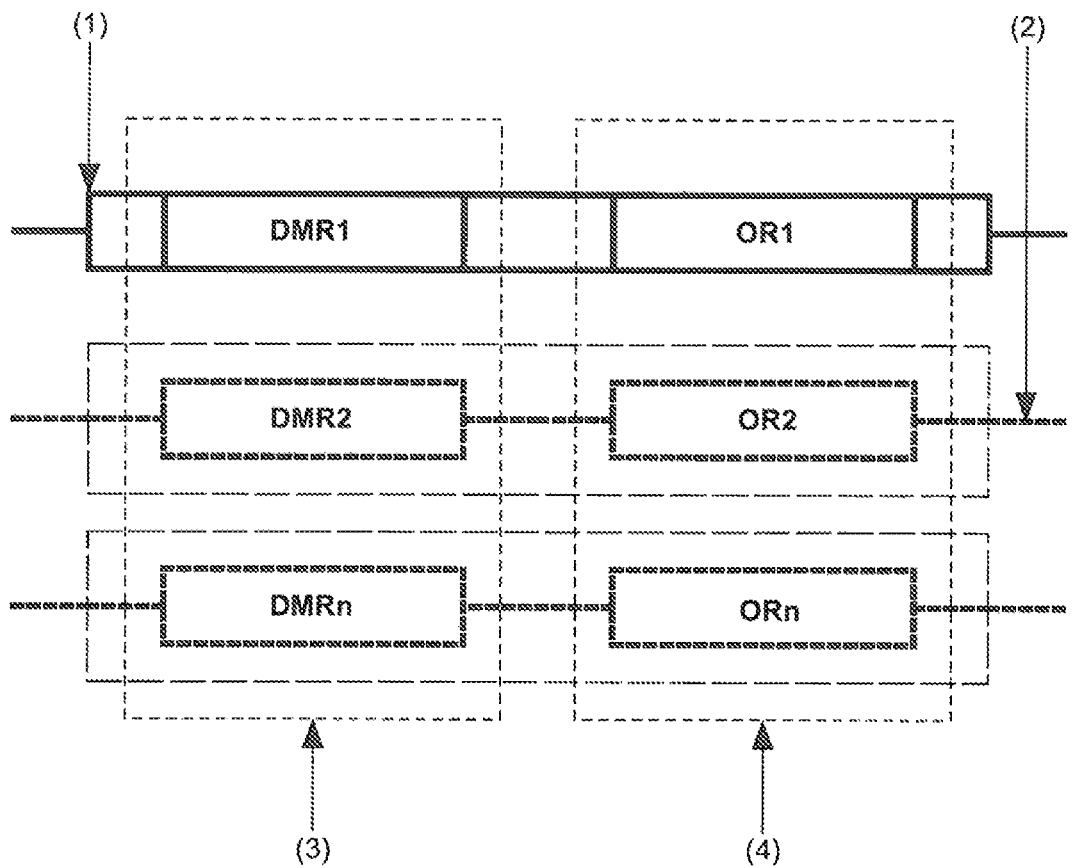
FIG. 1 depicts a schematic representation of the differentially methylated region(s) ("DMR") and other regions(s) ("OR") used in the method of the invention.

The present invention, and particular non-limiting aspects and/or embodiments thereof, can be described in more detail as follows:

In a first aspect, the invention relates to a method for detecting in a sample from an individual an amount of a species of DNA originating from cells of a given type, which sample comprises said species of DNA in admixture with differently methylated DNA not originating from cells of said type; said method comprising the steps:
(a) treating the DNA present in said sample with a reagent that differentially modifies methylated and non-methylated DNA;
(b) detecting in said sample the presence of methylation in said species of DNA at one or more differentially methylated region(s) (DMR(s)) that is(are) differently methylated between said species of DNA and the DNA not originating from cells of said type, the modification of DNA of such DMR by said reagent is sensitive to methylation of DNA, wherein the presence of methylated DNA at said DMR indicates the presence of said amount of species of DNA in said sample and the absence of methylated DNA at said DMR indicates the absence of said species of DNA in said sample; and
(c) detecting an amount of total DNA present in said sample using at least one other region that is not differently methylated between said species of DNA and the DNA not originating from cells of said type, the modification of which regions(s) by said reagent is insensitive to methylation of DNA,
wherein, said other region is located between about 20 bp and about 20 kb upstream or downstream of said DMR.

Terms as set forth herein are generally to be understood by their common meaning unless indicated otherwise. Where the term "comprising" or "comprising of" is used herein, it does not exclude other elements. For the purposes of the present invention, the term "consisting of" is considered to be a particular embodiment of the term "comprising of". If hereinafter a group is defined to comprise at least a certain number of embodiments, this is also to be understood to disclose a group that consists of all and/or only of these embodiments. Where used herein, "and/or" is to be taken as specific disclosure of each of the two specified features or components with or without the other. For example "A and/or B" is to be taken as specific disclosure of each of (i) A, (ii) B and (iii) A and B, just as if each is set out individually herein. In the context of the present invention, the terms "about" and "approximately" denote an interval of accuracy that the person skilled in the art will understand to still ensure the technical effect of the feature in question. The term typically indicates deviation from the indicated numerical value by ±20%, ±15%, ±10%, and for example ±5%. As will be appreciated by the person of ordinary skill, the specific such deviation for a numerical value for a given technical effect will depend on the nature of the technical effect. For example, a natural or biological technical effect may generally have a larger such deviation than one for a man-made or engineering technical effect. Where an indefinite or definite article is used when referring to a singular noun, e.g. "a", "an" or "the", this includes a plural of that noun unless something else is specifically stated.

In certain embodiments of the present invention, the individual is a human or a non-human animal, where such non-human animal may, in particular embodiments, be selected from the group consisting of: horse, sheep, cow, pig, chicken, mouse and rat. In a more specific embodiment, the individual is a pregnant female human or a human individual suspected of being at increased risk of developing or suffering (or suffering from) a medical condition, such as one or more of the medical conditions disclosed herein. Such a method of the present invention is not intended to be practiced on the human or animal body; for example it is intended to be practiced in an in-vitro manner.

In all aspects of the invention, the cell(s) of a given type may be a cell of a particular organ or tissues of the same individual. For example, the cell may be a tumour cell of the individual. Alternatively, such cell(s) may originate from a different individual or organism. For example, in the case of an individual being a pregnant female, the cell of a given type may be a cell of the foetus, including of the placenta of such foetus, and in other embodiments, the cell type may be an infectious agents such as a bacteria or a protozoa.

In certain embodiments of the present invention, said species of DNA and/or said differently methylated DNA is cell-free DNA, and in particular of such embodiments is circulating cell-free DNA. In one particular embodiment, said species of DNA and the differently methylated DNA that is admixed therewith are both circulating cell-free DNA. The term "cell-free DNA" (or "cfDNA") is art recognised, and includes the meaning of DNA that is found outside of a cell, such as in a biological fluid (eg blood, or a blood fraction) of an individual. "Circulating" is also an art-recognised term, and includes the meaning that an entity or substance (eg cfDNA) is present in, detected or identified in, or isolated from, a circulatory system of the individual, such as the blood system or the lymphatic system. In particular, when cfDNA is "circulating" it is not located in a cell, and hence may be present in the plasma or serum of blood, or it may be present in the lymph of lymphatic fluid.

The term "differentially methylated region" or "DMR" will be recognised by the person of ordinary skill in the art, and is also intended to refer to a region in chromosomal DNA that is differentially methylated (eg at a CpG motif) between said species of DNA and the other DNA with which it is admixed in the sample. For example in one embodiment, the DMRs used in the present invention are differentially methylated between foetal and maternal DNA, or are differentially methylated between tumour-derived and non-tumour-derived DNA from the same individual. In particular embodiments of the present invention, the DMRs are hypermethylated in foetal DNA and hypo methylated in maternal DNA, or are hypermethylated in tumour-derived DNA and hypomethylated in DNA that is derived from non-tumour tissue of the individual. That is, in such regions exhibit a greater degree (ie more) methylation in said species of DNA (eg the foetal or tumour cfDNA) as compared to the other DNA (eg maternal or non-tumour DNA), such as about 10%, 20%, 30%, 40%, 50%, 60%, 70%, 80%, 90% or 100% of, or more of, the sites available for methylation at a given DMR are methylated in said species of DNA as compared to the same sites in the other DNA.

A reagent is used in the present invention that differentially (eg selectively) modifies methylated as compared to non-methylated DNA. For example, treatment of DNA with a reagent comprising bisulphite (bisulfite) converts cytosine residues to uracil, but leaves 5-methylcytosine residues unaffected. Thus, bisulphite treatment introduces specific changes in the DNA sequence that depend on the methylation status of individual cytosine residues, yielding single-nucleotide resolution information about the methylation status of a segment of DNA. Various analyses can be performed on the altered sequence to retrieve this information, including the use of PCR primers and/or probes that can distinguish between such singe-nucleotide changes.

Such a reagent may alternatively (or in addition) comprise a restriction enzyme that is sensitive to the DNA methylation states. Cleavage of such a restriction enzyme's recognition sequence may be blocked, or impaired, when a particular base in the enzyme's recognition site is modified, eg methylated. In particular embodiments of all aspects of the invention, the reagent comprises a methylation-sensitive restriction enzyme, such as a methylation-sensitive restriction enzyme disclosed herein; including such embodiments that comprise two, three, four, five or more of such methylation-sensitive restriction enzymes.

Prior to step (a), the sample may be processed to isolate, enrich and/or purify, the DNA present therein. For example, a plasma sample may be processed using a cfDNA isolation process or kit to provide a (non-natural) subsequent solution that comprises an admixture of said species of DNA together with the differentially methylated DNA that does not originate from the cell-type. The step of treating in (a) may comprise the step of adding a separate solution that comprises said reagent (eg a methylation sensitive restriction enzyme) to the admixed DNA of the sample (eg, to a non-natural solution comprising such admixed DNA); and/or may comprise maintaining (or changing to) certain conditions. In particular, when said reagent comprises one or more methylation sensitive restriction enzyme, the step of treating in (a) may comprise incubating the DNA and the enzyme(s) together at about 37° C. for between about 5 min and 300 min, such as between about 30 min and 90 min or about 60 min, and optionally may comprise a step of incubating such mixture at a higher temperature (for example, between about 50° C. and 90° C.m such as about 80° C.) so as to deactivate the enzyme(s). In certain embodiments, the composition formed for a treating step of (a) may be non-naturally occurring. For example, particular salts of components of the solution (or buffer); and/or the mixture of (eg human) cfDNA together with one or more bacterial-derived restriction enzymes (or a non-natural mutant thereof) may be a non-natural composition or mixture.

In contrast, an "other region" ("OR") used in the present invention is not (significantly) differentially methylated between said species of DNA and other DNA with which it is admixed in the sample. For example, under the conditions and nature of the reagent used, there is no detectable difference between modification by such reagent at the other region of said species of DNA (eg foetal DNA) as compared to the other region of the admixed DNA (eg the maternal DNA). Such a non-difference may be achieved if the other region comprises no sites for methylation, if there is no difference in the degree of methylation if such sites are present, or by the use of a reagent that does not recognise any sites of methylation present in the other region.

The other region used in the present invention (that is not so differentially methylated) should be non-overlapping with the DMR used in the present invention. For example, the other region can be located further than about 10 bp, 20 bp, 50 bp, or more than 100 bp, 500 bp, 1 kb or 10 kp, away from the DMR, such as is located between about 20 bp and about 20 kb upstream or downstream of (including embodiments being located within the same gene as) said DMR. In particular, the genomic location of the other region used in the present invention is generally located in the same portion of the genome, such as between about 20 bp and about 20 kb upstream or downstream of (including embodiments being located within the same gene as) the genomic location of at least one of the DMRs used herein. The inventors find that detection (and particularly quantification) of the species of DNA is enhanced (eg, in terms of sensitivity, accuracy and/or precision) if the other region is so located in the same portion of the genome as one of the DMRs. Without being bound by theory, it is believed that with such similarly-located DMR(s) and other region, the effect of variation in chromatin/nucleosome packing across the genome—and hence stability/degradation of different regions of genomic DNA—is mitigated, such that any difference in stability/degradation of a DMR (ie detecting the species of DNA) as compared to the other region (is detecting total DNA) is less, and hence a relative (and absolute) quantification may be made without it being (significantly) confounded by quantitative differences brought about by (significantly) differential chromatin/nucleosome pecking across the genome between a DMR and an other region.

In one embodiment of the present invention, the detection of the various DNA regions, ie the DMR(s) and the other region(s), may occur in a simplified process. For example, using a single aliquot of DNA from the sample, such DNA regions may be detected in a single vessel. This feature may simplify the method, and can provide for more efficient and accurate detection (especially in those embodiments when detection is quantitative). The term "vessel" will be art recognised, and includes embodiments of a vessel (such as a tube, well of a microtitre plate, nano-well, capillary reaction vessel etc) in which a process or procedure comprised in the method occurs, such as a reaction and/or detection process or a step of a method of the present invention. Other such vessels may include droplets in oil/water emulsions, nanoparticles or a hybridisation chamber; as appropriate to the detection technology used. The detectable labels used, in certain embodiments may be the same for each DMR and/or may be the same for each other region, provided that, when detected essentially simultaneously, the label(s) used for the other region(s) is different (ie, can be separately detected) to the label(s) used for the DMR(s). Detectable labels that are "the same" can also include labels while structurally different, are functionally (essentially) similar as they cannot be significantly differentiated by the detection technology employed. For example, structurally different fluorescent dyes may be considered "the same" if their excitation and emission spectra are (substantially or essentially) similar, or overlap to such a degree that they are able to be excited and detected simultaneously with the same wavelength(s). Suitable labels (and detection modalities) are further described elsewhere herein. Optionally, the detection of the DMR(s) and other region(s) may be made effectively simultaneously. For example, within the same (reaction/detection) vessel, all such regions (and hence said species of DNA and total DNA) can be detected within less than about 5 s, 1 s, 0.5 s, 100 ms, 10 ms, 1 ms, 100 us, 10 us or 1 us of each other, and for example without transferring the vessel, or the reaction/mixture, to any subsequent vessel, assay or equipment, or for example, without adapting or recalibrating the detection process for the DMR(s) or the other region(s) separately. The use of two different detectable label(s)—one for said DMR(s) and one for the other region(s)—utilises components, process and/or steps that are non-natural. For example, a composition of two specific labels together with the specific DNA regions would (generally) not be found in nature. In particular, short probes used in quantitative probe-based PCR, while may comprise a DNA sequence that is a fragment of that found in a natural genome, when linked to a one or more labels (such as a fluorescent dye) form a specific labelled fragment that is non-natural.

Collectively, the features of the present invention provide for certain advantages over prior art methods. These can include sensitive detection of methylation (and hence the species of DNA to be detected) and/or accurate and/or improved precision quantification of the amount of said species of DNA by reference to the amount of total DNA detected using a co-located other region, and optionally within the same assay, from the same aliquot of admixed DNA and effectively simultaneously with the detection of the two or more DMRs.

By way of graphical description, a schematic representation of the general arrangement of the DMR(s), the other region(s) and the detectable label(s), as used for the present invention, is presented in FIG. 1. (1) The presence of methylation in DNA at DMR1 is detected in the context of an other region ("OR1") is located within the same portion of the genome (eg, between about 20 bp and about 20 kb upstream or downstream of) DMR1. (2) Optionally, additional DMRs and/or ORs (such as DMR2 and/or OR2, and up to DMRn and ORn) may be detected, and pairs of such additional DMRs and ORs may each be co-located in the same portion of the genome (eg, between about 20 bp and about 20 kb upstream or downstream of) as each other. Optionally, (3) the presence of methylation in DNA is detected at multiple DMRs, using the same detectable label(s) and/or (4) the amount of total DNA detected using at least one OR (OR1, and optionally, OR2 or up to ORn) is detected using different detectable label(s) to those used to detect methylation at the DMR(s) (optionally, the detectable label(s) used is the same for all the ORs).

In particular embodiments, said detection in step (b) comprises the use of two or more of said DMRs, and such two or more DMRs may be detected in such step using the same detectable label(s) for each of said DMRs. The combination of a feature of the present invention (similarly-located DMR(s) and other region(s)) with one of more other feature of the present invention: eg the use of at least two DMRs, and/or the detection in step (b) and the detection in step (c) are made using the same aliquot of DNA of the sample, and in the same reaction/detection vessel, and effectively simultaneously for such DMRs and other region, and/or using: (x) the same detectable labels(s) for each of said DMRs; and/or (y) a different detectable label for said other region(s); is each a preferred embodiment of the present invention. The use of such a combination of features in the present invention provides opportunity for efficiency improvements and/or synergistic enchantment of outcome. For example, an improved sensitivity and/or accuracy and/or precision of detection (eg, detection of a quantitative amount) or said species of DNA can be obtained by the use of such a combination; the degree of improvement of which can be synergistic, as compared to the use of each feature alone; eg the enhancement obtained by use of the combined features being greater than the sum of each enhancement obtained by the use of each feature individually.

In certain embodiments, prior to or as part of the detection that occurs as part of a step (b) and/or a step (c) of any method of present invention, each DNA region comprising said DMR(s) and/or said other region(s), respectively, is(are) amplified. Amplification of DNA may be conducted using any suitable replication process, and in particular of such embodiments, each of the DMR(s) and/or other region(s), is amplified by a polymerase chain reaction (PCR) using primers suitably designed for each DMR and/or other region. The person of ordinary skill will readily be able to design such PCR primers for use in the method of the invention, for example by use of primer design algorithms and programs such as Clone Manager Professional 9 (Sci-Ed Software), Vector NTI (Life Technologies), or web-based tools such as those found from www.ncbi.nim.nih.gov/tools/primer-blast/ or molbiol-tools.ca/PCR.htm. Those embodiments of the present invention that comprise PCR amplification can further comprises specific steps that are related to the practice of PCR, such as any of those described herein, or in particular the steps of: (A) providing a reaction mixture comprising a double-stranded target DNA, a pair of primers (for example, a pair of primers disclosed herein) designed to amplify a region of such DNA (such as a DMR or an other region as described herein) wherein the first primer is complementary to a sequence on the first strand of the target DNA and the second primer is complementary to a sequence on the second strand of the target DNA, Taq polymerase, and a plurality of free nucleotides comprising adenine, thymine, cytosine and guanine; (B) heating the reaction mixture to a first predetermined temperature for a first predetermined time to separate the strands of the target DNA from each other; (C) cooling the reaction mixture to a second predetermined temperature for a second predetermined time under conditions to allow the first and second primers to hybridise with their complementary sequences on the first and second strands of the target DNA, and to allow the Taq polymerase to extend the primers; and (D) repeating steps (B) and (C) at least 20 times.

In other embodiments, a detectable label used in step (b) and/or step (c) of a method of the invention is independently selected from the group consisting of: fluorescent, protein, small molecule or radioactive label. For example, fluorescent labels that are the same (including, by having similar or overlapping excitation and/or emission spectra) may be used for the DMR(s), and a fluorescent label that has an excitation and/or emission spectra (in particular, a different emission spectrum) may be used for detection of the other region(s). The person of ordinary skill will be able to select appropriate such fluorescent label(s) for use in the present invention from, for example, the group consisting of: FAM, TET, JOE, VIC, HEX, NED, PET, ROX, TAMRA, Quasar and Texas Red. In other embodiments, a detectable label may be a protein or small molecule tag that, for example, can be detected using a specific antibody and ELISA-type detection approaches. The use of the same protein or small molecule for each of the DMR(s), and a detectably different protein or small molecule for the other region(s), may also be utilised for the detectable label(s) used in the present invention.

Different radioactive labels may be distinguished by their emission energy, penetration/excitation characteristics and particle-type (for example, by distinguishing between alpha and beta particles). Other detectable labels (such as nucleic-acid coded tag) may also be employed in the present invention.

In particular embodiments, the detection in step (b) of a method of the example comprises real-time quantitative probe-based PCR, eg by using at least one labelled probe which is specific for one of the DMR(s). In those embodiments where PCR amplification of multiple DMRs is made in the same reaction, such PCR can be considered as "multiplex" (or "duplex" if only two DMRs are so amplified). Likewise, the detection in step (c) in the methods of the invention may, in addition or alternatively, comprise real-time quantitative probe-based PCR, such as by using at least one labelled probe specific for one of said other region(s).

The term "probe-based" quantitative PCR is art recognised, and encompasses various embodiments described and marketed under different brand names (such as "TaqMan" PCR of Roche), and uses a (eg fluorescent) reporter probe that is specific for the detection of a given amplicon (eg a DMR or an other region). Probe-based quantitative PCR is distinct from quantitative PCR using double-stranded DNA-binding dyes (eg SYBR Green) as reporters, as such double-stranded DNA-binding dyes bind non-specially to any double-stranded amplicon and eg cannot be used to distinguish between detection of the DMR(s) (ie said species of DNA) from detection of the other region(s) (ie detection of total DNA). As the person of ordinary skill will appreciate, a specific amplicon of PCR may be detected using a single probe or by using multiple probes (such as two or three probes) for an amplicon.

Such probe-based quantitative PCR may be conducted in an analogue-approach, using a machine such as a LightCycler in which the intensity of signal (eg over time) is measured and used to quantitatively determine detection. Alternatively, digital PCR (dPCR), ie, PCR conducted in multiple events so as to determine the number of amplification events as method to quantitate an amount of detected DNA. For example, dPCR that is conducted in nano-wells or droplets (ddPCR).

The person of ordinary skill will be able to design suitable primers and probes (and with suitable labels, eg dyes) for probe-based quantitative PCR detection of the DMRs and/or other regions(s); for example by using primer/probe design software as described elsewhere herein. As will be known, the PCR primers may overlap methylation site(s) specific for the methylation-specific modifying reagent used in the methods, in particular when the reagent comprises one or more methylation sensitive restriction enzyme, such as one (or a combination thereof) as disclosed herein. In particular such embodiments, one or other (or when considered together, both) of the PCR primers for a given DMR may overlap two or three such methylation sites (such as two or three restriction sites for methylation-sensitive restriction enzymes, each of which may comprise, or comprises, a methylation site). Alternatively or in addition, the primers for a DMR may be designed to flank one, two, three or more such methylation sites, such as up to 10, 15, 20, 25 or 50 such methylation sites, in particular flanking restriction sites for one, two, three or more such methylation sites, such as up to 10, 15, 20, 25 or 50 methylation-sensitive restriction enzymes, each of which may comprise, or comprises, a methylation site.

The present invention includes the use of one other region to provide for the detection of an amount of total DNA in the admixture. However, the present invention also encompasses embodiments that use more than one other region. For example, the invention includes such embodiments wherein said detection in step (c) comprises using at least two of said other regions, such as two, three or four of said other regions. In particular embodiments of all aspects of the present invention, the number of said other regions is the same as the number of DMRs used in step (b). For example, if two DMRs are used then two other regions are used in such an embodiment, and if three DMRs are used then three other regions are used (such as depicted in FIG. 1).

As described elsewhere herein, the present invention includes where the other region is generally located in the same portion of the genome, such as between about 20 bp and about 20 kb upstream or downstream of (including embodiments within the same gene as) the genomic location of at least one of the DMRs used herein. Accordingly, if multiple other regions are used in the present invention, then embodiments are included where two or more of such other regions are similarly located in the genome to the two or more DMRs. For example, one of said other regions may be located between about 20 bp and about 20 kb upstream or downstream of (including embodiments within the same gene as) a DMR used in step (b) and each other of the said other regions (eg, a second other region) is located between about 20 bp and about 20 kb upstream or downstream of (including embodiments within the same gene as) another of said (eg, non-overlapping) DMRs (eg, the second DMR). In certain embodiments an additional other region, may overlap with a DMR.

An other region used in the present invention, when generally located in the same portion of the genome as a DMR, may be located upstream or downstream of one of said DMRs within a distance selected from the group consisting of: between about 16 kb to 20 bp, 14 kb to 20 bp, 12 kb to 20 bp, 10 kb to 20 bp, 8 kb to 20 bp, 6 kb to 20 bp, 5 kb to 20 bp, 4 kb to 20 bp, 3 kb to 2 bp, 16 kb to 20 bp, 1 kb to 20 bp, 500 bp to 20 bp, 200 bp to 20 bp, 20 kb to 15 kb, 15 kb to 10 kb, 12 kb to 8 kb, 10 kb to 8 kb, 11 kb to 7 kb, 11 kb to 10 kb, 9 kb to 8 kb, 8 kb to 6 kb, 6 kb to 4 kb, 4 kb to 2 kb, 2 kb to 500 bp, 1 kb to 100 bp, 500 bp to 50 bp, 400 bp to 200 bp and 500 bp to 100 bp. In particular embodiments, each other region used in the present invention is so generally located to a different of the DMRs used.

If multiple other regions are used, then the present invention includes embodiments where the detection in step (c) is made using the same detectable label for each of said other regions and/or comprises multiplex real-time quantitative PCR using at least two labelled probes each of which is specific for one of said other regions.

In particular embodiments, all detection steps (ie, those required for all DMR(s) and all other region(s)) are conducted in an efficient and effective manner using multiplex quantitative probe-based (eg TaqMan) PCR, in one process step or reaction. For example, the detection in step (c) and said detection in step (b) are made using the same aliquot of DNA of said sample, and in the same reaction/detection vessel, and effectively simultaneously with each other, and by multiplex real-time quantitative PCR using at least one labeled probe specific for each of the said DMRs and other region(s). In particular of such embodiments, the reagent comprises one or more methylation sensitive restriction enzyme, such as one (or a combination thereof) as disclosed herein.

The present invention may also include further procedures, such as one or more control procedures. For example, the present invention can include one or more steps directed to the detection of a third class of DNA region that acts as a control for the modification step (eg, as a control for restriction enzyme digestion). Such embodiments may, for example, also be conducted using multiplex real-time quantitative probe-based PCR wherein such control region is amplified and detected by a third set of primer/probe(s) with a third detectable label used for such class of region.

In one embodiment of the present invention of particular relevance, said species of DNA originates from cells of a foetus and/or the placenta of a foetus and said sample is from a pregnant female. In such embodiments, the sample may be obtained in a non-invasive manner. For example, said species of DNA is circulating cell-free DNA that has been detected from the sample being blood or a blood fraction (such as plasma or serum) that has been obtained from the pregnant female by conventional means such as a blood collection tube.

The present invention includes embodiments where the DMR(s) is(are) hypermethylated in foetal DNA and hypo methylated in maternal DNA. In certain embodiments, such a DMR may be located in a promoter, enhancer region or an exon of a gene, such as a gene disclosed herein. Alternatively, a DMR may be located in an intron of such a gene, or in a non-coding region of the genome. In particular embodiments of all aspects of the present invention, such genome and/or gene is a human genome or gene. Specifically included in the present invention are embodiments wherein said DMR(s) comprises at least one, preferably at least two, methylation site(s) specific for said reagent, and at least one of said DMR(s) is located in a portion of the genome and/or gene (eg a human genome or gene) that is RASSF1A and/or TBX3, or selected from the group consisting of: RASSF1A, TBX3, HLCS, ZFY, CDC42EP1, MGC15523, SOX14 and SPN. Also, embodiments are included wherein said DMR(s) comprises at least one, preferably at least two, methylation site(s) specific for said reagent, and at least one of said DMR(s) is located in a region and/or gene selected from the group consisting of: AIRE, SIM2, ERG, VAPA-APCDDI, one disclosed in WO 2011/034631 as being hypermethylated in foetal DNA relative to maternal DNA (eg, SEQ ID NOs: 1-59, 90-163, 176, 179, 180, 184, 188, 189, 190, 191, 193, 195, 198, 199, 200, 201, 202, 203, 205, 206, 207, 208, 209, 210, 211, 212, 213, 214, 221, 223, 225, 226, 231, 232, 233, 235, 239, 241, 257, 258, 259, and/or 261 of WO 2011/034631) and one disclosed in WO 2011/092592 (eg, EP1, EP2, EP3, EP4, EP5, EP6, EP7, EP8, EP9, EP10, EP11 and/or EP12 of WO 2011/092592, as further investigated in Lim et al 2014, BMC Medical Genomics 7:1).

If two DMRs are used, then in particular embodiments of all aspects of the present invention, they are not located in the same portion of the genomic and/or gene. For example, such DMRs may be located on separate chromosomes, or separated by more than about 20 kb, or more than about 15 kb, 10 kb, 8 kb, 6 kb, 4 kb, 2 kb, 1 kb, 500 bp or 200 bp. Alternatively, it is envisioned, that when two (or more) DMRs are used in the present invention, they may, in certain embodiments, be located in the same region or gene (such as one described herein) and, further, may overlap with each other.

In particular embodiments of the present invention, when two of said DMRs are used (or more than two DMRs are being used) each is located in a portion of the genome and/or gene (preferably that is human) that is RASSF1A and/or TBX3, or is selected from the group consisting of: RASSF1A, TBX3, HLCS, ZFY, CDC42EP1, MGC15523, SOX14 and SPN; and/or at least one of said DMRs is located between about positions 4,700 bp and 5,600 bp of RASSF1A (NCBI Reference Sequence: NG_023270.1: *Homo sapiens* Ras association (RalGDS/AF-6) domain family member 1 (RASSF1), RefSeqGene on chromosome 3; SEQ ID NO.: 13) or about positions 1,660 bp and 2,400 bp of TBX3 (NCBI Reference Sequence: NG_008315.1: *Homo sapiens* T-box 3 (TBX3), RefSeqGene on chromosome 12; SEQ ID NO.: 14). In a more particular embodiment, two (or more) DMRs are used, and a first DMR comprises one located between about positions 4,700 bp and 5,600 bp of RASSF1A and a second DMR comprises one located between about positions 1,660 bp and 2,400 bp of TBX3.

In particular embodiments, a DMR is located in RASSF1A between about positions 4,900 bp and 5,500 bp, 5,000 bp and 5,400 bp, or 5,100 bp and 5,300 bp of RASSF1A; and/or is located in TBX3 between about positions 1,800 bp and 2,260 bp, 1,920 bp and 2,160 bp or 1,920 bp and 2,080 bp of TBX3.

Figure 2:
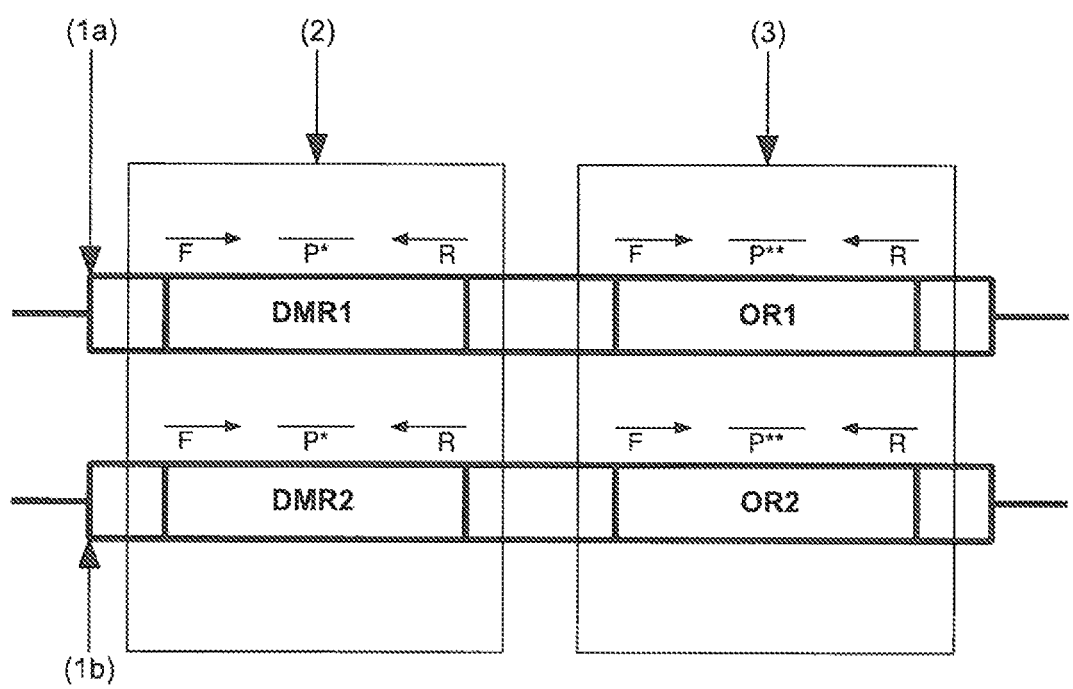
FIG. 2 depicts a schematic representation of the differentially methylated regions ("DMR") and other regions ("OR") used in Example 1.

The general arrangement of the DMRs and other regions ("OR") used in one embodiment of the present invention, is graphically represented by FIG. 2: (1a) DMR1 is found in exon 2 of RASSF1A and OR1 is located within exon 4 of RASSF1A, with DMR1 located between positions 50,340,672 bp and 50,340,784 bp and OR1 located between positions 50,331,604 bp and 50,331,702 bp of the RASS1A genomic sequence (NCBI Reference Sequence: NC_000003.12 *Homo sapiens* chromosome 3, GRCh38 Primary Assembly), separating DMR1 and OR1 by a distance of 8,969 bp. (1b) DMR2 is found in the promoter region of TBX3, with DMR2 located between positions 114,687,095 bp and 114,687,189 bp and OR2 is located between positions 114,676,384 bp and 114,676,454 bp of the TBX3 genomic sequence (NCBI Reference Sequence: NC_000012.12 *Homo sapiens* chromosome 12, GRCh38 Primary Assembly), separating DMR2 and OR2 by a distance of 10,640 bp. (2) Methylation in DNA at the two DMRs is detected using probe-based quantitative PCR using the respective forward (F) and reverse (R) PCR primers and region-specific probes, each probe labelled with the same labels (P*). (3) Total DNA is detected at two ORs using probe-based quantitative PCR using the respective forward (F) and reverse (R) PCR primers and region-specific probes, each probe labelled with the same labels for the ORs that is different to the labels used for the two DMRs (P**). Details of primer and probe sequences and probe labels are set out in TABLE 1.

The term "methylation site(s)" will be art-recognised, and has a meaning that encompasses, for example, a CpG motif within a short nucleotide sequence (eg one that is 4, 6, 8, 10 or 12 bp in length) that is, preferably, recognised by a methylation-sensitive restriction enzyme, such as one disclosed elsewhere herein.

Analogously, the other region, when located in particular portions and/or genes of the genome, may be located in a promoter, enhancer region or an exon of a gene, or alternatively, located in an intron of such a gene, or in a non-coding region of the genome. In particular embodiments of all aspects of the present invention, such genome and/or gene is a human genome or gene. In particular embodiments, when an other region used in the present invention is located in the same portion of the genome and/or gene that features one or more DMRs (preferably, non-overlapping with a DMR used in the invention), then it is located in a portion of the genome and/or gene such as a gene (eg human, and/or in particular when said species of DNA is foetal cfDNA) that is RASSF1A and/or TBX3, or is selected from the group consisting of: RASSF1A, TBX3, HLCS, ZFY, CDC42EP1, MGC15523, SOX14 and SPN. When not co-located with a DMR (for example, when a second or multiple other region is used), then such other region may, in certain embodiments, be located in a (eg human) housekeeping gene (such as GAPDH, beta-actin, ALB, APOE or RNASEP). In particular embodiments, said other region comprises a portion of the genome without a methylation site specific for said reagent, and said other region is located in the (eg human) genes RASSF1A or TBX3 (eg SEQ ID NOs: 13 and 14 respectively), and includes more particular embodiments wherein two or more of said other regions are used in detection step (c) and the first other region is located between about positions 14,220 bp and 13,350 bp of such RASSF1A and the second other region is located between about positions 12,400 bp and 13,000 bp of such TBX3. In particular embodiments, an other region is located in RASSF1A between about positions 14,230 bp and 14,340 bp, 14,230 bp and 14,330 bp, 14,230 bp and 14,320 bp, or 14,230 bp and 14,310 bp of such RASSF1A; and/or is located in TBX3 between about positions 12,400 bp and 12,940 bp, 12,700 bp and 12,850 bp or 12,710 bp and 12,790 bp of such TBX3. Alternatively, an other region may be located in an exon such as between about positions 13,790 bp and 13,880 bp, or 14,490 bp and 14,600 bp of such RASSF1A, or between about positions 8,040 bp and 8,180 bp or 6,230 bp and 6,350 bp of such TBX3; or an other region may be located in an intron such as between about positions 10,500 bp and 11,90 bp of such RASSF1A, or between about positions 10,000 bp and 11,000 bp of such TBX3

There is now strong evidence that the level of foetal cfDNA (and/or total cfDNA) present in the circulatory system (eg in plasma) of a pregnant female is a marker of one or more forms of preeclampsia, such as early-onset preeclampsia, mild and/or severe preeclampsia (see Hahn et al 2011, Placenta 32(Supl):S17). The present invention shows particular utility in the efficient, effective, sensitive and/or low-variability detection/quantification of foetal cfDNA present in plasma of pregnant females, and the present invention has particular utility therein. Accordingly, in particular embodiments of the present invention, the individual is a pregnant female and is susceptible to suffering or developing a pregnancy-associated medical condition; particularly where said pregnancy-associated medical condition is preeclampsia. As used herein, an individual "susceptible to" a medical condition may alternatively be described as "is suspected to" or to "be considered at risk of being susceptible to" suffering or developing a medical condition; and in certain embodiments, the present invention is used to screen and/or diagnose the individual for susceptibility to, risk of suffering or developing, or suffering from or developing, a medical condition.

In alternative embodiments, the individual is a pregnant female and is susceptible to (or considered at risk of being susceptible to) suffering or developing a pregnancy-associated medical condition selected from the group consisting of: preterm labour, intrauterine growth retardation and vanishing twin. In particular, the inventors were surprised that the sensitivity of the present invention was such that discrepancies between cfDNA levels determined by the method of the invention and that determined by counts of Y-chromosome sequences as determined by massively parallel sequencing approaches, was useful in identifying one or more cases of a vanishing twin in (mixed-sex) twin pregnancies that previously were believed to be singleton pregnancies, and/or to follow the relative development and health of one or other of such (mixed-sex) twin pregnancies. The present invention may also be utilised in gender determination of twin pregnancies, by consideration of the relative values for foetal cDNA compared to counts of Y-chromosome sequences determined from cfDNA (eg by using parallel sequencing approaches). In these regards, it should be noted that approaches that use massively-parallel sequencing of random cfDNA in maternal blood typically always count a very low frequency of "Y-chromosome" sequences (such as between about 0.003% and 0.004% of all sequences, or between about 0.0015% and 0.01% or 0.002% and 0.005% of all sequences) in all female pregnancies due to homology of certain Y-chromosome short sequences to other chromosomes. A cut off of "Y-chromosome" sequence counts of about 0.005%, or between about 0.003%, 0.004%, 0.006% or 0.007%, may therefore be employed for female samples.

As described elsewhere herein, there is also increasing evidence that the presence and amount of methylated DNA at certain DMRs is indicative or prognostic of certain medical conditions that are not associated with pregnancy. Accordingly, in another particular embodiment of the present invention, said species of DNA originates from a cell type associated with such a medical condition, particularly in those embodiments where said species of DNA is circulating cell-free DNA and said sample is a blood fraction such as plasma or serum. For example, the medical condition may be a cell proliferative disorder, such as a tumour or cancer. In particular embodiments, the medical condition is a tumour or a cancer of an organ selected from the list consisting of: liver, lung, breast, colon, oesophagus, prostate, ovary, cervix, uterus, testis, brain, bone marrow and blood; and/or said species of DNA may originate from cells of a tumour; particularly where such tumour is a carcinoma or cancer of an organ selected from the group consisting of: liver, lung, breast, colon, oesophagus, prostate, ovary, cervix, uterus, testis, brain, bone marrow and blood.

When used in the context of a medical condition being a tumour or cancer, the present invention includes embodiment wherein said DMR(s) comprises at least one, preferably at least two, methylation site(s) specific for said reagent, and at least one of said DMR is located in a portion of the genome and/or a gene (in particular, when such genome and/or gene is a human genome or gene) selected from the group consisting of: a tumour suppressor gene, p16, SEPT9, RASSF1A, GSTP1. DAPK, ESR1, APC, HSD17B4 and H1C1. In particular, one of said DMR(s) may be located in RASSF1A (eg SEQ ID NO. 13) such as located between about positions 4,700 bp and 5,600 bp of such RASSF1A; and/or said other region is located between about positions 14,220 bp and 13,350 bp of such RASSF1A. Other particular locations of the DMR(s) and/or other region(s) within RASSF1A for use in this embodiment are disclosed elsewhere herein. Furthermore, the person of ordinary skill will now recognise that other DMRs and/or other regions located in other portions of the genome of in other genes may be identified from the relevant scientific literature (eg, for review, see Elshimali 2013). In particular when used in the context of a medical condition being a tumour or cancer, the present invention includes embodiments where at least one or more additional other region(s) are located in a (eg human) housekeeping gene (such as GAPDH, beta-actin, ALB, APOE or RNASEP). Alternatively for such context, said additional other region(s) may be located in the same portion of the genome and/or gene that feature one or more DMRs (such as those p16, SEPT9, RASSF1A, GSTP1. DAPK, ESR1, APC, HSD17B4 and H1C1).

In yet another particular embodiment of the present invention, said species of DNA originates from a cell type associated with a medical condition selected from the group consisting of: an infection/infectious disease, a wasting disorder, a degenerative disorder, an (auto)immune disorder, kidney disease, liver disease, inflammatory disease, acute toxicity, chronic toxicity, myocardial infarction, and a combination of any of the forgoing (such as sepsis) and/or with a cell proliferative disorder, particularly in those embodiments where said species of DNA is circulating cell-free DNA and said sample is a blood fraction such as plasma or serum. For example, the medical condition may be an infection/infectious disease, such as one caused by a bacterial, viral or protozoan pathogen, including a pathogen selected from the group consisting of: a retrovirus (such as HIV), a herpes virus (such as HSV, EBV, CMV, HHV or VSV), dengue virus, mycobacteria (eg *Mycobacterium tuberculosis*), and hantavirus. In certain embodiments, the medical condition is sepsis and/or excludes kidney disease.

In all aspects of the present invention, there exist embodiments wherein the sample is a tissue sample or a sample of biological fluid. In particular, the sample is whole blood or a blood fraction (eg, such as plasma or serum). In alternative embodiments, the sample is biological fluid selected from the group consisting of: urine, saliva, sweat, ejaculate, tears, phlegm, vaginal secretion, vaginal wash and colonic wash. In more particular embodiments, the sample is a plasma or serum sample from the individual, or is urine from the individual. In other embodiments, the sample is largely (or essentially) free from cells, and/or is not a whole blood and/or ejaculate sample. In certain embodiments, the sample is not ejaculate if the individual is female and the sample is not a vaginal wash if the individual is male.

In all aspects of the present invention, the reagent that differentially modifies methylated and non-methylated DNA may comprise bisulphite and/or an agent that selectively digests unmethylated over methylated DNA (for example, such agent may digest unmethylated DNA but not methylated DNA). In particular embodiments, the reagent agent comprises: at least one methylation sensitive enzyme; at least one methylation sensitive restriction enzyme; and/or an agent selected from the group consisting of: AatII, AciI, AclI, AfeI, AgeI, AgeI-HF, AscI, AsiSI, AvaI, BceAI, BmgBI, BsaAI, BsaHI, BsiEI, BsiWI, BsmBI, BspDI, BsrFI, BssHII, BstBI, BstUI, ClaI, EagI, FauI, FseI, FspI, HaeII, HgaI, HhaI, HinP1I, HpaII, Hpy99I, HpyCH4IV, KasI, MluI, NaeI, NarI, NgoMIV, NotI, NotI-HF, NruI, Nt.BsmAI, Nt.CviPII, PaeR7I, PluTI, PmlI, PvuI, PvuI-HF, RsrII, SacII, SalI, SalI-HF, SfoI, SgrAI, SmaI, SnaBI, TspMI and ZraI. In particular embodiments, said reagent is one selected from the group consisting of: BstUI, HhaI and HpaII.

In related embodiments, the reagent may comprise two or more of any of the reagents disclosed herein. For example, it may comprise two, three, four, five or more (eg up to seven, eight or ten) methylation sensitive restriction enzymes, including a reagent comprising or essentially consisting of two or three of the methylation sensitive restriction enzymes selected from the group consisting of: BstUI, HhaI and HpaII The use of bisulphite or methylation-sensitive restriction enzymes to study differential methylation will be well known to the person of ordinary skill, who may apply teachings of standard texts or adaptation of published methods such as Poon et al (2002), Nygren et al (2010) or Yegnasubramanian; et al (2006, Nuc Acid Res 34:e19). By way of illustration, the inventors provide examples herein that employ the use of methylation-sensitive restriction enzymes as the reagent that differentially modifies methylated and non-methylated DNA. For further illustration using bisulphite as reagent, it will be apparent to the person of ordinary skill that bisulphite-modified DNA methylation sites may be detected using eg methylation-specific PCR (such as using primers and/or probes that selectively bind to the bisulphite-modified sequences) and/or by the subsequent use of restriction enzymes the recognition site of which is created upon such bisulphite-modification.

In particular embodiments of all aspects of the invention, a quantitative amount of said species of DNA (and/or or said total DNA) is to be detected and/or determined. Accordingly in such embodiments, one or more (eg each) of said detection steps comprises quantitative detection and said detected amount of said species of DNA is expressed as a relative concentration of said species of DNA to the total DNA present in said sample.

If an absolute amount of total DNA is known, then correspondingly an absolute amount (for example, as represented by a concentration such as ug/mL or genome-equivalents such as Eg/mL) of the species of DNA can be determined from such relative concentration. An absolute amount of total DNA for a sample may be determined, for certain embodiments, by including the further steps of: detecting an amount of total DNA in a standard sample of DNA of known amount using the same other regions(s) as used in step (c); and comparing the signal detected from said standard sample of DNA to the signal detected in step (c). Such a standard sample of DNA (of known amount/concentration) is readily available from commercial sources, and especially if prepared and analysed using a dilution series, can readily and efficiently be used to determine (by inter-polation/estimation from the standard curve) an absolute amount of total DNA present in the sample. Practically, such standard curve may be prepared and analysed essentially as described for the other regions (but in a separate set of standard vessels/reactions), preferably in the same run as the detection of the DMRs/other region(s); and may even use the same reaction master-mix. Accordingly, while the "DMR(s)" of the DNA control may be detected for such standard DNA, such a signal is not required to generate a standard curve. Accordingly, if the signal from a such a standard DNA sample is used to compare, the in certain embodiments where each of said detection steps comprises quantitative detection, said detected amount of said species of DNA can be expressed as an absolute amount of said species of DNA in said sample.

A determined quantitative amount of said species of DNA has utility in assessing the risk of the individual to certain medial conditions and/or if there is sufficient of such species of DNA in the sample to enable further analysis of such species of DNA to be conducted efficient, accurately and/or in a cost effective manner.

Accordingly, certain embodiments of the present invention further include the step of: comparing the amount of said species of DNA detected with a threshold amount and/or reference distribution of amounts, wherein an increase in the (or outlying) amount of said species of DNA indicates an increased risk of the individual suffering from or developing a medical condition. Threshold amounts and/or a set of amounts to form a reference distribution may be obtained from published literature and or empirical studies. For example, using published threshold values (Papantoniou et al 2013, Prenat Diag 33:682) if the total cfDNA exceeds an amount of about 7,500 Eg/mL plasma or if the foetal cfDNA fraction exceeds an amount of about 500 Eg/mL plasma, then the woman may be determined to have such an increased risk. Such a risk may instead or additional be assessed by considering: (i) the fold-increase (eg 1.5, 3, 3.5 or 4-fold increase) of foetal cfDNA (determined for such woman compared to a threshold amount), factoring into the determination that for later-term pregnancies a higher fold-increase in foetal cfDNA may be utilised (Zeybek et al 2013, J Obstet Gynaecol Res 39:632); and/or (ii) into which percentile the amount of cfDNA determined from the woman falls, from consideration of a reference distribution of amounts such as those determined from low-risk women or those which did not suffer from or develop preeclampsia, for example if the foetal cfDNA fraction falls within the $90^{th}$ percentile of such a distribution, then the woman may be considered to have an increased risk of suffering mild or severe preeclampsia (Jakobsen et al 2013, Transfusion 53:1956). Other relevant factors may be considered in determining a suitable threshold amount. For example, a pregnant women who is also suffering from breast cancer, may have a higher bias of methylation at RASSF1A present in her plasma due to both factors.

Analogously, certain embodiments of the present invention further include the step of: comparing the amount of said species of DNA detected with a threshold amount and/or reference distribution of amounts, wherein an amount of said species of DNA in excess to said threshold (or is not an outlier compared to said population) indicates that a diagnosis for an abnormality in the said species of DNA present in said sample may be performed on, preferably a separate aliquot of DNA of, said sample. For example, if foetal cfDNA fraction is greater than about 10%, 9%, 8%, 7%, 6%, 5%, 4%, 3%, 2%, 1% or 0.5% of total cfDNA present in maternal plasma, then there would be sufficient fraction or foetal cfDNA to effectively conduct a subsequent test to investigate one or more characteristics of the foetal cfDNA, for example to investigate the chance or existence of a chromosomal anomaly of mutation comprised within such foetal cfDNA (such as using NIPT based on massively parallel sequencing). In the case of twin pregnancies, the inventors determine that a minimum foetal fraction of cfDNA for NIPT of a twin pregnancy could be considered to be 8%, or about 5%, 6%, 7%, 9% or 10%, and for monochorionic twin pregnancies with concordant genotypes (apart from rare exceptions, Chen et al, 2013, Am J Med Genet A, 161A:1817), a foetal cDNA fraction of 4%, or about 2%, 3% or 5%, would be sufficient.

Therefore, the present invention also includes embodiments where comprising a further step of: performing on, preferably with a separate aliquot of DNA of, said sample an in-vitro diagnosis for an abnormality in said species of DNA present in said sample; preferably wherein, said species of DNA originates from cells of a foetus and/or the placenta of a foetus, said sample is from a pregnant female and said diagnosis is a prenatal diagnosis. Such diagnosis directed at said species of DNA present may comprise a step that uses a detection technology selected from the group consisting of: DNA sequencing, SNP analysis, digital PCR and hybridization, and in particular embodiments said detection technology is massively parallel sequencing of DNA, such as massively parallel sequencing of random and/or (exon) enriched DNA.

Such a diagnosis or test may be directed at the foetal DNA to identify a genetic mutation or chromosomal abnormality of the foetal DNA. Accordingly in certain embodiments, said species of DNA originates from cells of a foetus and/or the placenta of a foetus, said sample is from a pregnant female and said abnormality is a genetic mutation or a chromosomal abnormality, such as a chromosomal trisomy, associated with a foetal abnormality and/or a congenital disorder, In particular such embodiments, the genetic mutation is selected from the group consisting of: colour blindness, cystic fibrosis, hemochromatosis, haemophilia, phenylketonuria, polycystic kidney disease, sickle-cell and disease, Tay-Sachs disease; and/or the chromosomal abnormality is selected from the group consisting of: a trisomy (such as trisomy 21, trisomy 18, or trisomy 13), a sex-chromosome abnormality (such as Turners syndrome, Klinefelter syndrome, Noonan syndrome, Triple X syndrome, XXY syndrome, or Fragile X syndrome), a chromosomal deletion (such as Prader-Willi syndrome, Cris-du-chat syndrome, Wolf-Hirschhorn syndrome, or 22q11 deletion syndrome, Duchene muscular dystrophy), Beckwith-Wiedemann syndrome, Canvan syndrome, and neurofibromatosis. In other embodiments, the genetic mutation or chromosomal abnormality may be one or more selected from those having a clinical utility gene cards (CUGCs) of the EuroGentest2 initiative (www.eurogentest.org). In particular embodiments, the chromosomal abnormality is a trisomy (such as trisomy 21, trisomy 18, or trisomy 13), a sex-chromosome abnormality or a chromosomal deletion.

Such diagnosis or test may be directed at a species DNA to identify a genetic mutation or chromosomal abnormality of such DNA that is derived from a cell or cell-type associated with a medical condition. Accordingly in one of such embodiments, said species of DNA originates from cells of a tumour and said abnormality is a genetic mutation or a chromosomal abnormality associated with the diagnosis, prognosis or predictive treatment of a carcinoma or cancer. In particular such embodiments, the genetic mutation is selected from the group consisting of: a mutation in a tumour suppressor gene (such as TP53 (p53), BRCA1, BRCA2, APC or RB1), a mutation in a proto-oncogene (such as RAS, WNT, MYC, ERK, or TRK) and a DNA repair gene (such as HMGA1, HMGA2, MGMT or PMS2); and/or the chromosomal abnormality is a translocation (such as t(9; 22)(q34; q11) [ie, Philadelphia chromosome or BCL-ABL], t(8; 14)(q24; q32), t(11; 14)(q13; q32), t(14; 18)(q32; q21), t(10; (various))(q11; (various)), t(2; 3)(q13; p25), t(8; 21)(q22; q22), t(15; 17)(q22; q21), t(12; 15)(p13; q25), t(9; 12)(p24; p13), t(12; 21)(p12; q22), t(11; 18)(q21; q21), t(2; 5)(p23; q35), t(11; 22)(q24; q11.2-12), t(17; 22), t(1; 12) (q21; p13), t(X; 18)(p11.2; q11.2), t(1; 19)(q10; p10), t(7, 16)(q32-34; p11), t(11,16)(p11; p11), t(8,22)(q24; q11) or t(2; 8)(p11; q24)).

In a second aspect, the invention relates to a method for detecting an increased risk of an individual suffering from or developing a medical condition, said method comprising the steps:
(i) conducting a method of the present invention that determines a quantitative amount said species of DNA (and/or total DNA) in the sample; and
(ii) comparing the amount of said species of DNA detected with a threshold amount and/or a reference distribution of amounts,
wherein an increase in the (or outlying of) amount of said species of DNA (and/or total DNA) indicates an increased risk of the individual suffering from or developing said medical condition.

A third aspect of the invention relates to a composition (eg, one that is useful for, or used in, a method of the present invention), said inventive composition comprising:

one pair of PCR primers for amplifying one of said DMRs as set forth anywhere herein;
one pair of PCR primers for amplifying said other region as set forth anywhere herein;
one labelled probe for quantitative probe-based PCR, which specific for said DMR; and
one labelled probe for quantitative probe-based PCR specific for said other region and labelled with different detectable label(s) to the probe used for said DMR.

Such a composition of the present invention may further comprising:
a further pair of PCR primers for amplifying a second DMR as set forth anywhere herein; and a further labelled probe for quantitative probe-based PCR specific for said DMR and labelled with detectable label(s), optionally that is the same as that used for the probe(s) specific the first other region; and/or
a further pair of PCR primers for amplifying a second other region as set forth anywhere herein; and a further labelled probe for quantitative probe-based PCR specific for said other region and labelled with detectable label(s) that is different to those used probes for said DMRs; and optionally that is the same as that used for the probe(s) specific the first other region.

A fourth aspect of the invention relates to a kit (for example a kit of separate components; such as a kit of holders or vessels, each holding a different component of the kit), such kit comprising a set of primers and probes as comprised in a composition of the present invention. A kit of the present invention may comprise additional components. For example, the kit may additionally comprise: (i) a printed manual or computer readable memory comprising instructions to use said primers and probes, including to use them to practice a method of the present invention and/or to produce or use a composition of the present invention; and/or (ii) one or more other item, component or reagent useful for the practice of a method of the present invention; and/or the production or use of the composition of the present invention, including any such item, component or reagent disclosed herein, such as a reagent that differently modifies methylated and non-methylated DNA as set forth anywhere herein.

A further aspect of the invention relates to a computer program product comprising a computer readable medium encoded with a plurality of instructions for controlling a computing system to perform and/or manage an operation for determining: (x) an increased risk of an individual suffering from or developing a medical condition and/or (y) if a diagnosis for an anomaly in a species of DNA originating from cells of a given type may be performed, in each case from a sample from an individual comprising a species of DNA originating from cells of a given type in admixture with differently methylated DNA not originating from cells of said type, the DNA in present in said sample being treated with a reagent that differentially modifies methylated and non-methylated DNA as set forth herein; said operation comprising the steps of:
receiving: (i) one signal representing the (essentially simultaneous) quantitative detection of methylation at one or more DMRs as set forth in step (b) as described anywhere herein; and (ii) one signal representing the (essentially simultaneous) quantitative detection of total DNA using at least one other region as set forth in step (c) as described anywhere herein;
determining a parameter from the signals (i) and (ii), wherein the parameter represents a quantitative amount of said species of DNA (and/or said total DNA);

comparing the parameter to with a threshold amount and/or reference distribution of amounts; and based on such comparison, determining a classification of whether, respectively, (x) an increased risk of an individual suffering from or developing a medical condition exists; and/or (y) a diagnosis for an anomaly in a species of DNA originating from cells of a given type may be performed.

In certain embodiments, a computer program product of the present invention the operation further comprises steps of: receiving a further signal representing the quantitative detection of total DNA in a standard sample of DNA as set forth anywhere else herein; and comparing said signal with the signal representing the essentially simultaneous quantitative detection of total DNA using at least one other region, so as to determine said parameter that represents an absolute quantitative amount of said species of DNA.

In particular embodiments, the computer program product of the present invention is for an operation for determining if a diagnosis for an anomaly in said species of DNA may be performed, and said operation further comprises the step of determining from said parameter a number of random and/or enriched DNA molecules to be sequenced from, preferably from a separate aliquot of DNA of, said sample as part of said diagnosis.

One embodiment of operations performed and/or controlled by the computer program product of the invention is depicted in FIG. 5. Operation (A) receives signals (1) and (2) that represent, respectively, the methylation at the DMR(s) and the total DNA, and optionally signal (3) then represents an amount of total DNA from a standard sample. Operation (A) determines a parameter (4) from signals (1), (2) and optional (3) that represents a relative or absolute amount of DNA (eg from foetal vs total DNA). This parameter (4) is compared by operation (B) against a threshold amount (5) and/or a reference population of amounts (6) so as to classify (7) the risk of an individual suffering from a medial condition and/or if a diagnosis for an anomaly in either of the DNA in the sample may be performed.

It is to be understood that application of the teachings of the present invention to a specific problem or environment, and the inclusion of variations of the present invention or additional features thereto (such as further aspects and embodiments), will be within the capabilities of one having ordinary skill in the art in light of the teachings contained herein.

Unless context dictates otherwise, the descriptions and definitions of the features set out above are not limited to any particular aspect or embodiment of the invention and apply equally to all aspects and embodiments which are described.

All references, patents, and publications cited herein are hereby incorporated by reference in their entirety.

Certain aspects and embodiments of the invention will now be illustrated by way of example and with reference to the description, figures and tables set out herein. Such examples of the methods, uses and other aspects of the present invention are representative only, and should not be taken to limit the scope of the present invention to only such representative examples.

EXAMPLE 1: USE OF THE METHOD OF THE INVENTION IN NIPT IN MULTIPLE PREGNANCIES, INCLUDING IN CASES OF VANISHING TWINS

Sample Collection, Processing and DNA Extraction:

36 blood samples from women pregnant with multiple gestations (mono-, di- and trichorionic twin and triplet pregnancies) were collected between Nov. 6, 2012 and Nov. 16, 2013, for research & development (R&D) purposes and as part of routine non-invasive prenatal testing (NIPT) laboratory procedure. One blood sample came from a woman pregnant with triplets, the remaining 35 samples came from twin pregnancies. From each pregnant woman carrying a multiple pregnancy two samples each with 7-10 ml venous blood were collected using Streck cell-free DNA blood collection tubes (Streck). The blood samples were shipped to the diagnostic laboratory with a maximum delivery time of 4 days. Other blood samples from pregnant females analysed herein were similarly collected.

Plasma preparation was performed by centrifugation (1600 g for 10 min at 4° C.) and plasma separation followed by a second centrifugation step (16000 g for 10 min at 4° C.). Extraction of total cell-free DNA (cfDNA) was performed with QIAamp Circulating Nucleic Acid Kit (Qiagen) according to the manufacturer protocol using 3.0-4.0 ml plasma with a final elution volume of 60 ul AVE-buffer (Qiagen).

DNA Quantification:

Foetal cell-free DNA (foetal cfDNA) was detected and quantified in relation to total cell-free DNA (total cfDNA) in order to determine the foetal cDNA fraction as both a relative concentration and absolute amount using a method of the present invention. From the eluted cell-free DNA, 11 ul were digested with the CpG-methylation sensitive enzymes HhaI (0.4 U/ul), HpaII (0.3 U/ul) and BstUI (0.3 U/ul) in a 22 ul reaction using CutSmart™ Buffer (New England Biolabs). The reaction was incubated for 60 min at 37° C. and 60 min at 60° C. 10 ul from the digestion reaction was used as template DNA for quantitative probe-based PCR (reactions were conducted in duplicate), described briefly as follows.

A 25 ul PCR reaction using a 2-fold concentrated PCR master mix (QuantiFast Multiplex PCR Kit, Qiagen) was conducted. Primers that span CpG methylation sensitive restriction enzyme sites of the respective region that is differentially methylated between foetal and maternal DNA (as a DMR) were used in combination with FAM-labelled probes for such DMRs, and primers that do not span any restriction enzyme sites, an other region that is not differentially methylated between foetal and maternal DNA (as an OR) are used in combination with VIC-labelled probes for such ORs. The sequences of the primers and labelled probes used in this example are described in TABLE 1, and the thermocycler profiles used for the quantitative probe-based (TaqMan) PCR (LightCycler 480 II Instrument; Roche) are described in TABLE 2. In this example, the probes used to detect the presence of the two DMRs, are each labelled with the same detectable fluorescein amidite (FAM) fluorescent moiety, and each with the same minor binding grove (MGB) non-fluorescent quencher (NFQ) moiety, and the probes used to detect the presence of the two ORs, are each labelled with the same detectable VIC (life Technologies) fluorescent moiety, and each with the same MGBNFQ moiety.

TABLE 1

Quantitative (probe-based) PCR components

| Region | Component | Sequence (5'-3')* | SEQ ID No. | Stock Conc | ul for 1x | Final uM Conc |
|---|---|---|---|---|---|---|
| | Master-mix | N/A | | 2x | 12.5 | 1x |
| RASSF1A DMR | DMR1-For | ATT GAG CTG CGG GAG CTG GC | 1 | 100 uM | 0.35 | 1.4 |
| | DMR1-Rev | TGC CGT GTG GGG TTG CAC | 2 | 100 uM | 0.35 | 1.4 |
| | DMR1-Probe | [FAM]-ACC CGG CTG GAG CGT-[MGBNFQ] | 3 | 100 uM | 0.035 | 0.14 |
| RASSF1A Other region | OR1-For | GGT CAT CCA CCA CCA AGA AC | 4 | 100 uM | 0.35 | 1.4 |
| | OR1-Rev | TGC CCA AGG ATG CTG TCA AG | 5 | 100 uM | 0.35 | 1.4 |
| | OR1-Probe | [VIC]-GGG CCT CAA TGA CTT CAC GT-[MGBNFQ] | 6 | 100 uM | 0.035 | 0.14 |
| TBX3 DMR | DMR2-For | GGT GCG AAC TCC TCT TTG TC | 7 | 100 uM | 0.35 | 1.4 |
| | DMR2-Rev | TTA ATC ACC CAG CGC ATG GC | 8 | 100 uM | 0.35 | 1.4 |
| | DMR2-Probe | [FAM]-CCC TCC CGG TGG GTG ATA AA-[MGBNFQ] | 9 | 100 uM | 0.035 | 0.14 |
| TBX3 Other region | OR2-For | TGT TCA CTG GAG GAC TCA TC | 10 | 100 uM | 0.35 | 1.4 |
| | OR2-Rev | CAG TCC ATG AGG GTG TTT G | 11 | 100 uM | 0.35 | 1.4 |
| | OR2 Probe | [VIC]-GAG GTC CCA TTC TCC TTT-[MGBNFQ] | 12 | 100 uM | 0.035 | 0.14 |
| General reagents | DMSO | N/A | | 100% | 0.025 | 0.625 |
| | MgCl2 | N/A | | 50 mM | 2 | 1 |
| | DNA sample | N/A | | | 10 | |
| | Water | | | | – | |
| | Total | | | | 25 | |

*The dyes used for each probe are shown in "[ ]" parentheses

TABLE 2

Thermocycler profiles

| Step | Temperature | Time | Cycles | Analysis mode |
|---|---|---|---|---|
| Pre-incubation | 95° C. | 5 min | 1 | None |
| Denaturation | 95° C. | 10 sec | 45 | Quantification |
| Annealing | 60° C. | 10 sec | | None |
| Elongation | 72° C. | 8 sec | | Single |
| Cooling | 42° C. | | | None |

The assay design used in this example is based on two marker DMRs which are described to be hypomethylated in maternal DNA and hypermethylated in foetal DNA (Nygren, et al, 2010: Clin Chem 56, 1627; Chan et al, 2006: Clin Chem 42, 2211; Chiu et al, 2007: Am J Pathol 170, 941), and two other regions (ORs) not differentially methylated between maternal and foetal DNA which are each located between about 20 bp and 20 kb of their DMR. In particular, the methylation insensitive locus located in RASSF1A is located between 8 kb and 9 kb (8.97 kb) downstream of the methylation sensitive locus located in RASSF1A, and the methylation insensitive locus located in TBX3 is located between 10 kb and 11 kp (10.64 kb) downstream of the methylation sensitive locus located in TBX3. FIG. 2 depicts the respective arrangements and detection modalities of the two DMRs and the two other regions used in this example.

Parallel probe-based quantitative PCR reactions were performed (in separate reactions within the same PCR run) using for template a serial dilution of male genomic DNA (Promega) having known concentrations as a standard. The foetal cfDNA fraction was calculated by relative quantification of signals in the FAM channel (DMR; ie detecting foetal cfDNA) versus the VIC channel (ORs; ie detecting total cfDNA), and the absolute total cfDNA amount was calculated by absolute quantification of signals in the VIC channel obtained from the sample compared to the VIC channel obtained from the dilution series of standard DNA of known concentration. Such relative and absolute quantifications were conducted using LightCycler 480 Software release 1.5.0 (Roche).

Maternal Plasma DNA Sequencing and Data Analysis to Identify Foetal Aneuploidy:

DNA sequencing libraries were prepared using NEBNext Ultra™ DNA Library Prep Kit from Illumina. Libraries were prepared according to the manufacturer protocol automated on a Hamilton STARplus robot. Library quality and quantity was measured using a Bioanalyzer instrument (Agilent) and a Qbit Fluorometer (Invitrogen). Based on the library quantification dilutions and equimolar pools of 12 samples per pool were prepared. The pooled samples were sequenced on one lane of an Illumina v3 flow cell on an Illumina HiSeq2000 sequencer. Clonal clusters were generated using TruSeq SR Cluster Kit v3-cBot-HS on a cBot Cluster generation System according to the manufacturer protocol. Bioinformatic analysis to identify foetal chromosomal aneuploidy was carried out as described previously, with z-scores≥3 indicating the presence of a foetal trisomy 21 (Stumm et al 2014, Europ Prenat Diag 34:185). In cases of a positive test result for foetal aneuploidy from this method, the result was confirmed by invasive diagnostic methods.

Results:

Characteristics, % foetal fraction of cfDNA and aneuploidy test results for the blood samples are given in TABLE 3. There were two positive test results indicating foetal trisomy 21. Both were confirmed by karyotyping after amniocentesis; thus, the false positive rate in this study was 0%. One blood sample represented monochorionic twins with concordant karyotypes [47, XY, +21] and the other one represented dichorionic twins with discordant karyotypes [47, XY, +21 and 46,XX]. In both samples the foetal fraction was as high as 18.0 and 24.8%, respectively. All other NIPT results were negative for trisomies 21, 18 and 13. There is no evidence for false-negative NIPT results so far in the pregnancies included in this study. Nevertheless, a number of pregnancies are still on-going (with the last birth of the patients expected in mid May 2014) and therefore, the final detection rate is still uncertain.

present invention were compared with the values obtained from Y-chromosomal reads from next generation sequencing

TABLE 3

Characteristics and NIPT results for the collected blood samples

| Sample | Chr13 z-score | Chr18 z-score | Chr21 z-score | Foetal DNA fraction (%) | Gestational age (p.m.) | No. of foetuses, chorinicity amnionicity | NIPT result |
|---|---|---|---|---|---|---|---|
| LCMPC05 | 1.3 | −1.0 | −0.8 | 16.7 | 11 + 5 | 3, trichorionic, triamniotic | negative |
| LCMPC06 | −0.4 | 1.1 | 8.5 | 18.0 | 13 + 2 | 2, monochorionic, n.a. | T21 positive |
| LCMPC07 | −1.0 | 0.3 | 0.9 | 7.9 | 19 + 0 | 2, dichorionic, diamniotic | negative |
| LCMPC08 | 0.7 | 1.2 | 0.0 | 16.5 | 18 + 1 | 2, dichorionic, diamniotic | negative |
| LCMPC09 | 0.6 | −0.8 | 0.7 | 8.9 | 11 + 5 | 2, monochorionic, diamniotic | negative |
| LCMPC10 | 0.3 | 0.7 | −0.7 | 17.6 | 20 + 4 | 2, dichorionic, diamniotic | negative |
| LCMPC11 | −0.9 | −0.8 | 0.7 | 11.5 | 23 + 0 | 2, dichorionic, diamniotic | negative |
| LCMPC12 | −0.9 | −0.7 | −2.0 | 13.3 | 11 + 1 | 2, monochorionic, diamniotic | negative |
| LCMPC13 | 1.3 | 0.1 | 0.3 | 21.4 | 16 + 0 | 2, dichorionic, diamniotic | negative |
| LCMPC14 | 0.2 | −0.3 | 0.0 | 6.8 | 12 + 5 | 2, n.a., n.a. | negative |
| LCMPC15 | 2.2 | 0.1 | 14.7 | 24.8 | 16 + 0 | 2, dichorionic, diamniotic | T21 positive |
| LCMPC16 | 1.1 | 1.7 | 0.5 | 5.4 | 12 + 5 | 2, n.a., n.a. | negative |
| LCMPC17 | 0.7 | 1.4 | 0.5 | 16.5 | 14 + 2 | 2, n.a., n.a. | negative |
| LCMPC18 | 0.3 | 2.6 | 0.0 | 18.5 | 18 + 3 | 2, n.a., n.a. | negative |
| LCMPC19 | −0.2 | 0.8 | 0.3 | 16.6 | 14 + 0 | 2, dichorionic, diamniotic | negative |
| LCMPC20 | −0.7 | −0.9 | 0.1 | 13.1 | 15 + 4 | 2, dichorionic, diamniotic | negative |
| LCMPC21 | 1.0 | −0.7 | 1.2 | 8.4 | 9 + 3 | 2, dichorionic, diamniotic | negative |
| LCMPC22 | −1.1 | −0.2 | 0.3 | 5.6 | 16 + 2 | 2, monochorionic, n.a. | negative |
| LCMPC23 | −2.2 | 2.2 | −0.8 | 20.6 | 19 + 5 | 2, monochorionic, n.a. | negative |
| LCMPC24 | −1.6 | −0.4 | −0.5 | 14.7 | 22 + 2 | 2, monochorionic, diamniotic | negative |
| LCMPC25 | −0.8 | −0.2 | −1.5 | 12.1 | 11 + 5 | 2, n.a., n.a. | negative |
| LCMPC26 | −0.4 | −0.6 | −1.3 | 7.5 | 13 + 0 | 2, dichorionic, diamniotic | negative |
| LCMPC27 | 0.5 | −0.8 | −0.4 | 16.3 | 12 + 6 | 2, n.a., n.a. | negative |
| LCMPC28 | −1.2 | −0.3 | −0.7 | 19.4 | 10 + 1 | 2, dichorionic, diamniotic | negative |
| LCMPC29 | −0.8 | 0.7 | −0.4 | 14.2 | 13 + 2 | 2, monochorionic, n.a. | negative |
| LCMPC30 | 0.7 | 0.3 | 0.9 | 14.9 | 12 + 2 | 2, monochorionic, monoamniotic | negative |
| LCMPC31 | −0.2 | 0.3 | −0.9 | 19.3 | 19 + 1 | 2, dichorionic, diamniotic | negative |
| LCMPC32 | −1.1 | 2.5 | −2.2 | 11.6 | 20 + 0 | 2, dichorionic, diamniotic | negative |
| LCMPC33 | 0.2 | 2.2 | −1.6 | 8.6 | 11 + 0 | 2, dichorionic, diamniotic | negative |
| LCMPC34 | −1.0 | 1.2 | 0.0 | 15.1 | 15 + 4 | 2, dichorionic, diamniotic | negative |
| LCMPC35 | −0.3 | −0.8 | −0.3 | 19.2 | 12 + 0 | 2, dichorionic, diamniotic | negative |
| LCMPC36 | −1.4 | −0.5 | −0.8 | 13.9 | 12 + 0 | 2, dichorionic, diamniotic | negative |
| LCMPC37 | 1.8 | −0.7 | 0.1 | 13.8 | 17 + 6 | 2, dichorionic, diamniotic | negative |
| LCMPC38 | −0.1 | 1.1 | −0.7 | 13.4 | 13 + 1 | 2, dichorionic, diamniotic | negative |
| LCMPC39 | −1.9 | 0.2 | −2.2 | 15.0 | 17 + 0 | 2, dichorionic, diamniotic | negative |
| LCMPC40 | 0.6 | −0.4 | 0.8 | 16.2 | 18 + 3 | 2, dichorionic, diamniotic | negative |

The reliable detection of foetal aneuploidy in twin pregnancies by NIPT is dependent on a sufficiently high amount of foetal cfDNA from each foetus in the maternal blood. Different data and considerations have been published on how the lower limit of foetal cfDNA fraction should be defined to ensure that each twin's contribution is above the detection threshold (Leung et al 2013, Prenat Diag 33:675; Qu et al 2007, Am J Pathol 170:941; Struble et al 2013, Fetal Diagn Ther December 7 Epub ahead of print). This is especially important for dichorionic twin pregnancies with discordant karyotypes. In the study described above, supporting information was used for the definition of the minimum foetal cDNA fraction for twin pregnancies derived from the Y-chromosomal representation, if only one of the two foetuses is male. Using the method of the present invention, the total foetal cfDNA fraction can be determined, which reflects the summary of foetal cDNA derived from both foetuses. Using the Y-chromosomal representation from the next generation sequencing, the foetal cfDNA amount can be determined for male foetuses (as described in Stumm et al 2014). Thus, in the case of mixed foetal gender the contributing amount of each foetus can be determined by subtraction of the amount of foetal cfDNA determined by the Y-chromosomal representation from the foetal cfDNA fraction measured by method of the present invention. The foetal cfDNA fractions determined by the method of the present invention were compared with the values obtained from Y-chromosomal reads from next generation sequencing for cases with known gender (see FIG. 3). There is a correlation of the amount of male specific cfDNA (y axis) to the foetal cfDNA fraction measured by method of the present invention (x axis). Thus, for twin pregnancies with male/male gender approximately true is: [y=x], for female/male genders it is: [y=0.5x] and for female/female: [y=1]. The genders of cases with similar values are male/male and in case of differing values with low Y-chromosomal representation the genders are female/female. The intermediate cases, which show about half the percentage of foetal fraction as Y-chromosomal representation, are of mixed gender. The data presented in FIG. 3 show that it is not only possible to determine the foetal genders using NIPT results for twin pregnancies, but also that the measurement of the amount of foetal fraction of cfDNA determined by the method of the present invention is surprisingly accurate as compared to frequency counting of Y chromosome sequences. On the other hand, these data support the hypothesis that each foetus of a twin pregnancy contributes roughly about half of the total foetal cfDNA fraction. This leads to the conclusion that for twin pregnancies, twice the amount of foetal cfDNA would be required, and thus a recommended minimum foetal fraction of cfDNA for NIPT of a twin pregnancy could be considered to be 8%.

For monochorionic twin pregnancies with concordant genotypes (apart from rare exceptions, Chen et al 2013, Am J Med Genet A 161A:1817), a foetal cfDNA fraction of 4% would be enough to detect a foetal aneuploidy, just as for single pregnancies. However, for routine laboratory NIPT service one major issue speaks against the implication of such different quality criteria for mono- and dichorionic pregnancies: the determination of chorionicity is dependent on the gestational age and the practical experience of the physician performing the ultrasound examination. The chorionicity is clearly detectable in the first trimester of a multiple pregnancy, but in later stages detection becomes more difficult (Sperling et al 2001, Acta Obstet Gynecol Scand 80:287). Therefore, it is a safer strategy to generally define a minimum foetal cfDNA fraction for twin pregnancies, which is applicable for monochorionic as well as for dichorionic multiple pregnancies.

Identification of Vanishing Twins:

In two cases of NIPT aneuploidy testing in which the foetal cfDNA fraction was measured using the method of the present invention, identified a trisomy 21 (z-scores 13.5 and 3.4 respectively), but also a striking discrepancy between the total foetal cfDNA fraction measured by the method of the invention and the cf-Foetal-DNA amount measured by Y-chromosome representation were observed.

For case A, two analyses of blood samples (first and back-up samples) estimated the total foetal cfDNA fraction measured the method of the present invention was 20.7% and 24.8%, respectively, whereas the foetal cfDNA according to the Y-chromosomal representation from next generation sequencing was 9.2% and 9.3%, respectively. It was speculated, and reported to the physician, that the pregnancy may be a mixed-sex twin pregnancy, who confirmed that a deceased twin had been observed during ultrasound scan at week 10. A further blood sample taken in the third trimester of the pregnancy (38+2) turned out to be negative for trisomy 21 and the foetal cfDNA amount measured by Y-chromosomal representation correlated with the foetal amount measured by QuantYfeX (21.7% and 21.4), which matched the male gender determined by karyotyping of the living foetus. At birth a foetus papyraceus was found in the placental tissue from which a sufficient amount of cells could be isolated for cell culture and following GTG banding, a trisomy 21 positive, female karyotype was confirmed (47, XX, +21).

For case B, a slightly increased Y-chromosomal representation was monitored indicating male specific cf-Foetal-DNA of 3.0% and 2.7% respectively. As the foetal cfDNA fraction estimates measured by the method of the invention were far above that (13.4% and 10.0%) we hypothesized from this discrepancy in the foetal fraction measured, that two foetuses with discordant gender contribute to the foetal fraction and the male foetus being the one affected by trisomy 21. This suggestion was derived from the correlation of Y-chromosome specific foetal cfDNA amount of roughly 3% with the elevated z-score around the cut-off value of 3.0. Since the examination was clearly requested for a singleton pregnancy, the male specific foetal cfDNA was suspected to stem from a vanishing twin—maybe the carrier of a trisomy 21—that was either not recognized or not indicated on the consent form for NIPT. Thus, the result was reported to be indecisive for chromosome 21 and the conflicting data was reported to the responsible physician, including a notice regarding the potential vanishing twin, for further clarification via ultrasound. The responsible physician subsequently confirmed that the pregnancy had started as twin and later continued as a singleton pregnancy. The gender of the living and apparently healthy foetus was confirmed to be female and thus, the foetal cfDNA that caused the increased z-score for trisomy 21 can clearly be assigned to a deceased male foetus. The pregnancy is still on-going and further analysis of placental tissue and blood of the living foetus is not yet possible.

EXAMPLE 2: IMPROVED DETECTION SENSITIVITY USING TWO DIFFERENTIALLY METHYLATED REGIONS USING THE SAME DETECTABLE MOIETY/MOIETIES FOR EACH DIFFERENTIALLY METHYLATED REGION

The inventors were surprised to observe that a complex and multiplex reaction detecting two DMRs using the same detectable moiety/moieties for each of said DMR (as well as two other regions (OR) not differentially methylated) was more sensitive to detect foetal cfDNA fraction than previous detection reactions that each detected—in separate PCR reactions—a single DMR (as well as a single OR) (FIG. 4).

In a method of the present invention, two DMRs (those found in RASSF1A and TBX3, as described in Example 1) were detected (over 4 dilutions) with the same aliquot of DNA and reaction—effectively simultaneously (using quantitative probe-based (TaqMan) PCR) with two ORs (those found in RASSF1A and TBX3, as described in Example 1), using: (x) the same detectable moiety/moieties for each of said DMR; and (y) a detectable moiety/moieties for said at least one OR that is/are different to the detectable moiety/moieties used for said DMRs. In comparison, detection of foetal cfDNA fraction was less sensitive, as shown by detection at higher cycle numbers (Cp), if each DMR (and corresponding OR) was detected independently in separate reactions. The regions/markers, primers/probes and detection methodology was substantially as described in Example 1, except that for the single locus reactions, only the DMR and OR from a given gene (RASSF1A or TBX3) were detected simultaneously in a single reaction.

In contrast, detection of foetal cf DNA fraction using a multiplex reaction of the two DMRs using different detectable moieties (eg FAM for the RASSF1A locus and VIC for the TBX3 locus) is determined to be even less sensitive, and further is difficult to detect simultaneously with any OR; without being bound by theory, believed due to the higher complexity of colour compensation, the limited number of separately detectable fluorescent markers and/or the "bleaching" effects from so many fluorescent markers being present in the same reaction.

Given the exponential nature of quantitative PCR detection, a higher sensitivity of detection (ie lower cycle numbers) would also equate to higher accuracy of quantification, as the correction to standard curves, and interpolation between data points, would be subject to less error than that arising with the amounts of DNA correlating to detection at higher cycle numbers.

EXAMPLE 3: DETECTION OF AN INCREASED RISK OF A PREGNANT WOMAN SUFFERING FROM OR DEVELOPING PREECLAMPSIA (PROPHETIC EXAMPLE)

Using a method of the present example, pregnant women are assessed for their risk of suffering from or developing preeclampsia as follows. Firstly, a blood sample is collected from the woman for whom such risk to be assessed and total cfDNA extracted from the plasma of such sample substantially in accordance with the procedures described in Example 1. Secondly, using a method substantially as described in Example 1, a relative and/or absolute amount of foetal cfDNA and total cfDNA present in the plasma is determined, where the absolute amount of foetal and/or total cfDNA can be expressed as the amount of genome equivalents ("Eq"). Thirdly, such determined amount of cfDNA and/or total cfDNA is compared to a threshold amount or a reference distribution of amounts, and the women is determined to be at increased risk of suffering from or developing preeclampsia if the amount of foetal cfDNA or total cfDNA exceeds such threshold value and/or is an outlier in such distribution.

For example, using published threshold values (Papantoniou et al 2013, Prenat Diag 33:682) if the total cfDNA exceeds an amount of about 7,500 Eg/mL plasma or if the foetal cfDNA fraction exceeds an amount of about 500 Eg/mL plasma, then the woman is determined to have such an increased risk. Such a risk may instead or additional be assessed by considering: (i) the fold-increase (eg 1.5, 3, 3.5 or 4-fold increase) of foetal cfDNA (determined for such woman compared to a threshold amount), factoring into the determination that for later-term pregnancies a higher fold-increase in foetal cfDNA may be utilised (Zeybek et al 2013, J Obstet Gynaecol Res 39:632); and/or (ii) into which percentile the amount of cfDNA determined from the woman falls, from consideration of a reference distribution of amounts determined from low-risk women or women who did not suffer from or develop preeclampsia, for example if the foetal cfDNA fraction falls within the $90^{th}$ percentile of such a distribution, then the woman is considered to have an increased risk of suffering mild or severe preeclampsia (Jakobsen et al 2013, Transfusion 53:1956).

In this example, t detection of a risk is conducted using a computer program product that performs the operations represented by FIG. 5. Operation (A) receives signals (1) and (2) representing, respectively, foetal and total cfDNA are used by the computer program product to determine a parameter (4) that represents the relative and/or absolute amount of foetal (or total) cfDNA present in the plasma of the woman. This operation may optional receive a signal (3) representing an absolute amount of standard DNA. A second operation (B) compares such determined parameter (4) against a threshold amount (5) and/or a reference population of amounts (6) so as to determine and report (7) whether or not—and based on such comparison—the woman is determined to be at increase risk of suffering or developing preeclampsia.

EXAMPLE 4: DETECTION OF TUMOUR-ASSOCIATED DNA IN SAMPLES FROM CANCER PATIENTS (PROPHETIC EXAMPLE)

Methylation of RASSF1A and at least one other DMR such as ER-beta (oestrogen receptor beta), RAR-beta2 (retinoic acid receptor beta 2) and/or Cyclin D2 is used to detect cfDNA derived from a tumour and to assess the risk of women suffering from breast cancer. Specific methylation at such DMRs is a characteristic of tumour-derived cfDNA, and a method of the present invention is used to detect and to quantify the amount tumour derived cfDNA in the plasma of women, and those determined to have elevated (or outlying) amounts of tumour-derived cfDNA are determined to be at increased risk from suffering from or developing breast cancer. Essentially, the process described in Example 3 is followed except that DMR2 and OR2 are located in one of ER-beta, RAR-beta2 or Cyclin D2, rather than TBX3. Primers and probes to detect such DMR2 and OR2 for use in this embodiment of the present invention are designable by the person of ordinary skill.

In this example, a similar computer program product as described in Example 3 can be used to asses the risk for a given woman is based on the amount of tumour-derived cfDNA present in her blood, but in this example this parameter is compared against a threshold amount or distribution of amounts that is derived from a study of the amount of tumour-derived cfDNA present in control and breast-cancer patients; and those women having an elevated (or outlying) amount of tumour-derived cfDNA are considered to have an increased risk of suffering from or developing breast cancer.

In view of the above, it will be appreciated that the present invention also relates to the following items:

1. A method for detecting in a sample from an individual an amount of a species of DNA originating from cells of a given type, which sample comprises said species of DNA in admixture with differently methylated DNA not originating from cells of said type; said method comprising the steps:
   (a) treating the DNA present in said sample with a reagent that differentially modifies methylated and non-methylated DNA;
   (b) detecting in said sample the presence of methylation in said species of DNA at one or more differentially methylated region(s) (DMR(s)) that is(are) differently methylated between said species of DNA and the DNA not originating from cells of said type, the modification of DNA of such DMR by said reagent is sensitive to methylation of DNA, wherein the presence of methylated DNA at said DMR indicates the presence of said amount of species of DNA in said sample and the absence of methylated DNA at said DMR indicates the absence of said species of DNA in said sample; and
   (c) detecting an amount of total DNA present in said sample using at least one other region that is not differently methylated between said species of DNA and the DNA not originating from cells of said type, the modification of which regions(s) by said reagent is insensitive to methylation of DNA,
   wherein, said other region is located between about 20 bp and about 20 kb upstream or downstream of said DMR.
2. The method of item 1, wherein said detection in step (b) and said detection in step (c) are made using the same aliquot of DNA of said sample, and in the same reaction/detection vessel, and effectively simultaneously for such DMR and other region(s), and using: (x) a detectable label(s) for said DMR(s); and (y) a different detectable label(s) for said other region(s).
3. The method of item 1 or 2, wherein said detection in step (b) comprises using two or more of said DMRs.
4. The method of item 3, wherein the same detectable label(s) is(are) used for each of said DMRs.
5. The method of any one of items 1 to 4, wherein prior to or as part of said detection in step (b) and/or step (c), each DNA region comprising said DMR(s) and/or said other region(s), respectively, is(are) amplified.
6. The method of any one of items 1 to 5, wherein each detectable label used in step (b) and/or step (c), is independently selected from the group consisting of: fluorescent, protein, small molecule or radioactive label.
7. The method of any one of items 1 to 6, wherein said detection in step (b) comprises real-time quantitative probe-based PCR using at least one labelled probe specific for one of said DMR(s).

8. The method of any one of items 1 to 7, wherein said detection in step (c) comprises real-time quantitative probe-based PCR using at least one labelled probe specific for one of said other region(s).
9. The method of any one of items 1 to 8, wherein said other region is located upstream or downstream of said DMR within a distance selected from the group consisting of: between about 16 kb to 20 bp, 14 kb to 20 bp, 12 kb to 20 bp, 10 kb to 20 bp, 8 kb to 20 bp, 6 kb to 20 bp, 5 kb to 20 bp, 4 kb to 20 bp, 3 kb to 2 bp, 16 kb to 20 bp, 1 kb to 20 bp, 500 bp to 20 bp, 200 bp to 20 bp, 20 kb to 15 kb, 15 kb to 10 kb, 12 kb to 8 kb, 10 kb to 8 kb, 11 kb to 7 kb, 11 kb to 10 kb, 9 kb to 8 kb, 8 kb to 6 kb, 6 kb to 4 kb, 4 kb to 2 kb, 2 kb to 500 bp, 1 kb to 100 bp, 500 bp to 50 bp, 400 bp to 200 bp and 500 bp to 100 bp.
10. The method of any one of items 1 to 9, wherein said detection in step (c) comprises using at least two of said other regions; preferably wherein, the number of said other regions is the same as the number of DMRs used in step (b); more preferably wherein, one of said other regions is located between about 20 bp and about 20 kb upstream or downstream of a DMR used in step (b) and each other of the said other regions is located between about 20 bp and about 20 kb upstream or downstream of another of said DMRs.
11. The method of item 10, wherein said detection in step (c) is made using the same detectable label(s) for each of said other regions.
12. The method of item 10 or 11, wherein said detection in step (c) comprises multiplex real-time probe-based quantitative PCR using at least two labelled probes each of which is specific for one of said other regions.
13. The method of any one of items 1 to 12, wherein said detection in step (c) and said detection in step (b) are made using the same aliquot of DNA of said sample, and in the same reaction/detection vessel, and effectively simultaneously with each other, and by multiplex real-time quantitative probe-based PCR using at least one labelled probe specific for each of said DMR(s) and other regions(s).
14. The method any one of items 1 to 13, wherein said species of DNA originates from cells of a foetus and/or the placenta of a foetus and said sample is from a pregnant female; preferably wherein, said species of DNA is circulating cell-free DNA and said sample is a blood fraction such as plasma or serum.
15. The method of item 14, wherein said DMR(s) comprises at least one, preferably at least two, methylation site(s) specific for said reagent, and at least one of said DMR(s) is located in a portion of the genome and/or gene selected from the group consisting of: RASSF1A, TBX3, HLCS, ZFY, CDC42EP1, MGC15523, SOX14 and SPN; preferably wherein,
two or more of said DMRs are used in detection step (b) and each of said DMRs is located in a portion of the genome and/or gene selected from the group consisting of: RASSF1A, TBX3, HLCS, ZFY, CDC42EP1, MGC15523, SOX14 and SPN; and/or
said DMR is located between about positions 4,700 bp and 5,600 bp of RASSF1A or about positions 1,660 bp and 2,400 bp of TBX3; more preferably wherein,
two or more of said DMRs are used in detection step (b) and comprise those located between about positions 4,700 bp and 5,600 bp of RASSF1A and about positions 1,660 bp and 2,400 bp of TBX3.
16. The method of item 14 or 15, wherein said other region is located in a portion of the genome and/or gene selected from the group consisting of: RASSF1A, TBX3, HLCS, ZFY, CDC42EP1, MGC15523, SOX14 and SPN; preferably wherein,
said other region comprises a region without a methylation site specific for said reagent and said locus is located in the genes RASSF1A or TBX3, more preferably wherein,
two or more of said other regions are used in detection step (c) and comprise those located between about positions 14,220 bp and 13,350 bp of RASSF1A and about positions 12,400 bp and 13,000 bp of TBX3.
17. The method any one of items 14 to 16, wherein said pregnant female is susceptible to a pregnancy-associated medical condition; preferably wherein, said pregnancy-associated medical condition is selected from the group consisting of: preeclampsia, preterm labour, intrauterine growth retardation and vanishing twin.
18. The method of any one of items 1 to 13, wherein said species of DNA originates from a cell type associated with a medical condition; preferably wherein, said medical condition is one selected from the group consisting of: a cell proliferative disorder, an infection/infectious disease, a wasting disorder, a degenerative disorder, an (auto)immune disorder, kidney disease, liver disease, inflammatory disease, acute toxicity, chronic toxicity, myocardial infarction, and a combination of any of the forgoing; more preferably wherein, said species of DNA is circulating cell-free DNA and said sample is a blood fraction such as plasma or serum.
19. The method of item 18, wherein said species of DNA originates from cells of a tumour; preferably wherein, said tumour is a carcinoma or cancer of an organ selected from the group consisting of: liver, lung, breast, colon, oesophagus, prostate, ovary, cervix, uterus, testis, brain, bone marrow and blood.
20. The method of item 19, wherein said DMR(s) comprises at least one, preferably at least two, methylation site(s) specific for said reagent, and at least one of said DMR(s) is located in a portion of the genome and/or a gene selected from the group consisting of: a tumour suppressor gene, p16, SEPT9, RASSF1A, GSTP1. DAPK, ESR1, APC, HSD17B4 and H1C1; preferably wherein, said DMR is located in RASSF1A; more preferably wherein, said DMR is located between about positions 4,700 bp and 5,600 bp of RASSF1A; and/or more preferably wherein, said other region is located between about positions 14,220 bp and 13,350 bp of RASSF1A.
21. The method of any one of items 1 to 20, wherein said sample is a tissue sample or a sample of biological fluid; preferably wherein, said sample is a sample of biological fluid selected from the group consisting of: whole blood, a blood fraction, urine, saliva, sweat, ejaculate, tears, phlegm, vaginal secretion, vaginal wash and colonic wash; more preferably wherein, said sample is a plasma or serum sample.
22. The method of any one of items 1 to 21, wherein said reagent that differentially modifies methylated and non-methylated DNA comprises bisulphite.
23. The method of any one of items 1 to 21, wherein said reagent that differentially modifies methylated and non-methylated DNA comprises an agent that selectively digests unmethylated DNA over methylated DNA, preferably wherein, said agent comprises:
at least one methylation sensitive enzyme;
at least one methylation sensitive restriction enzyme; and/or an agent selected from the group consisting of: AatII, AciI, AclI, AfeI, AgeI, AgeI-HF, AscI, AsiSI, AvaI, BceAI, BmgBI, BsaAI, BsaHI, BsiEI, BsiWI, BsmBI, BspDI, BsrFI, BssHII, BstBI, BstUI, ClaI, EagI, FauI, FseI, FspI, HaeII, HgaI, HhaI, HinP1I, HpaII, Hpy99I, HpyCH4IV, KasI, MluI, NaeI, NarI, NgoMIV, NotI, NotI-HF, NruI, Nt.BsmAI, Nt.CviPII, PaeR7I, PluTI, PmlI, PvuI, PvuI-HF, RsrII, SacII, SalI, SalI-HF, SfoI, SgrAI, SmaI, SnaBI, TspMI and ZraI.

24. The method of any one of items 1 to 23, wherein each of said detection steps comprises quantitative detection and said detected amount of said species of DNA is expressed as a relative concentration of said species of DNA to the total DNA in said sample.

25. The method of any one of items 1 to 23, further comprising the steps:
    detecting an amount of total DNA in a standard sample of DNA of known amount using the same other region(s) as used in step (c); and
    comparing the signal detected from said standard sample of DNA to the signal detected in step (c).

26. The method of item 25, wherein each of said detection steps comprises quantitative detection and said detected amount of said species of DNA is expressed as an absolute amount of said species of DNA in said sample.

27. The method of item 24 or 26, further comprising the step:
    comparing the amount of said species of DNA detected with a threshold amount and/or reference distribution of amounts, wherein: (x) an increase in, or outlying of, the amount of said species of DNA indicates an increased risk of the individual suffering from or developing a medical condition; and/or (y) an amount of said species of DNA in excess to said threshold, or outlying from said distribution, indicates that a diagnosis for an abnormality in the said species of DNA present in said sample may be performed on, preferably a separate aliquot of DNA of, said sample.

28. The method of any one of items 24 to 27, further comprising the step:
    performing on, preferably with a separate aliquot of DNA of, said sample, a diagnosis for an abnormality in said species of DNA present in said sample; preferably wherein, said species of DNA originates from cells of a foetus and/or the placenta of a foetus, said sample is from a pregnant female and said diagnosis is a prenatal diagnosis.

29. The method of item 28, wherein said diagnosis comprises a step that uses a detection technology selected from the group consisting of: DNA sequencing, SNP analysis, digital PCR and hybridisation; preferably wherein, said detection technology is massively parallel sequencing of DNA; more preferably wherein said detection technology is massively parallel sequencing of random and/or enriched DNA.

30. The method of item 28 or 29, wherein:
    (x) said species of DNA originates from cells of a foetus and/or the placenta of a foetus, said sample is from a pregnant female and said abnormality is a genetic mutation or a chromosomal abnormality, such as a chromosomal trisomy, associated with a foetal abnormality and/or a congenital disorder; preferably wherein:
        said genetic mutation is selected from the group consisting of: colour blindness, cystic fibrosis, hemochromatosis, haemophilia, phenylketonuria, polycystic kidney disease, sickle-cell and disease, Tay-Sachs disease; and/or
        said chromosomal abnormality is selected from the group consisting of: a trisomy (such as trisomy 21, trisomy 18, or trisomy 13), a sex-chromosome abnormality (such as Turners syndrome, Klinefelter syndrome, Noonan syndrome, Triple X syndrome, XXY syndrome, or Fragile X syndrome), a chromosomal deletion (such as Prader-Willi syndrome, Cris-du-chat syndrome, Wolf-Hirschhorn syndrome, or 22q11 deletion syndrome, Duchene muscular dystrophy), Beckwith-Wiedemann syndrome, Canvan syndrome, and neurofibromatosis; or
    (y) said species of DNA originates from cells of a tumour and said abnormality is a genetic mutation or a chromosomal abnormality associated with the diagnosis, prognosis or predictive treatment of a carcinoma or cancer; preferably wherein:
        said genetic mutation is selected from the group consisting of: a mutation in a tumour suppressor gene (such as TP53 (p53), BRCA1, BRCA2, APC or RB1), a mutation in a proto-oncogene (such as RAS, WNT, MYC, ERK, or TRK) and a DNA repair gene (such as HMGA1, HMGA2, MGMT or PMS2); and/or
        said chromosomal abnormality is selected a translocation (such as t(9; 22)(q34; q11) [ie, Philadelphia chromosome or BCL-ABL], t(8; 14)(q24; q32), t(11; 14)(q13; q32), t(14; 18)(q32; q21), t(10; (various)) (q11; (various)), t(2; 3)(q13; p25), t(8; 21)(q22; q22), t(15; 17)(q22; q21), t(12; 15)(p13; q25), t(9; 12)(p24; p13), t(12; 21)(p12; q22), t(11; 18)(q21; q21), t(2; 5)(p23; q35), t(11; 22)(q24; q11.2-12), t(17; 22), t(1; 12)(q21; p13), t(X; 18)(p11.2; q11.2), t(1; 19)(q10; p10), t(7,16)(q32-34; p11), t(11,16)(p11; p11), t(8,22)(q24; q11) or t(2; 8)(p11; q24)).

31. A method for detecting an increased risk of an individual suffering from or developing a medical condition; said method comprising the steps:
    (iii) conducting the method of item 24 or 26; and
    (iv) comparing the amount of said species of DNA detected with a threshold amount and/or a reference distribution of amounts,
    wherein an increase in, or outlying of, the amount of said species of DNA indicates an increased risk of the individual suffering from or developing said medical condition 32. A composition comprising:
    one pair of PCR primers for amplifying said DMR as set forth in any of items 1 to 31;
    one pair of PCR primers for amplifying said other region as set forth in any of items 1 to 31;
    one labelled probe as set forth in item 7; and
    one labelled probe as set forth in item 8.

33. The composition of item further comprising:
    a further pair of PCR primers for amplifying a second DMR as set forth in any of items 3 to 31; and a further labelled probe as set forth in item 7 when back-referenced to item 4; and/or
    a further pair of PCR primers for amplifying a second other region as set forth in any of items 10 to 31; and a further labelled probe as set forth in item 12.

34. A kit comprising:
    the primers and probes as set forth in item 32 or 33; and
    optionally, further comprising: (i) a printed manual or computer readable memory comprising instructions to use said primers and probes to practice a method of any one of items 1 to 31 and/or to produce or use the composition of item 32 or 33; and/or (ii) one or more other item, component or reagent useful for the practice of a method of any one of items 1 to 31 and/or the production or use of the composition of item 32 or 33, including any such item, component or reagent disclosed herein, such as the reagent that differently modifies methylated and non-methylated DNA as set forth in any one of items 1 to 31.

35. A computer program product comprising: a computer readable medium encoded with a plurality of instructions for controlling a computing system to perform and/or manage an operation for determining: (x) an increased risk of an individual suffering from or developing a medical condition and/or (y) if a diagnosis for an anomaly in a species of DNA originating from cells of a given type may be performed, in each case from a sample from an individual comprising a species of DNA originating from cells of a given type in admixture with differently methylated DNA not originating from cells of said type, the DNA present in said sample being treated with a reagent that differentially modifies methylated and non-methylated DNA as set forth in any one of items 1 to 31; said operation comprising the steps of:

receiving: (i) one signal representing the quantitative detection of methylation at one or more DMRs as set forth in step (b) of any one of items 1 to 31; and (ii) one signal representing the quantitative detection of total DNA using at least one other region as set forth in step (c) any of items 1 to 31;

determining a parameter from the signals (i) and (ii), wherein the parameter represents a quantitative amount of said species of DNA;

comparing the parameter to with a threshold amount and/or reference distribution of amounts; and based on such comparison, determining a classification of whether, respectively, (x) an increased risk of an individual suffering from or developing a medical condition exists; and/or (y) a diagnosis for an anomaly in a species of DNA originating from cells of a given type may be performed.

36. The computer program product of item 35 wherein said operation further comprises the steps:

receiving a further signal representing the quantitative detection of total DNA in a standard sample of DNA as set forth in item 25; and comparing said signal with the signal set forth in (ii) of item 35, so as to determine said parameter that represents an absolute quantitative amount of said species of DNA.

37. The computer program product of item 35 or 36, wherein said operation is for determining if a diagnosis for an anomaly in said species of DNA may be performed, and further comprises the step of determining from said parameter a number of random and/or enriched DNA molecules to be sequenced from, preferably from a separate aliquot of DNA of, said sample as part of said diagnosis.

The invention claimed is:

1. A method for quantitatively detecting in a sample from an individual an amount of a species of DNA originating from cells of a given type, which sample comprises said species of DNA in admixture with differently methylated DNA not originating from cells of said type, wherein said species of DNA originates from cells of a fetus and/or the placenta of a fetus and said sample is from a pregnant female; said method comprising the steps:
  (a) treating the DNA present in said sample with a reagent that differentially modifies methylated and non-methylated DNA, wherein said reagent comprises at least one methylation sensitive restriction enzyme;
  (b) quantitatively detecting in said sample the presence of methylation in said species of DNA at one or more differentially methylated region(s) (DMR(s)) that is(are) differently methylated between said species of DNA and the DNA not originating from cells of said type, the modification of DNA of such DMR by said reagent is sensitive to methylation of DNA, wherein the presence of methylated DNA at said DMR indicates the presence of said amount of species of DNA in said sample and the absence of methylated DNA at said DMR indicates the absence of said species of DNA in said sample, wherein said DMR(s) is(are) hyper-methylated in fetal DNA and hypo-methylated in maternal DNA; and
  (c) quantitatively detecting an amount of total DNA present in said sample using at least one other region that does not comprise a site of methylation recognized by said methylation sensitive restriction enzyme, wherein, said other region is located between about 20 bp and about 20 kb upstream or downstream of said DMR; and
wherein said detection in step (b) and said detection in step (c) are made using the same aliquot of DNA of said sample, and in the same reaction/detection vessel, and effectively simultaneously for such DMR(s) and other region(s), and using: (x) a detectable label(s) for said DMR(s); and (y) a different detectable label(s) for said other region(s); and
wherein:
(A) as part of said detection in steps (b) and (c) each DNA region comprising said DMR(s) and said other region(s) are amplified; and
(B) each detectable label used in step (b) and step (c) is a fluorescent label; and
(C) said detection in step (b) comprises real-time quantitative probe-based PCR using at least one labelled probe specific for one of said DMR(s); and
(D) said detection in step (c) comprises real-time quantitative probe-based PCR using at least one labelled probe specific for one of said other region(s).

2. The method of claim 1, wherein said detection in step (b) comprises using two or more of said DMRs.

3. The method of claim 2, wherein two of said DMRs are located on separate chromosomes.

4. The method of claim 1, wherein said detection in step (c) comprises using at least two of said other regions, wherein the number of said other regions is the same as the number of DMRs used in step (b), and wherein one of said other regions is located between about 20 bp and about 20 kb upstream or downstream of a DMR used in step (b) and each other of the said other regions is located between about 20 bp and about 20 kb upstream or downstream of another of said DMRs.

5. The method of claim 4, wherein the same detectable label(s) is(are) used for each of said DMRs.

6. The method of claim 4, wherein said detection in step (c) is made using the same detectable label(s) for each of said other regions.

7. The method of claim 1, wherein said detection in step (c) and said detection in step (b) are made using the same aliquot of DNA of said sample, and in the same reaction/detection vessel, and effectively simultaneously with each other, and by multiplex real-time quantitative probe-based PCR using at least one labelled probe specific for each of said DMR(s) and other regions(s).

8. The method of claim 1, wherein said species of DNA is circulating cell-free DNA and said sample is a blood fraction.

9. The method of claim 1, wherein:
  (A) said DMR(s) comprises at least one methylation site(s) specific for said reagent, and at least one of said DMR(s) is located in a portion of the genome and/or gene selected from the group consisting of: RASSF1A, TBX3, HLCS, ZFY, CDC42EP1, MGC15523, SOX14 and SPN and/or;
  (B) said other region is located in a portion of the genome and/or gene selected from the group consisting of: RASSF1A, TBX3, HLCS, ZFY, CDC42EP1, MGC15523, SOX14 and SPN.

10. The method of claim 9, wherein at least one of said DMRs is located between about positions 4,700 bp and 5,600 bp of RASSF1A or about positions 1,660 bp and 2,400 bp of TBX3.

11. The method of claim 1, wherein said sample is a tissue sample or a sample of biological fluid, wherein said sample is a sample of biological fluid selected from the group consisting of: whole blood, a blood fraction, urine, saliva, sweat, ejaculate, tears, phlegm, vaginal secretion, vaginal wash and colonic wash.

12. The method of claim 11, wherein said sample is a plasma or serum sample.

13. The method of claim 1, wherein said at least one methylation sensitive restriction enzyme is selected from the group consisting of: AatII, AciI, AclI, AfeI, AgeI, AgeI-HF, AscI, AsiSI, AvaI, BceAI, BmgBI, BsaAI, BsaHI, BsiEI, BsiWI, BsmBI, BspDI, BsrFI, BssHII, BstBI, BstUI, ClaI, EagI, FauI, FseI, FspI, HaeII, HgaI, HhaI, HinP1I, HpaII, Hpy99I, HpyCH4IV, KasI, MluI, NaeI, NarI, NgoMIV, NotI, NotI-HF, NruI, Nt.BsmAI, Nt.CviPII, PaeR7I, PluTI, PmlI, PvuI, PvuI-HF, RsrII, SacII, SalI, SalI-HF, SfoI, SgrAI, SmaI, SnaBI, TspMI and ZraI.

14. The method of claim 1:

(A) wherein each of said detection steps comprises quantitative detection and said detected amount of said species of DNA is expressed as a relative concentration of said species of DNA to the total DNA in said sample; or
(B) wherein said method further comprises the steps:
    detecting an amount of total DNA in a standard sample of DNA of known amount using the same other region(s) as used in step (c); and
    comparing the signal detected from said standard sample of DNA to the signal detected in step (c); and
optionally, wherein each of said detection steps comprises quantitative detection and said detected amount of said species of DNA is expressed as an absolute amount of said species of DNA in said sample.

15. The method of claim 14, further comprising the step: comparing the amount of said species of DNA detected with a threshold amount and/or reference distribution of amounts, wherein: (x) an increase in, or outlying of, the amount of said species of DNA indicates an increased risk of the individual suffering from or developing a pregnancy-associated medical condition; and/or (y) an amount of said species of DNA in excess to said threshold, or outlying from said distribution, indicates that a prenatal diagnosis for a genetic mutation or a chromosomal abnormality in the said species of DNA present in said sample may be performed a separate aliquot of DNA of said sample.

16. The method of claim 1, wherein the other region is located upstream or downstream of one of said DMRs within a distance selected from the group consisting of: between about 15 kb to 10 kb, 12 kb to 8 kb, 10 kb to 8 kb, 11 kb to 7 kb, 11 kb to 10 kb, 9 kb to 8 kb, 8 kb to 6 kb, 6 kb to 4 kb, 4 kb to 2 kb, and 2 kb to 500 bp.

17. The method of claim 1, wherein at least one of said DMRs is located on chromosome 12.

18. The method of claim 17, wherein:
(A) said DMR is located in TBX3; and
(B) said other region is located in TBX3.

19. The method of claim 18, wherein:
(A) said DMR is located between about positions 1,660 bp and 2,400 bp of TBX3; and/or
(B) said other region is located between about positions 12,400 bp and 13,000 bp of TBX3.

20. The method of claim 1, wherein said pregnant female is susceptible to a pregnancy-associated medical condition.

21. A composition comprising:
one pair of PCR primers for amplifying one first region located between about positions 4,700 bp and 5,600 bp of human RASSF1A or about positions 1,660 bp and 2,400 bp of human TBX3;
one pair of PCR primers for amplifying one other region in the human genome, wherein said other region is located between about 20 bp and about 20 kb upstream or downstream of said first region; and
one fluorescently labelled real-time quantitative PCR probe which is specific for said first region; and
one fluorescently labelled real-time quantitative PCR probe which is specific for said other region that has a different fluorescent label than that of the fluorescently labelled probe which is specific for said first region.

22. A kit comprising:
one pair of PCR primers for amplifying one first region located between about positions 4,700 bp and 5,600 bp of human RASSF1A or about positions 1,660 bp and 2,400 bp of human TBX3;
one pair of PCR primers for amplifying one other region in the human genome, wherein said other region is located between about 20 bp and about 20 kb upstream or downstream of said first region; and
one fluorescently labelled real-time quantitative PCR probe which is specific for said first region; and
one fluorescently labelled real-time quantitative PCR probe which is specific for said other region that has a different fluorescent label than that of the fluorescently labelled probe which is specific for said first region; and
optionally further comprising: (i) a printed manual or computer readable memory comprising instructions to use said primers and probes;
and/or (ii) a reagent that differently modifies methylated and non-methylated DNA, wherein said reagent comprises at least one methylation sensitive restriction enzyme.

23. A computer program product comprising: a non-transitory computer readable medium encoded with a plurality of instructions for controlling a computing system to perform and/or manage an operation for determining: (x) an increased risk of an individual suffering from or developing a medical condition and/or (y) if a diagnosis for an anomaly in a species of DNA originating from cells of a fetus and/or the placenta of a fetus may be performed; said operation comprising the steps of:
receiving: (i) a first signal from real-time quantitative probe-based PCR representing the quantitative detection of methylation at one or more differentially methylated region(s) (DMR(s)) in a species of DNA originating from cells of a fetus and/or the placenta of a fetus in a sample from a pregnant female, wherein said DMR(s) is(are) hyper-methylated in fetal DNA and hypo-methylated in maternal DNA, wherein the DNA present in said sample being treated with at least one methylation restriction enzyme; and (ii) a second signal from real-time quantitative probe-based PCR representing the quantitative detection of total DNA in the sample using at least one other region of DNA, wherein said at least one other region of DNA does not comprise a site of methylation recognized by the methylation sensitive restriction enzyme, and wherein said at least one other region of DNA is located between about 20 bp and about 20 kb upstream or downstream of said one or more DMR(s);
comparing the first signal with the second signal to thereby obtain a parameter, wherein the parameter represents an enhanced quantitative amount of said species of fetal DNA in the sample, wherein said enhanced quantitative amount is more accurate or precise than a quantitative amount of said species of fetal DNA in the sample obtained using an other region located more than 20 kb upstream or downstream of said one or more DMR(s);
comparing the parameter to a threshold amount and/or reference distribution of amounts; and
based on such comparison, determining a classification of whether, respectively, (x) an increased risk of an individual suffering from or developing a medical condition exists; and/or (y) a diagnosis for an anomaly in the species of DNA originating from the cells of the fetus and/or the placenta of the fetus may be performed.

* * * * *